US011690903B2

(12) United States Patent
Coronel et al.

(10) Patent No.: US 11,690,903 B2
(45) Date of Patent: Jul. 4, 2023

(54) COMPOSITIONS FOR BOOSTER VACCINATION AGAINST DENGUE

(71) Applicant: Sanofi Pasteur, Lyons (FR)

(72) Inventors: Diana Coronel, Mexico City (MX); Betzana Zambrano, Montevideo (UY); Fernando Noriega, Cresco, PA (US); Tram Anh Wartel, Singapore (SG); Yves Girerd-Chambaz, Paris (FR)

(73) Assignee: SANOFI PASTEUR, Lyons (FR)

( * ) Notice: Subject to any disclaimer, the term of this patent is extended or adjusted under 35 U.S.C. 154(b) by 6 days.

(21) Appl. No.: 16/652,902

(22) PCT Filed: Oct. 5, 2018

(86) PCT No.: PCT/IB2018/001219
§ 371 (c)(1),
(2) Date: Apr. 1, 2020

(87) PCT Pub. No.: WO2019/069130
PCT Pub. Date: Apr. 11, 2019

(65) Prior Publication Data
US 2020/0289637 A1  Sep. 17, 2020

Related U.S. Application Data

(60) Provisional application No. 62/568,525, filed on Oct. 5, 2017.

(51) Int. Cl.
*A61K 39/12* (2006.01)
*A61P 31/14* (2006.01)
*A61K 39/00* (2006.01)

(52) U.S. Cl.
CPC .............. *A61K 39/12* (2013.01); *A61P 31/14* (2018.01); *A61K 2039/545* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 6,696,281 | B1 | 2/2004 | Chambers et al. |
| 6,962,708 | B1 | 11/2005 | Chambers et al. |
| 7,459,160 | B2 | 12/2008 | Monath et al. |
| 7,641,907 | B2 | 1/2010 | Kinney et al. |
| 7,641,908 | B2 | 1/2010 | Kinney et al. |
| 7,718,357 | B2 | 5/2010 | Barban et al. |
| 7,718,358 | B2 | 5/2010 | Guy et al. |
| 7,718,359 | B2 | 5/2010 | Guy et al. |
| 7,968,102 | B2 | 6/2011 | Quentin-Millet |
| 8,067,565 | B2 | 11/2011 | Kinney et al. |
| 8,067,566 | B2 | 11/2011 | Kinney et al. |
| 8,142,795 | B2 | 3/2012 | Francon et al. |
| 8,227,587 | B2 | 7/2012 | Quentin-Millet |
| 8,697,353 | B2 | 4/2014 | Bouckenooghe et al. |
| 8,795,688 | B2 | 8/2014 | Kinney et al. |
| 8,852,914 | B2 | 10/2014 | Monath et al. |
| 9,169,298 | B2 | 10/2015 | Kinney et al. |
| 2004/0259224 | A1 | 12/2004 | Guirakhoo |
| 2005/0002968 | A1 | 1/2005 | Monath et al. |
| 2006/0292172 | A1 | 12/2006 | Kinney et al. |
| 2008/0014219 | A1 | 1/2008 | Barban et al. |
| 2008/0085288 | A1 | 4/2008 | Guy et al. |
| 2008/0131460 | A1 | 6/2008 | Guy et al. |

(Continued)

FOREIGN PATENT DOCUMENTS

| | | |
|---|---|---|
| EP | 1958959 | 8/2008 |
| EP | WO2016/034269 A1 * | 3/2016 |

(Continued)

OTHER PUBLICATIONS

Amaya-Larios et al; "Rick of dengue virus infection according to serostatus in individuals from dengue endemic areas of Mexico", Scientific Reports, (2020) 10:19017, pp. 1-9.

Coronel-Martinez et al; "Immunogenicity and safety of simplified vaccination schedules for the CYD-TDV dengue vaccine in healthy individuals ages 9-50 years (CYD65): a randomised, controlled, phase 2, non-inferiority study" Lancet Infect Dis 2021; 21:517-28.

Huang et al; "Immunobridging efficacy of a tetravalent dengue vaccine against dengue and against hospitalized dengue from children/adolescents to adults in highly endemic countries", Dec. 28, 2020; Transactions of the Royal Society of Tropical Medicine and Hygiene; 21 pages.

Sun et al; "A hybrid approach for the stratified mark-specific proportional hazards model with missing covariates and missing marks, with application to vaccine efficacy trials"; Applied Statistics; 2020; 69; Part 4; pp. 791-814.

(Continued)

*Primary Examiner* — Stacy B Chen
(74) *Attorney, Agent, or Firm* — McDonnell Boehnen Hulbert & Berghoff LLP

(57) ABSTRACT

The present invention is directed to a method of booster vaccination and to a vaccine composition for use in such a method, for inducing in a human subject a neutralizing antibody response, wherein said subject has previously received a primary vaccination against each of serotypes 1 to 4 of dengue virus and was dengue naïve before said primary vaccination, said composition comprising a dengue antigen of at least one of serotypes 1 to 4 or a nucleic acid construct capable of expressing said antigens in the subject, wherein said booster vaccination results in a 2-fold increase in the neutralizing antibody titre against each of serotypes 1 to 4. The invention is also directed to a method of inducing in a human subject a neutralizing antibody response comprising the administration of a vaccine composition, or to a vaccine composition for use in such a method, said composition comprising a dengue antigen of each of serotypes 1 to 4, or a nucleic acid construct capable of expressing in said subject a dengue antigen of each of serotypes 1 to 4; wherein said composition is administered as a primary vaccination, followed by a booster vaccination, and wherein the human subject is initially dengue naïve.

22 Claims, No Drawings

Specification includes a Sequence Listing.

(56) References Cited

U.S. PATENT DOCUMENTS

| | | |
|---|---|---|
| 2009/0169581 A1 | 7/2009 | Sandrine |
| 2009/0191240 A1 | 7/2009 | Monath et al. |
| 2010/0015180 A1 | 1/2010 | Francon et al. |
| 2010/0158938 A1 | 6/2010 | Guirakhoo |
| 2010/0215692 A1 | 8/2010 | Quentin-Millet |
| 2010/0221285 A1 | 9/2010 | Barban et al. |
| 2010/0239612 A1 | 9/2010 | Guy et al. |
| 2010/0255028 A1 | 10/2010 | Delagrave et al. |
| 2010/0270202 A1 | 10/2010 | Guy et al. |
| 2011/0014229 A1 | 1/2011 | Kleanthous et al. |
| 2011/0150771 A1 | 6/2011 | Kinney et al. |
| 2011/0189226 A1 | 8/2011 | Bouckenooghe et al. |
| 2011/0206730 A1 | 8/2011 | Quentin-Millet |
| 2012/0083584 A1 | 4/2012 | Kinney et al. |
| 2012/0083585 A1 | 4/2012 | Kinney et al. |
| 2013/0028934 A1 | 1/2013 | Francon et al. |
| 2013/0095136 A1 | 4/2013 | Guirakhoo |
| 2013/0149338 A1 | 6/2013 | Stinchcomb et al. |
| 2014/0220073 A1 | 8/2014 | Bouckenooghe et al. |
| 2015/0024004 A1 | 1/2015 | Monath et al. |
| 2015/0031857 A1 | 1/2015 | Kinney et al. |
| 2015/0196631 A1 | 7/2015 | Bouckenooghe et al. |
| 2015/0265695 A1 | 9/2015 | Yao et al. |

FOREIGN PATENT DOCUMENTS

| | | |
|---|---|---|
| WO | WO1998/037911 | 9/1998 |
| WO | WO2001039802 | 6/2001 |
| WO | WO2002081754 | 10/2002 |
| WO | WO2008047023 | 4/2008 |
| WO | WO2011/013097 | 2/2011 |
| WO | WO2011/146933 | 11/2011 |
| WO | WO2012/051491 | 4/2012 |
| WO | WO2014/016360 | 1/2014 |
| WO | WO2014/016362 | 1/2014 |
| WO | WO2017/005652 | 1/2017 |
| WO | WO2017/005654 | 1/2017 |

OTHER PUBLICATIONS

Yang et al; "Change point Inference in the presence of Missing Covariates for Principal Surrogate Evaluation in Vaccine Trials"; Biometrika (2020), pp. 1-14.

Henein et al; "Dengue Vaccine Breakthrough Infections Reveal Properties of Neutralizing Antibodies Linked to protection"; Journal of Clinical Investigation; May 18, 2021; 18 pages.

Forrat et al; "Analysis of hospitalized and severe dengue cases over the six-years of follow-up of the tetravalent dengue vaccine (CYD-TDV) efficacy trials in Asia and Latin America"; Clinical Infectious Diseases; Apr. 4, 2021; pp. 1-22.

Park et al; "Humoral and cellular immunogenicity and safety following a booster dose of a tetravalent dengue vaccine 5+ years after completion of the primary series in Singapore: 2-year follow-up of a randomized phase II, placebo-controlled trial"; Human Vaccines & Immunotherapeutics; Feb. 24, 2021; vol. 17; No. 7; 2107-2116.

Dayan et al., "CYD-TDV Vaccine efficacy after 1 and 2 doses among seropositive subjects in dengue endemic areas"; Abstract ASTMH Annual Meeting, Nov. 20-24, 2019.

Coronel et al., "CYD-TDV Dengue Vaccine: Alternative Vaccination Schedules with Reduced Number of Doses in Healthy Individuals Aged 9 to 50 Years in Latin America and Asia-Pacific Regions"; Abstract ASTMH Annual Meeting, Nov. 20-24, 2019.

Guy et al., "When Can One Vaccinate with a Live Vaccine after Wild-Type Dengue Infection?", Vaccines, 8(2), p. 174; https://222.ncbi.nlm.nih.gov/pmc/articles/PMC7349415/pdf/vaccines-08-00174.pdf, (2020).

Qiao et al., "Priming Effect of Dengue and Yellow Fever Vaccination on the Immunogenicity, Infectivity, and Safety of a Tretravalent Dengue Vaccine in Humans," The American Journal of Tropical medicine and Hygiene, 985(4): 724-731 (2011).

Villar et al., "Efficacy of a tetravalnet dengue vaccine in children in Latin America," N Engl J Med. 372(2):113-23 (2015) https://www.nejm.org/doi/pdf/10.1056/NEJMoa1411037?articleTools=true.

Coronel et al., "Dengue Vaccine Booster in healthy Adolescents and Adults in Latin America: Evaluation 4-5 Years After a Primary 3-Dose Schedule"; The Pediatric Infectious Disease journal, May 1, 2019, 38(5):e90-e95; https://doi.org/10.1097/inf.0000000000002286.

clinicaltrials.gov—Immunogenicity and Safety of a Tetravalent Dengue Vaccine Booster Injection in Subjects Who Previously Completed a 3-dose Schedule—https://clinicaltrials.gov/ct2/show/study/NCT02824198, (2019).

clinicaltrials.gov—Study of a Booster Dose of a Tetravalent Dengue Vaccine in Subjects Who Previously Completed the 3-dose Schedule—https://clinicaltrials.gov/ct2/show/NCT02623725, (2019).

Diazgranados et al., "CYD-TDV dengue vaccine performance by baseline immune profile (monotypic/multitypic) in dengue seropositive individuals"; Clinical Infectious Diseases, ciaa304; https://doi.org/10.1093/cid/ciaa304, (2020).

George et al., "Safety and Immunogenicity of a Live Attenuated Tetravalent Dengue Vaccine Candidate in Flavivirus-Naive Adults: A Randomized, Double-Blinded Phase 1 Clinical Trial", Journal of Infectious Diseases, JID, vol. 212, No. 7, Mar. 19, 2015, pp. 1032-1041.

Rupp et al., "Safety and immunogenicity of different doses and schedules of a live attenuated tetravalent dengue Vaccine (TDV) in healthy adults: A Phase 1b randomized study", Vaccine, vol. 33, No. 46, Nov. 1, 2015, pp. 6351-6359.

Osorio et al., "A recombinant, chimeric tetravalent dengue vaccine candidate based on a dengue virus serotype 2 backbone", Expert Review of Vaccines, vol. 15, No. 4, Apr. 2, 2016, pp. 497-508.

Guy et al., "From research to phase III: Preclinical, industrial and clinical development of the Sanofi Pasteur tetravalent dengue vaccine", Vaccine, vol. 29, No. 42, Sep. 1, 2011, pp. 7229-7241.

Kirkpatrick et al., "The live attenuated dengue vaccine TV003 elicits complete protection against dengue in a human challenge model", Science GTranslational Medicine, vol. 8, No. 330, Mar. 16, 2016, pp. 330ra36-330ra36.

Saez-Llorens et al., "Safety and immunogenicity of one versus two doses of Takeda's tetravalent dengue vaccine in children in Asia and Latin America: interim results from a phase 2, randomised, placebo-controlled study", Lancet Infectious Diseases, Elsevier Ltd, US, vol. 17, No. 6, Mar. 30, 2017, pp. 615-625.

King et al., "Simultaneous administration of childhood vaccines: An important public health policy that is safe and efficacious", Pediatric Infectious Disease Jour, Lippincott Williams & Wilkins, US, vol. 13, No. 5, Jan. 1, 1994, pp. 394-407.

Chokephaibulkit, "Combination Vaccines", Chot Mai Het Thang Phaet—Journal of the Medical Association of Thai, medical Association of Thailand, TH, vol. 85, No. Suppl. 2, Aug. 1, 2002, pp. S694-S699.

Osorio et al., "Development of DENVax: A chimeric dengue-2 PDK-53-based tetravalent vaccine for protection against dengue fever", Vaccine, vol. 29, No. 42, Jul. 11, 2011, pp. 7251-7260.

Wilder-Smith et al., "Age specific differences in efficacy and safety for the CYD-tetravalent dengue vaccine", Expert Review of Vaccines, vol. 15, No. 4, Apr. 2, 2016, pp. 437-441.

Dubey et al., "Immunogenicity and safety of a tetravalent dengue vaccine in healthy adults in india: A randomized, observer-blind, placebo-controlled phase II trial", Human Vaccines and immunotherapeutics, vol. 12, No. 2, Aug. 20, 2015, pp. 512-1518.

Sirivichayakul et al., "Safety and Immunogenicity of a Tetravalent Dengue Vaccine Candidate in Healthy Children and Adults in Dengue-Endemic Regions: A Randomized, placebo-Controlled Phase 2 Study", Journal of infectious Diseases, JID, vol. 213, No. 10, Dec. 23, 2015, pp. 1562-1572.

Wichmann et al., "Live-attenuated tetravalent dengue vaccines: The needs and challenges of post-licensure evaluation of vaccine safety and effectiveness", Vaccine, vol. 35, No. 42, Oct. 1, 2017, pp. 5535-5542.

Sabchareon et al., "Safety and immunogenicity of tetravalent live-attenuated dengue vaccines in Thai adult olunteers: Role of serotype concentration, ratio, and multiple doses", American Journal of

(56) References Cited

OTHER PUBLICATIONS

Tropical Medicine & Hygiene, American Society of Tropical Medicine and Hygiene, US, vol. 66, No. 3, Mar. 1, 2002, pp. 264-272.
International Search Report dated Jan. 3, 2019 for International Application No. PCT/IB2018/001219, 5 pages.
Dayan et al., "Immunogenicity and Safety of a Recombinant Tetravalent Dengue Vaccine in Children and Adolescents Ages 9-16 Years in Brazil," Am. J. Trop. Med. Hyg., 80(6), 2013, pp. 1058-1065; https://222.ncbi.nlm.nih.gov/pmc/articles/PMC3854882/pdf/tropmed-28-1058.pdf.
Dayan et al., "Efficacy after 1 and 2 doses of CYD-TDV in dengue endemic areas by dengue serostatus", Vaccine 38 (2020) 6472-6477.
Coronel et al., "Immune Response Persistence and Safety of a Booster Dose of the Tetravalent Dengue Vaccine in Adolescents and Adults Who Previously Completed the 3-dose Schedule 4-5 Years Earlier in Latin America", The Pediatric Infectious Disease Journal, vol. 39, No. 10, Oct. 2020, pp. 961-968.
Coronel et al., "CYD-TDV Dengue Vaccine: Alternative Vaccination Schedules with Reduced Number of Doses in Healthy Individuals Aged 9 to 50 Years in Latin America and Asia-Pacific Regions", ASTMH Poster, published Nov. 2020).
Rabaa et al., "Genetic epidemiology of dengue viruses in phase III trials for the CYD tetravalent dengue vaccine and implications for efficacy." eLife 6:e24196 https://doi.org/10.7554/eLife.24196.001, (2017).
World Health Organization (WHO), "Guidelines on the Quality, Safety and Efficacy of Dengue Tetravalent Vaccines (Live, Attenuated)," Proposed replacement of TRS 932, Annex 1. WHO Press, Geneva, Switzerland, May 1, 2011 https://www.who.int/biologicals/areas/vaccines/dengue/WHO_DRAFT_Den_24May2011.pdf.
Guy et al, "Development of sanofi pasteur tetravalent dengue vaccine", Human Vaccines, 6:9, 696-705 (2010).
Poo et al, "Live-attenuated Tetravalent Dengue Vaccine in Dengue-naive Children, Adolescents, and Adults in Mexico City—Randomized Controlled Phase 1 Trial of Safety and Immunogenicity", The Pediatric Infectious Disease Journal, vol. 30, No. 1, Jan. 2011, pp. 1-9.
Lanata et al, "Immunogenicity and safety of tetravalent dengue vaccine in 2-11 year-olds previously vaccinated against yellow fever: Randomized, controlled, phase II study in Piura,I Peru", Vaccine 30 (2012) 5935-5941, https//doi.org/10.1016/j.vaccine.2012.07.043.
Guy et al, "A recombinant live attenuated tetravalent vaccine for the prevention of dengue", Expert Review of Vaccines, 2017, vol. 16, No. 7, 1-13.doi:10.1080/14760584.2017.1335201. Epub Jun. 7, 2017.Review.Erratum in: Expert Rev Vaccines.Jul. 2017;16/(7):ix.
Sabchareon et al, "Protective efficacy of the recombinant, live-attenuated, CYD tetravalent dengue vaccine in Thai schoolchildren: a randomised, controlled phase 2b trial", Lancet, 2012, 380:1559-67.
World Health Organization, Immunization, Vaccines and Biologicals: Questions and Answers on Dengue Vaccines http://www.who.int/immunization/research/development/dengue_q_and_a/en/, (2018).
Blaney et al., "Recombinant, Live-Attenuated Tetravalent Dengue Virus Vaccine Formulations Induce a Balanced, Broad, and Protective Neutralizing Antibody Response against Each of the Four Serotypes in Rhesus Monkeys"; Journal of Virology, (2005), vol. 79(9), p. 5516-5528; https://doi.org/10.1128/JVI.79.9.5516-5528.2005 (published May 2005).
Park et al, Immunogenicity and safety of a dengue vaccine given as a booster in Singapore: a randomized Phase II, placebo-controlled trial evaluating its effects 5-6 years after completion of the primary series; Human Vaccines & Immunotherapeutics; 2020, vol. 16, No. 3, 523-529; https://doi.org/10.1080/21645515.2019.1661204 (published Nov. 5, 2019).
Limkittikul et al, Long-term safety follow-up of children from a randomized controlled phase IIb proof of concept efficacy study of the live attenuated tetravalent dengue vaccine (CYD-TDV) in Thailand; Asian Pacific Journal of Tropical Medicine 2019; vol. 12(9); p. 396-403; https://doi.org/10.4103/1995-7645.267582 (published Sep. 30, 2019).
Reynales et al, Secondary Analysis of the Efficacy and Safety Trial Data of the Tetravalent Dengue Vaccine in Children and Adolescents in Colombia; The Pediatric Infectious Disease Journal (2020), vol. 39(4), p. e30-e36; https://doi.org/10.1097/INF.0000000000002580 (published Apr. 2020).
Carpp et al, Microneutralization assay titer correlates analysis in two Phase 3 trials of the CYD-TDV tetravalent dengue vaccine in Asia and Latin America; PLoS ONE (2020), vol. 15(6); https://doi.org/10.1371/journal.pone.0234236 (published Jun. 15, 2020).
Durbin et al., "A Single Dose of Any of Four Different Live Attenuated Tetravalent Dengue Vaccines is Safe and immunogenic in Flavivirus-Naive Adults: A Randomized, Double-Blind Clinical Trial," J Infect Dis., 207(6): 957-965 Mar. 15, 2013). https://doi.org/10.1093/infdis/jis936 (published Jan. 17, 2013).
Durbin et al., "Next-generation dengue vaccines: novel strategies currently under development",—Viruses, 3(10), pp. 1800-1814 (E-pub Sep. 26, 2011). https://doi.org/10.3390/v3101800 (published Sep. 26, 2011).
George, S.L., "Prospects for a Dengue Vaccine: Progress and Pitfalls," Missouri Medicine, 111(4): 337-342 (Jul./Aug. 2014). https://pubmed.ncbi.nlm.nih.gov/25211865/ (published Jul.-Aug. 2014).
Gilbert, Peter B. et al. "Bridging Efficacy of a Tetravalent Dengue Vaccine from Children/Adolescents to Adults in Highly Endemic Countries Based on Neutralizing Antibody Response" American Journal of Tropical Medicine and Hygiene (2019) vol. 101(1), pp. 164-179. https://doi.org/10.4269/ajtmh.18-0534 (published May 20, 2019).
Guy et al, "Cell-mediated immunity induced by chimeric tetravalent dengue vaccine in naive or flavivirus-primed subjects," Vaccine. 26(45):5712-21 (2008). https://doi.org/10.1016/j.vaccine.2008.08.019.
Houlton, "Sanofi Ordered to Pull Dengue Vaccine" Chemistry World, 3 Pages, Dec. 15, 2017. https://www.chemistryworld.com/news/sanofi-ordered-to-pull-dengue-vaccine/3008436.article.
Kirstein, Judith et al. "Immunogenicity of the CYD tetravalent dengue vaccine using an accelerated schedule: randomised phase II study in US adults" BMC Infection Diseases (2018) vol. 18(475) 11 pages. https://doi.org/10.1186/s12879-018-3389-x (published Sep. 21, 2018).
Roehrig, "Current status of dengue vaccine development," SAGE/Immunization Meeting, Apr. 2013. https://docplayer.net/21438920-Current-status-of-dengue-vaccine-development.html.
Sridhar et al., "Effect of Dengue Serostatus on Dengue Vaccine Safety and Efficacy" New England Journal of Medicine, published Jun. 13, 2018 at NEJM.org; https:doi.org/10.1056/NEJMoa1800820 (published Jul. 26, 2018).
Tran et al, "Long-term immunogenicity and safety of tetravalent dengue vaccine (CYD-TDV) in healthy populations in Singapore and Vietnam: 4-year follow-up of randomized, controlled, phase II trials"; Human Vaccines & Immunotherapeutics (2019); vol. 15(10); p. 2315-2327; https://doi.org/10.1080/21645515.2019.1578595.
Arredondo-Garcia et al., "Four-year safety follow-up of the tetravalent dengue vaccine efficacy randomized controlled trials in Asia and Latin America"; Clinical Microbiology & Infection (2018), vol. 24(7), p. 755-763; https://doi.org/10.1016/j.cmi.2018.01.018.
Guy et al, "Dengue vaccine: hypotheses to understand CYD-TDV-induced protection", Nat Rev Microbiol. Jan. 2016;14(1):45-54. doi: 10.1038/nrmicro.2015.2. Epub Dec. 7, 2015. Review.
Gailhardou et al, Safety Overview of a Recombinant Live-Attenuated Tetravalent Dengue Vaccine: Pooled Analysis of Data from 18 Clinical Trials. PLoS Negl Trop Dis. Jul. 14, 2016;10(7):e0004821. doi: 10.1371/journal.ontd.0004821. eCollection Jul. 2016.
Vigne et al, "Integrated immunogenicity analysis of a tetravalent dengue vaccine up to 4 y after vaccination", Hum Vaccin Immunot Sep. 2, 2017;13(9):2004-2016. doi: 10.1080/21645515.2017.1333211. Epub Jun. 9, 2017.
Olivera-Botello et al, "CYD-TDV Vaccine Trial Group. Tetravalent Dengue Vaccine Reduces Symptomatic and Asymptomatic Dengue Virus Infections in Healthy Children and Adolescents Aged 2-16

(56) References Cited

OTHER PUBLICATIONS

Years in Asia and Latin America", J Infect Dis., Oct. 1, 2016, 214(7):994-1000, doi: 10.1093/infdis/jiw297. Epub Jul. 14, 2016.
Coudeville L et al, "Potential impact of dengue vaccination: Insights from two large-scale phase III trials with a tetravalent dengue vaccine", Vaccine, Dec. 7, 2016, 34(50):6426-6435, doi: 10.1016/j.vaccine.2016.08.050. Epub Sep. 3, 2016.
Study of a Novel Tetravalent Dengue Vaccine in Healthy Children Aged 2 to 14 Years in Asia; ClinicalTrials.gov identifier: NCT01373281; see Study Details, Tabular View & Study Results; https://clinicaltrials.gov/ct2/show/record/NCT01373281, (2018).
Study of a Novel Tetravalent Dengue Vaccine in Healthy Children and Adolescents Aged 9 to 16 Years in Latin America; ClinicalTrials.gov identifier: NCT01374516; see Study Details, Tabular View & Study Results; https://clinicaltrials.gov/ct2/show/NCT01374516, (2019).
clinicaltrials.gov Efficacy and safety of dengue vaccine in healthy children, see Study Details, Tabular View & Study Results; https://clinicaltrials.gov/ct2/show/NCT00842530, (2019).
Twiddy et al., "Phylogenetic relationships and differential selection pressures among genotypes of dengue-2 virus," Virology. 298(1):63-72 (2002) https://doi.org/10.1006/viro.2002.1447.
Deauvieau et al., "Innate immune responses in human dendritic cells upon infection by chimeric yellow-fever dengue vaccine serotypes 1-4," Am J Trap Med Hyq. 76(1):144-54 (2007).
Delangel et al, "Dengue Vaccines: Strong Sought but Not a Reality Just Yet" PLOS 9(10): 61003551 (2013).
Dorigatti et al. "Refined efficacy estimates of the Sanofi Pasteur dengue vaccine CYD-TDV using machine learning", NatCommun 2018; 9: 3644; https://dx.doi.org/10.1038%2Fs41467-018-06006-6.
Hadinegoro et al., "Efficacy and Long-Term Safety of a Dengue Vaccine in Regions of Endemic Disease," N Engl J Med. 373(13):1195-206 (2015) https://doi.org/10.1056/nejmoa1506223.
Moodie et al, "Neutralizing Antibody Correlates Analysis of Tetravalent Dengue Vaccine Efficacy Trials in Asia and Latin America," The Journal of Infectious Diseases 217: 742-753 (2018) https://doi.org/10.1093/infdis/jix609.
Morrison et al., "A novel tetravalent dengue vaccine is well tolerated and immunogenic against all 4 serotypes in flavivirus-naive adults," J Infect Dis. 201 (3):370-7 (2010) https://doi.org/10.1086/649916.
Osorio et al., "Development of DENVax: a chimeric dengue-2 PDK-53-based tetravalent vaccine for protection against dengue fever," Vaccine. 29(42):7251-60 (2011) https://www.ncbi.nlm.nih.gov/pmc/articles/PMC4592106/pdf/nihms724192.pdf.
Anderson et al., "Interference and Facilitation Between Dengue Serotypes in a Tetravalent Live Dengue Virus Vaccine Candidate", Journal of Infectious Diseases, vol. 204, No. 3, (Aug. 1, 2011) pp. 442-450; https://doi.org/10.1093/infdis/jir279 (published Aug. 2011).
Guy et al., Immunogenicity of Sanofi Pasteur tetravalent dengue vaccine; Journal of Clinical Virology, vol. 46, Oct. 1, 2009, pp. S16-S19 (cited on EPO Office Action dated May 14, 2020 on the EP equivalent of related U.S. Appl. No. 16/123,319).
Da Costa et al., Safety, immunogenicity and efficacy of a recombinant tetravelent dengue vaccine: A meta-analysis of randomized trials; Vaccine (2014), vol. 32(39), p. 4885-4892; https://doi.org/10.1016/j.vaccine.2014.07.008.
Guirakhoo et al., "Safety and efficacy of chimeric yellow Fever-dengue virus tetravalent vaccine formulations in non-human primates", J.Virol., 78(9), pp. 4761-4775 (May 2004), https://doi.org/10.1128/FVI.78.9.4761-4775.2004.
Crevat et al., "Safety and Immunogenicity of a Tetravalent Dengue Vaccine in Flavivirus-Naive and -Immune pediatric Populations with Two Vaccination Regimens", Abstract 395 from american journal of Tropical medicine & Hygiene, vol. 81, 5(1), Nov. 1, 2009, p. 113.
Dayan et al., "Assessment of the long-term efficacy of a dengue vaccine against symptomatic, virologically-confirmed dengue disease by baseline dengue serostatus", Vaccine, 38(19), pp. 3531-3536; https://doi.org/10.1016/j.vaccine,2020.03.029.
Capeding et al., "Live-attenuated, tetravalent dengue vaccine in children, adolescents and adults in a dengue endemic country: randomized controlled phase I trial in the Philippines," Vaccine, 29(22):3863-72 (2011) https://doi.org/10.1016/j.vaccine.2011.03.057.
Osorio et al., "Safety and immunogenicity of a recombinant live attenuated tetravalent dengue vaccine (DENVax) in flavivirus-naive healthy adults in Colombia: a randomised, placebo-controlled, phase 1 study", Lancet Infect Dis., Sep. 2014, 14(9):830-838.
Mandavdhare et al., Medical Journal of Dr. Dy Patil University, vol. 9, Issue 5, Sep.-Oct. 2016, 3 pages.
Hadinegoro et al., "Efficacy and Long-Term Safety of a Dengue Vaccine in Regions of Endemic Disease", The New England Journal of medicine, Sep. 24, 2015, vol. 373, No. 13, 40 pages.
Villar, Luis A. et al. "Safety and Immunogenicity of a Recombinant Tetravalent Dengue Vaccine in 9-19 years olds" The Pediatric Infectious Disease Journal (2013) vol. 32(10), pp. 1102-1109.

* cited by examiner

SEQUENCE LISTING

<160> NUMBER OF SEQ ID NOS: 7

<210> SEQ ID NO 1
<211> LENGTH: 1983
<212> TYPE: RNA
<213> ORGANISM: Artificial Sequence
<220> FEATURE:
<223> OTHER INFORMATION: CYD1 prME

<400> SEQUENCE: 1

```
uuucaucuga ccacacgagg gggagagccg cauaugauag uuaccaagca ggaaagagga      60
aagucacuuu uguuuaagac cucagcuggu gucaacaugu gcacccuuau ugcgauggau     120
uuggagagu auguagga uacaaugacu acaaauguc cucgaaucac ugaggcggaa         180
ccagaugacg uugauuguug gugcaaugcc acagacacau gggugaccua uggaacgugu     240
ucccaaacug gcgagcaccg acgagacaaa cguuccgucg cacuggcccc acacgugga     300
cuuggucuag aaacaagaac cgaaacgugg augccucucu aaggcgcuug gaaacaaaua    360
caaagagugg agacuugggc ccugagacac ccaggauuca cagugauagc ccuuuucua     420
gcacaugcca uaggaacauc caucacccag aaagggauua uuuucauuuu guugaugcug   480
guaacaccau ccauggccau gcgaugugug ggaauaggca acagggacuu cguggaagga   540
cugucaggag caacgugggu agaugugggua cuggaacaug gaaguugcgu caccaccaug   600
gcaaaagaua aaccaacauu ggacauugaa cucuugaaga cggaagucac aaacccugcc   660
guccuucgaa aacugugcau cgaagcuaaa auaucaaaca ccaccaccga uucaagaugc   720
ccaacacaag gagaagccac acugguggaa gagcaagacg cgaauuuugu gugucgacga    780
acguuugugg acagaggcug gggcaauggc uguggggcucu ucggaaaagg uagccuaaua   840
acgugugcua aguucaagug ugugacaaaa cuggaaggaa agauaguuca auaugaaaac     900
uugaaauauu caguaauagu caccgucc ac acuggagacc agcaccaggu gggaaaugaa    960
agcacagaac augggacaac agcaacuaua acaccucaag cucccacguc ggaaauacag   1020
cugaccgacu acggagcucu aacauuggau ugcucaccua gaacaggacu agacuucaau    1080
gaaaugguu uguugacaau gaaagaaaga ucauggcuag uccacaaaca augguuucua    1140
gaccuaccac ugccuuggac cucgggagcu acaacgucac aagagacuug gaacagacaa   1200
gauuugcugg uaacauuuaa gacagcucau gcaaagaagc aggaaguagu cguacuagga   1260
ucacaagaag gagcaaugca cacugcguug accggagcga cagaaaucca aacgucugga   1320
acgacaacaa uuuuugcagg acacuugaaa uguagacuaa aaauggacaa acugacucua   1380
aaagggaugu cauaugugau gugcacaggc ucauucaagc uagagaaaga gguggcugag   1440
acccagcaug gaaccguucu agugcagguu aaauacgaag gaacagaugc accaugcaag   1500
aucccuuuuu cgacccaaga ugaaaaagga guaaccagag augggagagu gauaacagcc   1560
aacccuauag ucacugacaa ggaaaaacca gucaacauug aggcagaacc accuuuuggu   1620
gagaguuaca ucguggu agg agcaggugaa aaagcuuuga acuaagcug guucaagaaa    1680
ggaagcacca uagggaaaau guuugaggca acugcccgag gagcacgaag gauggccaua    1740
cuggagaca ccgcauggga cuuugguucu auaggaggag uguucacauc uguuggaaaa   1800
cuaguacacc agauuuuugg aacugcauau ggaguuuugu cagcggugu uccuggacc    1860
augaaaauag gaauaggggu ucugcugaca uggcuaggau uaaacucaag gagcacgucc    1920
cuuucgauga cgugcauugc aguuggccug guaacacugu accuaggagu caugguuggc    1980
gcc                                                                  1983
```

<210> SEQ ID NO 2
<211> LENGTH: 1983
<212> TYPE: RNA
<213> ORGANISM: Artificial Sequence
<220> FEATURE:
<223> OTHER INFORMATION: CYD2 prME

<400> SEQUENCE: 2

| | | | | | |
|---|---|---|---|---|---|
| uuccaucuaa | ccacacguaa | cggagaacca | cacaugaucg | ucaguagaca | agagaaaggg | 60 |
| aaaagucuug | uguuuaaaac | agaggauggc | gugaacaugu | gcacccucau | ggccauggac | 120 |
| cuuggugaau | ugugugaaga | cacaaucacg | uacaaguguc | cccuucucag | gcagaaugag | 180 |
| ccagaagaca | uagacugcug | gugcaacucc | acguccacgu | ggguaaccua | ugggacuugu | 240 |
| accaccacgg | gagaacauag | aagagaaaaa | agaucagugg | cacucguucc | acauguggga | 300 |
| augggacugg | agacgcgaac | ugaaacaugg | augucaucag | aaggggcuug | gaaacaugcc | 360 |
| cagagaauug | aaauuuggau | ccugagacau | ccaggcuuca | ccauaauggc | agcaauccug | 420 |
| gcauacacca | uagggacgac | acauuuccag | agagcacuga | uuucaucuu | acugacagcu | 480 |
| gucgcuccuu | caaugacaau | gcguugcaua | ggaauaucaa | auagagacuu | guagaaaggg | 540 |
| guuucaggag | gaagcugggu | ugacauaguc | uuagaacaug | gaagcugugu | gacgacgaug | 600 |
| gcaaaaaaca | aaccaacauu | ggauuuugaa | cugauaaaaa | cagaagccaa | acagccugcc | 660 |
| acccuaagga | aguacuguau | agaggcaaag | cuaaccaaca | caacaacaga | aucucguugc | 720 |
| ccaacacaag | gggaacccag | ccuaaaugaa | gagcaggaua | aaagguucgu | cugcaaacac | 780 |
| uccaugguag | acagaggaug | gggaaaugga | uggauuau | uuggaaaggg | aggcauugug | 840 |
| accugugcua | uguucacaug | caaaaagaac | auggagggaa | aaguugugca | gccagaaaac | 900 |
| uuggaauaca | ccauuguggu | aacaccccac | ucaggggaag | agcaugcggu | cggaaaugac | 960 |
| acaggaaaac | auggcaagga | aaucaaagua | acaccacaga | guuccaucac | agaagcagaa | 1020 |
| uugacagguu | auggcacugu | cacgauggag | ugcucuccga | gaacaggccu | cgacuucaau | 1080 |
| gagauggugu | ugcugcagau | ggaaaauaaa | gcuuggcugg | ugcauaggca | augguuccua | 1140 |
| gaccugccgu | uaccauggcu | gcccggagcg | gacacacaag | ggucaaauug | gauacaaaaa | 1200 |
| gaaacauugg | ucacuuucaa | aaauccucau | gcgaagaaac | aggauguuuu | uguuuuagga | 1260 |
| ucccaagaag | gggccaugca | cacagcacuc | acagggccca | cagaauccca | aaugucauca | 1320 |
| ggaaacuuac | ucuucacagg | acaucucaag | ugcaggcuga | gauggacaa | gcuacagcuc | 1380 |
| aaaggaaugu | cauacucuau | gugcacagga | aaguuuaaag | uugugaagga | auagcagaaa | 1440 |
| acacaacaug | gaacaauagu | uaucaggguu | caguaugaag | gggacggcuc | uccauguaaa | 1500 |
| aucccuuuug | agauaaugga | uuggaaaaa | agacaugucu | uaggucgccu | gaucacaguc | 1560 |
| aacccaauug | ugacagaaaa | agauagccca | gucaacauag | aagcagaacc | uccauucgga | 1620 |
| gacagcuaca | ucaucauagg | aguagagccg | ggacaacuga | agcucaacug | guuuaagaaa | 1680 |
| ggaaguucua | ucggccaaau | guugagaca | acaaugaggg | gggcgaagag | aaauggccauu | 1740 |
| uuggugugaca | cagccuggga | uuuuggauuc | cugggaggag | uguuuacauc | uauaggaaaa | 1800 |
| gcccuccacc | aagucuuugg | agcaaucuau | ggagcugccu | ucagggggu | cucauggacu | 1860 |
| augaaaaucc | ucauaggagu | cauuaucaca | uggauaggaa | ugaauucacg | cagcaccuca | 1920 |
| cugucugugu | cacuaguauu | gguggagguc | gugacgcugu | auuuggagu | uaugguggc | 1980 |
| gcc | | | | | | 1983 |

<210> SEQ ID NO 3
<211> LENGTH: 1977
<212> TYPE: RNA
<213> ORGANISM: Artificial Sequence
<220> FEATURE:
<223> OTHER INFORMATION: CYD3 prME

<400> SEQUENCE: 3

| | |
|---|---|
| uuccacuuaa cuucacgaga uggagagccg cgcaugauug uggggaagaa ugaaagaggg | 60 |
| aaaucccuac uuuuuaagac agcuucugga aucaacaugu gcacacucau agccauggac | 120 |
| uugggagaga ugugugauga cacggucacu uacaaaugcc cccucauugc cgaaguggaa | 180 |
| ccugaagaca uugacugcug gugcaaccuu acaucgacau gggugacuua uggaacgugc | 240 |
| aaucaagcug gggagcauag acgcacaaag agaucagugg cguuagcucc ccaugucggc | 300 |
| augggacugg acacacgcac ccaaaccugg augucggcug aaggagcuug agacaaguc | 360 |
| gagaagguag agacauggc ucuuaggcac ccagggucua ccauacuagc ucuauuucuu | 420 |
| gcucauuaca uaggcacuuc ccugacccag aaagugguua uuuuauacu acuaaugcug | 480 |
| gucacuccau ccauggcaau gagaugcgug ggaguaggaa acagagauu uguggaaggu | 540 |
| cugucgggag cuacguggu ugaugugug cuggagcacg gugggugugu gaccaccaug | 600 |
| gcuaagaaca agccuacgcu ggacauagag cuucagaaga ccgaggccac ccaacuggcg | 660 |
| acccuucgaa aguuaugcau ugagggaaaa auuaccaaca uaacaacuga cucaaggugu | 720 |
| ccuacccagg gggaagcgau uuaccugag gagcaggacc agaacuacgu auguaagcac | 780 |
| acauaugugg auagaggcug gggaaacggu ugugguuugu uggaaaagg aagcuuggug | 840 |
| acaugcgcga aauuucaaug ucuagaauca auagaggaa aaguggugca acaugagaac | 900 |
| cucaaauaca cugucaucau uacagugcac acaggaaacc aacaccaggu gggaaaugac | 960 |
| acgcagggag ucacggcuga gauaacaccc caggcaucaa ccguugaagc caucuugccu | 1020 |
| gaauauggaa cccuugggcu agaaugcuca ccacggacag guuggauuu caugaaaug | 1080 |
| auuuuauuga caaugaaaaa caagcaugg augguacaua ggcaaugguu cuugaccua | 1140 |
| cccuaccau ggacaucagg agcuacaaca gagacaccaa cuggaacag aaagagcuu | 1200 |
| cuugugacau ucaaaaaugc acaugcaaaa agcaagaag uaguugccu uggaucgcaa | 1260 |
| gagggagcaa ugcacacagc gcugacagga gcuacagaga uccaaaacuc aggagguaca | 1320 |
| agcauuuuug cggggcacuu gaaaugugaa cuuaagaugg acaaauugga acucaagggg | 1380 |
| augagcuaug caaugugcuu gaauaccuuu guguugaaga agaagucuc cgaaacgcag | 1440 |
| cauggcacaa uacucauuaa gguugaguac aaagggggaag augcaccuug caagauuccu | 1500 |
| uucuccacag aggauggaca agggaaagcu cacaauggua gacugaucac agccaaccca | 1560 |
| guggugacca agaaggagga gccugucaac auugaggcug aaccuccuuu uggggaaagu | 1620 |
| aacauaguga uuggaauugg agacaaagcc uugaaaauua acuggacaa gaagggaagc | 1680 |
| ucgauuggga agauguucga ggccacugcc agagugcaa ggcgcauggc caucuuggga | 1740 |
| gacacagccu gggacuuugg aucagugggu gguguucuaa auucauuagg gaaaugguug | 1800 |
| caccaaauau ucggaagugc uuacacagcc cguuuagug gagucucaug gauaaugaaa | 1860 |
| auuggaauag uguccucuu aaccuggaua gggguugaauu caaaaaacac uuccaugca | 1920 |
| uuuucaugcg uugcgauagg aauuaucaca cucuaucugg gagccguggu acaggcc | 1977 |

<210> SEQ ID NO 4
<211> LENGTH: 1983

<212> TYPE: RNA
<213> ORGANISM: Artificial Sequence
<220> FEATURE:
<223> OTHER INFORMATION: CYD4 prME

<400> SEQUENCE: 4

```
uucaccugu caacaagaga cggcgaaccc cucaugauag uggcaaaaca cgaaaggggg      60
agaccucucu uguuuaagac aacagaggga aucaacaaau gcacucuuau ugccauggac    120
cugggugaaa ugugugaaga cacuguuacg uauaaaugcc cucuacuggu uaacaccgaa    180
ccugaagaca uugauugcug gugcaaucuc acguccaccu gggucaugua cgggacaugu    240
acccagagcg gagaacggag acgagagaag cgcucaguag cuuuaacacc acauucagga    300
augggauugg aaacaagagc ugagacaugg augucaucgg aaggggcuug gaaacaugcu    360
caaagaguag aaagcuggau acucagaaac ccaggauucg cgcucuuggc aggauuuaug    420
gcuuacauga uugggcaaac aggaauucag cgaacugucu ucuuugcccu aaugaugcug    480
gucgccccau ccuacggaau gcgaugcgua ggaguaggga acagagacuu guggaagga    540
gucucgggug gagcaugggu cgaccuggug cuggaacaug gaggaugcgu cacaaccaug    600
gcccagggaa aaccaaccuu ggauuuugaa cugaccaaga caacagccaa ggaaguggcu    660
cuacuucgaa ccuauugcau ugaagccucg auaucaaaca uaaccacggc aacaagaugu    720
ccaacgcaag gagagccuua ucucaaagag gaacaagacc aacaguacau ugccggaga    780
gaugugguag acagagggug gggcaauggc uggcuuau uggaaaagg aggaguugug    840
acaugugcga aguuuuaug cucggggaag auaacaggca aucggucca aauugaaaac    900
cuugaauaua caguguugu gacaguccac aauggagaca cccaugcagu aggaaaugac    960
acaucuaauc auggagugac agccacgaua acucccaggu caccaucggu agaaguuaaa   1020
uugccggacu auggagaacu aacacucgau ugugaaccca gguccggaau ugauucaau    1080
gagaugauuc ugaugaaaau gaaaagaaa acguggcuug ugcauaagca augguuuug    1140
gaccuaccuc uaccauggac agcaggagca gacacaucag aagccauug gaauuacaa    1200
gagagaaugg ugacauucaa gguuccucau gccaagagac aggaugugac agugcuagga   1260
ucucaggagg gagcuaugca uucugcccuc gccggagcca cagaagugga uuccggugau   1320
ggaaaucaca uguuugcagg acaucucaag gcaaagucc guaaggagaa auugagaauu   1380
aaaggaaugu cauacacaau guuucagga aaguucucaa ugacaaaga gauggcagaa   1440
acacagcaug ggacaacagu ggugaaaguc aaguaugaag gcgcuggagc uccguguaaa   1500
gucccaua agauaagaga ugacaagaa gaaaaguggu uggcgcau caucucaucu    1560
accccuuug cugagaauac caacagcgua ccaacauag aauuagaacc cccuuuggg    1620
gacaguuaca uagugauagg uguuggagau agucauuaa cacuccauug guucaggaaa   1680
ggagcuccaa uuggcaagau guuugaguc acauacagag gugcaaaacg aauggccauu   1740
cuaggugaaa cagcuuggga uuuugguucu guugguggaa uguucacauc acugggaaag   1800
gcuguacacc agguuuuugg aaguguguau acaaccaugu uggaggggu cucauggaug   1860
guuagaauc uaauugggu cuuaguauug uggauuggca cgaauucaag aaacacuuca   1920
auggcaauga cgugcauagc uguuggagga aucacucugu uucuagguuu cacaguuggc   1980
gcc                                                                1983
```

<210> SEQ ID NO 5
<211> LENGTH: 1983
<212> TYPE: RNA

<213> ORGANISM: Artificial Sequence
<220> FEATURE:
<223> OTHER INFORMATION: CYD2V prME

<400> SEQUENCE: 5

```
uuccauuuaa ccacacgaaa uggagaacca cacaugaucg uuggcagaca agagaaaggg      60
aaaagccuuc uguuuaaaac agaggauggu gugaacaugu guacccucau ggccauugau     120
cuuggugaau ugugugaaga uacaaucacg uacaagugcc cccuccucag gcagaaugaa     180
ccagaagaua uagauuguug gugcaacucc acguccacau ggguaacuua ugggacugu      240
accaccacag gagaacacag aagagaaaaa agaucagugg cacucguucc acaugugggu     300
augggacugg agacacgaac ugaaacaugg augucgucag aaggggccug gaaacacgcu     360
cagagaauug aaacuuggau cuugagacau ccaggcuuua ccauaauggc agcaauccug     420
gcauauaccg uaggaacgac acauuuccaa agggcccuga uuuucaucuu acuggcagcu     480
gucgcuccuu caaugacaau gcguugcaua ggaauaucaa auagagacuu guagaaggg     540
guuucaggag gaagcugggu ugacauaguc uuagaacaug gaaguugugu gacgacaaug     600
gcaaaaaaua aaccaacacu ggauuuugaa cugauaaaaa cagaagccaa acaaccugcc     660
acucuaagga aguacuguau agaggcaaag cugaccaaua caacaacaga aucucguugc     720
ccaacacaag gggaacccag ucuaaaugaa gagcaggaca aagguucgu cugcaaacac     780
uccaugguag acagaggaug ggggaaaugga uguggauuau uggaaagggg aggcauugug     840
accugugcua uguucacaug caaaaagaac auggaaggaa aaaucgugca accagaaaau     900
uuggaauaca ccaucgugau aacaccucac ucaggagaag agcacgcugu agguaaugac     960
acaggaaaac augguaagga aauuaaaaua acaccacaga guuccaucac agaagcagaa    1020
cugacaggcu auggcacagu cacgauggag ugcucuccga aacgggccu ugacuucaau    1080
gagauggugc ugcugcagau ggaagauaaa gcuuggcugg ugcacaggca augguuccua    1140
gaccugccgu uaccauggcu acccggagcg gacacaagg aucaaauug gauacagaaa    1200
gagacauugg ucacuuucaa aaauccccac gcgaagaagc aggaugucgu uguuuagga    1260
ucucaagaag gagccaugca cacggcacuc acaggggcca cagaaauccca gaugucauca    1320
ggaaacuuac uauucacagg acaucucaaa ugcaggcuga aauggacaa acuacagcuc    1380
aaaggaaugu cauacucuau guguacagga aaguuuaaaa uugugaagga auagcagaa    1440
acacaacaug gaacaauagu uaucagagua caauaugaag gagacggcuc uccauguaag    1500
aucccuuuug aaauaaugga uuuggaaaaa agacaugucu uaggucgccu gauuacaguu    1560
aauccgaucg uaacagaaaa agauagccca gucaacauag aagcagaacc uccauucgga    1620
gacagcuaca ucauuauagg aguagagccg ggacaauuga acucaacug guucaagaaa    1680
ggaaguucca ucggccaaau guuugagacg acaaugagag agcaaagag aauggccauu    1740
uuaggugaca cagccuggga uuuuggaucu cuggaggag uguuacauc uauaggaaag    1800
gcucuccacc aaguuucgg agcaaucuau ggggcugccu uuaguggggu uucauggacu    1860
augaaaaucc ucauaggagu caucaucaca uggauaggaa ugaauucacg uagcaccuca    1920
cugucugugu cacuaguauu ggugggaauc auaacacugu acuugggagc uaugguugcag    1980
gcu                                                                 1983
```

<210> SEQ ID NO 6
<211> LENGTH: 10735
<212> TYPE: RNA
<213> ORGANISM: Artificial Sequence -continued

<220> FEATURE:
<223> OTHER INFORMATION: VDV1

<400> SEQUENCE: 6

```
aguuguuagu cuacguggac cgacaagaac aguuucgaau cggaagcuug cuuaacguag     60
uucuaacagu uuuuuauuag agagcagauc ucugaugauc aaccaacgaa aaaagacggg    120
ucgaccgucu uucaauaugc ugaaacgcgc gagaaaccgc gugucaacug uuucacaguu    180
ggcgaagaga uucucaaaag gauugcucuc aggccaagga cccaugaaau uggugauggc    240
uuucauagca uucuuaagau uucuagccau acccccaaca gcaggaauuu uggcuagaug    300
gggcucauuc aagaagaaug gagcgauuaa aguguuacgg gguuucaaga gagaaaucuc    360
aaacaugcua aacauaauga acaggaggaa aagauccgug accaugcucc uuaugcugcu    420
gcccacagcc cuggcguucc aucugacgac acgaggggga gagccgcaua ugauaguuag    480
caagcaggaa agaggaaagu cacuuuuguu caagaccucu gcagguguca acaugugcac    540
ccucauugcg auggauuugg gagaguugug ugaggacacg augaccuaca aaugccccg     600
gaucacugag gcggaaccag augacguuga cuguuggugc aaugccacgg acacaugggu    660
gaccuaugga acgugcucuc aaacuggcga acaccgacga gacaaacguu ccgucgcauu    720
ggccccacac gugggggcuug gccuagaaac aagagccgaa acguggaugu ccucugaagg    780
ugcuuggaaa cagauacaaa aaguagagac uugggcucug agacauccag gauucacggu    840
gauagcccuu uuucuagcac augccauagg aacauccauc acccagaaag ggaucauuuu    900
cauuuugcug augcugguaa caccaucuau ggccaugcga ugcgugggaa uaggcaacag    960
agacuucgug gaaggacugu caggagcaac auggguggau gugguacugg agcauggaag   1020
uugcgucacc accauggcaa aaaacaaacc aacacuggac auugaacucu ugaagacgga   1080
ggucacaaac ccugcaguuc ugcguaaauu gugcauugaa gcuaaaauau caaacaccac   1140
caccgauucg agauguccaa cacaaggaga agccacacug guggaagaac aagacgcgaa   1200
cuuugugugc cgacgaacgu ucguggacag aggcuggggc aauggcugug ggcuauucgg   1260
aaaagguagu cuaauaacgu gugccaaguu uaagugugug acaaaacuag aaggaaagau   1320
agcucaauau gaaaaccuaa aauauucagu gauagucacc guccacacug gagaucagca   1380
ccaggugggga aaugagacua cagaacaugg aacaacugca accauaacac cucaagcucc   1440
uacgucggaa auacagcuga ccgacuacgg aacccuuaca uuagauuguu caccuaggac   1500
agggcuagau uuuaacgaga ugguguugcu gacaaugaaa aagaaaucau ggcuugucca   1560
caaacagugg uuucuagacu uaccacugcc uuggaccucu ggggcuuuaa caucccaaga   1620
gacuuggaac agacaagauu uacuggucac auuuaagaca gcucaugcaa agaagcagga   1680
aguagucgua cuaggaucac aagaaggagc aaugcacacu gcgcugacug gagcgacaga   1740
aauccaaacg ucaggaacga caacaauuuu cgcaggacac cuaaaaugca gacuaaaaau   1800
ggacaaacua acuuuaaaag ggaugucaua ugugaugugc acaggcucau ucaaguuaga   1860
gaaagaagug gcugagaccc agcauggaac uguucuggug cagguuaaau augaaggaac   1920
agacgcacca ugcaagauuc ccuuuucgac ccaagaugag aaaggagcaa cccagaaugg   1980
gagauuaaua acagccaacc ccauagucac ugacaaagaa aaaccaguca auauugaggc   2040
agaaccaccc uuuggugaga gcuacaucgu gguaggagca ggugaaaaag cuuugaaacu   2100
aagcugguuc aagaaaggaa gcagcauagg gaaaauguuu gaagcaacug cccgaggagc   2160
acgaaggaug gccauucugg gagacaccgc augggacuuc gguucuauag gaggaguguu   2220
```

```
cacgucuaug ggaaaacugg uacaccaggu uuuuggaacu gcauauggag uuuguuuag    2280 cggaguuucu uggaccauga aaauaggaau agggauucug cugacauggc uaggauuaaa    2340
uucaaggaac acgucccuuu cggugaugug caucgcaguu ggcauggucu cacuguaccu    2400
aggagucaug guucaggcag auucgggaug uguaaucaac uggaaaggca gagaacuuaa    2460
auguggaagc ggcauuuuug ucacuaauga aguucacacu uggacagagc aauacaaauu    2520
ccaggcugac uccccaaga gacuaucagc agccauggg aaggcauggg aggagggugu    2580 gugugggaauc cgaucagcca cucgucucga gaacaucaug uggaaacaaa uaucaaauga    2640
auugaaccac auccuacuug aaaaugcauu gaaauuuaca guggucgugg gagacguuag    2700
uggaaucuug gcccaaggaa aaaaaaugau uaggccacaa cccauggaac acaaauacuc    2760
guggaaaagc uggggaaaag cuaaaaucau aggagcggau guacagaaca ccaccuucau    2820
caucgacggc ccaaacaccc cagaaugccc ugacaaucaa agagcaugga auauuuggga    2880
aguagaggac uauggauuug ggauuuucac gacaaacaua ugguugaaau ugcugacuc    2940 cuacacccaa guaugugacc accggcugau gucagcugcc auuaaggaca gcaaggcagu    3000
ccaugcugac augggguacu ggauagaaag ugaaagaac gagacauggu aguuggcgag    3060
agccuccuuu auagaaguua agacaugcau cuggccaaaa ucccacacuc uauggagcaa    3120
uggaguucug gaaagugaaa ugauaauucc aaagauauau ggaggaccaa uaucucagca    3180
caacuacaga ccaggauauu ucacacaaac agcaggccg uggcaccuag caaguugga    3240 acuagauuuc gauuuuugug aagguaccac aguuguugug gaugaacauu guggaaaucg    3300
aggaccaucu cucagaacca caacaguca aggaaagaua auccaugaau ggcugcucag    3360
aucuuguacg cuaccccccc uacguuucaa aggggaagac gggguuuggu acggcaugga    3420
aaucagacca gugaaggaca aggaagagaa ccuggucaag ucaauggcu cugcagggc    3480 aggagaagug gacagcuuu cacuaggacu gcuaugcaua ucaauaauga uugaagaagu    3540 gaugagauc agauggagca aaaaaaugcu gaugacugga acacuggcug uguccuccu    3600 ucuuauaaug ggacaauuga cauggaguga ucugaucagg uuauguauua gguuggagc    3660 caacgcuuca gacaagaugg ggaugggaac aacguaccua gcuuuaaugg ccacuuucaa    3720
aaugagacca auguucgccg ucgggcuauu auuucgcaga cuaacaucua gagaaguucu    3780
ucuucuuaca auuggcuuga gccugguggc auccgguggag cuaccaaguu cccuagagga    3840 gcuggggau ggacuugcaa uaggcaucau gauguugaaa uuauugacug auuuucaguc    3900
acaccagcua uggcuacuc ugcuauccuu gacauuauu aaaacaacuu uucauugca    3960 cuaugcaugg aagacaaugg cuaugguacu gucaauugua ucucucuucc cuuuaugccu    4020
guccacgacc ucucaaaaaa caacauggcu uccggugcug uugggaucuc uuggaugcaa    4080
accacuaccc auguuucuua uaacagaaaa caaaaucugg ggaaggaaga guuggcccu    4140 caaugaagga auuauggcug uuggaauagu uaguauucua cuaaguucac uuuuaaaaa    4200 ugaugugccg cuagccggcc cauuaauagc uggaggcaug cuaauagcau guuaugucau    4260
auccggaagc ucagcugauu uaucacugga gaaagcggcu gagguccccu gggaggaaga    4320 agcagaaacac ucaggcgccu cacacaauau acuaguagag guucaagaug auggaaccau    4380
gaagauaaaa gaugaagaga gagaugacac gcucaccauu cuccuuaaag caacucugcu    4440
ggcagucuca gggguguacc caaugucaau accagcgacc cuuuuugugu gguauuuug    4500 gcagaaaaag aaacagagau caggagcu augggacaca cccagcccc cagaaguga    4560 aagagcaguu cuugaugaug gcaucuauag aauuuugcaa agaggacugu uggcagguc    4620
```

```
ccaaguagga guaggaguuu uccaagaagg cguguuccac acaauguggc acgucacuag    4680
gggagcuguc cucauguauc aaggaaaaag gcuggaacca agcugggcca gugucaaaaa    4740
agacuugauc ucauauggag gagguuggag guuucaagga uccuggaaca cgggagaaga    4800
aguacaggug auugcuguug aaccgggaaa aaaccccaaa aauguacaaa caacgccggg    4860
uaccuucaag accccugaag gcgaaguugg agccauagcc uuagacuuua aaccuggcac    4920
aucuggaucu cccaucguaa acagagaggg aaaaauagua ggucuuuaug gaauggagu     4980 ggugacaaca agcggaacuu acguuagugc cauagcucaa gcuaaggcau cacaagaagg    5040
gccucuacca gagauugagg acaagguguu uaggaaaaga aacuuaacaa uaauggaccu    5100
acauccagga ucgggaaaaa caagaagaua ccuuccagcc auaguccgug aggccauaaa    5160
aaggaagcug cgcacgcuaa uccuagcucc cacaagaguu gucgcuucug aaauggcaga    5220
ggcacucaag ggagugccaa uaagguauca gacaacagca gugaagagug aacacacagg    5280
aaaggagaua guugaccuua ugugccacgc cacuuucacc augcgccucc ugucucccgu    5340
gagaguuccc aauuauaaca ugauuaucau ggaugaagca cacuucaccg auccagccag    5400
cauagcagcc agagguaca ucucaacccg aguggguaug ggugaagcag cugcgaucuu     5460
uaugacagcc acucccccag gaucggugga ggccuuucca cagagcaaug caauuaucca    5520
agaugaggaa agagacauuc cugagagauc auggaacuca ggcuaugacu ggaucacuga    5580
uuuuccaggu aaaacagucu gguuuguucc aagcaucaaa ucaggaaaug acauugccaa    5640
cuguuuaaga aaaacggga aacgggugau ccaauugagc agaaaaaccu uugacacuga     5700
guaccagaaa acaaaaaaca cgacuggga cuaugucguc acaacagaca uuccgaaau     5760 gggagcaaau uuccgggccg acagggaau agacccaagg cggugucuga accgguaau     5820 acuaaaagau ggccagagc gcgucauucu agccggaccg augccaguga cuguggccag    5880
ugccgcccag aggagaggaa gaauuggaag gaaccaaaac aaggaaggug aucaguauau    5940 uuacaugga cagccuuuaa aaaaugauga ggaccacgcu cauuggacag aagcaaagau     6000
gcuccuugac aauauaaaca caccagaagg gauuacccca gcccucuuug ccggagag      6060 agaaaagagu gcagcuauag acgggggaaua cagacugcgg ggugaagcaa ggaaaacguu    6120
cguggagcuc augagaagag gggaucuacc agucuggcua uccuacaaag uugccucaga    6180
aggcuuccag uauccgaca gaaggugug cuucgauggg gaaaggaaca accagguguu     6240
ggaggagaac auggacgugg agaucuggac aaaagaagga gaaagaaaga acuacgacc      6300 ucgcugguug gacgccagaa cauacucuga cccacuggcu cugcgcgagu uuaagaguu      6360 ugcagcagga agaagaagcg ucucaggugga ccuaauauua gaaauaggga acuuccaca    6420 acauuugacg caaagggccc agaaugcuuu ggacaacuug ucauguugc acaauuccga     6480 acaaggagga aaagccuaua gacaugcuau ggaagaacug ccagacacaa uagaaacguu    6540
gaugcuccua gccuugauag cuguguugac ugguggagug acgcucucu ccuaucagg     6600 aagaggucua ggaaaaacau cuaucggcuu acucugcgug auggccucaa gcgcacuguu    6660
auggauggcc agugugggagc cccauuggau agcggccucc aucauacugg aguucuuucu    6720 gauguacug cuuauccag agccagacag acagcgcacu ccacaggaca accagcuagc    6780
auauggggug auaggucugu uaucgugau auugacagug gcagccaaug agaugggauu    6840
auuggaaacc acaaagaaag accugggau uggccaugua gcugcugaaa accaccacca    6900
ugcuacaaug cuggacguag accuacaucc agcuucagcc uggacccucu augcaguggc    6960
```

```
cacaacaauc aucacuccua ugaugagaca cacaauugaa acacaacgg  caaauauuuc    7020 ccugacagcc aucgcaaacc aagcagcuau auugauggga cuugacaagg gauggccaau    7080
aucgaagaug gacauaggag uuccacuucu cgccuugggg ugcuauuccc aagugaaucc    7140
gcugacacug auagcggcag uauugaugcu aguagcucau uacgccauaa uuggaccugg    7200
acugcaagca aaagcuacua gagaagcuca aaaaagaaca gcggcuggaa uaaugaaaaa    7260
uccaacuguc gacgggauug uugcaauaga cuuagauccc gugguuuacg augcaaaauu    7320
ugaaaaacag cuaggccaaa uaauguuguu gauacuuugc acaucacaga uucuuuugau    7380
gcggacuaca ugggccuugu ugaauccau  cacauuggcu acuggaccuc ugaccacucu    7440
uugggaggga ucuccaggaa aauucuggaa caccacaaua gcgguaucca uggcaaacau    7500 uuucagggg  aguuaucuag caggagcagg ucuggccuuc ucauuaauga aaucucuagg    7560
aggagguagg agaggcacgg gagcccaagg ggaaacacug ggagaaaaau ggaaaagaca    7620
acuaaaccaa cugagcaagu cagaauucaa uacuuacaag aggaguggga uuauggaggu    7680
ggauagaucc gaagccaaag agggacugaa aagaggagaa caaccaaac  acgcaguauc    7740 gagaggaacg gccaaacuga ggugguucgu ggagaggaac cuugugaaac cagaagggaa    7800
agucauagac cucggguugug gaagaggugg cugg ucauau uauugcgcug gcugaagaa    7860 agucacagaa gugaaaggau acacaaaagg aggaccugga caugaggaac caaucccaau    7920
ggcgaccuau ggauggaacc uaguaaggcu gcacuccgga aaagauguau uuuuauacc    7980 accugagaaa ugugacaccc uuuuguguga uauuggugag uccucuccga acccaacuau    8040
agaggaagga agaacguuac guguucgaa  augguggaa  ccauggcuca gaggaaacca    8100
auuuugcaua aaaauucuaa auccauauau gccgagcgug uagaaacuc  uggaacaaau    8160 gcaaagaaaa cauggaggaa ugcuagcgcg aaacccacuc ucaagaaauu ccacccauga    8220
aauguacugg guucaugug  gaacaggaaa cauugugca  gcaguaaaca ugacaucuag    8280
aauguugcua aaucgguuca caauggcuca caggaagcca acauaugaaa gagacguga     8340 cuuaggcgcu ggaacaagac augugcagu  agaaccagag guagccaacc uagauaucau    8400
uggccagagg auagagaaua uaaaaaauga acauaaguca acauggcauu augaugagga    8460
caauccauac aaaacauggg ccuaucaugg aucauaugag guuaagccau caggaucggc    8520
cucauccaug gucaauggcg uggugagauu gcucaccaaa ccauggg aug uuauccccau    8580 ggucacacaa auagccauga cugauaccac acccuuugga caacagaggg uguuaaaga     8640 gaaaguugac acgcgcacac caaaagcaaa acgggcaca  gcacaaauua uggaagugac    8700
agccaggugg uuaugggguu uccuuucuag aaacaaaaaa cccagaauuu gcacaagaga    8760
ggaguuuaca agaaaaguua ggucaaacgc agcuauugga gcaguguucg uugaugaaaa    8820
ucaauggaac ucggcaaaag aagcagugga agacgaacgg uucuggggaa cuguccacag    8880
agagagggag cuucauaaac aggggaaaug ugcacgugu  gucuacaaua ugaugggg aa    8940 gagagagaaa aaauuaggag aguucggaaa ggcaaaagga agcgugcaa  uagguacau     9000 gugguuggga gcacgcuucc uagaguuuga agcccuuggu ucaugaaug  aagaucacug    9060 guucaguaga gagaauucac ucaguggagu ggaaggagaa ggaccccaca acuugg aua    9120 cauacucaga gacauaucaa ggauuccagg ggggaacaug uaugcagaug acacagccgg    9180
augggacaca agaauaacag aggaugaucu ccagaaugag gcuaaaauca cugacaucau    9240
ggagcccgaa caugcccugc uggcuacguc aaucuuuaag cugaccuacc aaaauaaggu    9300 gguaaggggug cagagaccag caaaaaaugg aaccgugaug gauguuauau ccagacguga    9360
```

```
ccagagaggc aguggacagg uuggaacuua uggcuuaaac acuuucacca acauggaggc    9420
ccaacugaua agacaaaugg agucugaggg aaucuuuuua cccagcgaau uggaaacccc    9480
aaaucuagcc ggaagaguuc ucgacugguu ggaaaaauau ggugucgaaa ggcugaaaag    9540
aauggcaauc agcggagaug acuguguggu gaaaccaauu gaugcaggu ucgcaacagc     9600 cuuaacagcu uugaaugaca ugggaaaagu aagaaaagac auaccacaau gggaaccuuc    9660
aaaaggaugg aaugauuggc aacaagugcc uuucuguuca caccacuucc accagcuaau    9720
uaugaaggau gggagggaga uaguggugcc augccgcaac caagaugaac uuguggggag    9780
ggccagagua ucacaaggcg ccggauggag ccugagagaa accgcaugcc uaggcaaguc    9840
auaugcacaa augguggcagc ugauguauuu ccacaggaga gaccugagac uggcggcuaa   9900
cgcuauuugu ucagccguuc caguugauug ggucccaacc agccgcacca ccugguccgau  9960 ccaugcccau caccaaugga ugacaacaga agacauguua ucaguaugga auagggucug   10020
gauagaggaa aacccaugga uggaggauaa gacucaugug uccaguuggg aagaaguucc   10080
auaccuagga aagagggaag aucaguggug uggauccccug uaggcuuaa cagcaagggc   10140 caccuggggcc acuaauauac aaguggccau aaaccaagug agaaggcuca uugggaauga  10200
gaauuaucua gauuacauga caucaaugaa gagauucaag aaugagagug aucccgaagg   10260
ggcacucugg uaagucaaca cauucacaaa auaaaggaaa auaaaaaauc aaaugaggca   10320
agaagucagg ccagauuaag ccauaguacg guaagagcua ugcugccugu gagccccguc   10380
caaggacgua aaaugaaguc aggccgaaag ccacgguuug agcaagccgu gcugccugug   10440
gcuccaucgu ggggauguaa aaacccggga ggcugcaacc cauggaagcu uacgcaugg    10500 gguagcagac uaguguuag aggagacccc ucccaagaca caacgcagca gcggggccca    10560
acaccagggg aagcuguacc cuggugguaa ggacuagagg uuagaggaga cccccgcgu    10620 aacaauaaac agcauauuga cgcugggaga gaccagagau ccugcugucu cuacagcauc   10680
auuccaggca cagaacgcca gaaaauggaa uggugcuguu gaaucaacag guucu         10735
```

<210> SEQ ID NO 7
<211> LENGTH: 10723
<212> TYPE: RNA
<213> ORGANISM: Artificial Sequence
<220> FEATURE:
<223> OTHER INFORMATION: VDV2

<400> SEQUENCE: 7

```
aguuguuagu cuacgugac cgacaaagac agauucuuug agggagcuaa gcucaaugua       60
guucuaacag uuuuuuaauu agagagcaga ucucugauga auaaccaacg aaaaaggcg       120 aaaaacacgc cuucaauau gcugaaacgc gagagaaacc gcgugucgac ugugcaacag      180
cugacaaaga gauucucacu uggaaugcug cagggacgag gaccauuaaa acuguucaug     240 gcccugguggg cguccuucg uuccuaaca aucccaccaa cagcagggau auugaagaga      300
uggggaacaa uuaaaaaauc aaaagcuauu aauguuuuga gagggucag gaaagagauu      360 ggaaggaugc ugaacaucuu gaauaggaga cgcagaucug caggcaugau cauuuaugcug    420 auuccaacag uguggcgau ccauuuaacc acacguaacg agaaccaca caugaucguc       480 agcagacaag agaaagggaa aagucuucug uuuaaaacag agguggcgu gaacaugugu      540 acccucaugg ccauggaccu uggugaauug ugugaagaca caaucacgua caagugcccc     600
cuucucaggc agaaugagcc agaagacaua gacuguuggu gcaacucuac guccacgug     660
```

```
guaacuuaug ggacguguac caccauggga gaacauagaa gagaaaaaag aucaguggca    720
cucguuccac augugcgaau gggacuggag acacgaacug aaacauggau gucaucagaa    780
ggggccugga acaugucca gagaauugaa acuuggaucu ugagacaucc aggcuucacc    840
augauggcag caauccuggc auacaccaua ggaacgacac auuuccaaag agcccugauu    900
uucaucuuac ugacagcugu cacuccuuca augacaaugc guugcauagg aaugucaaau    960
agagacuuug uggaaggggu ucaggagga agcggguug acauagucuu agaacaugga    1020
agcuguguga cgacgauggc aaaaaacaaa ccaacauugg auuugaacu gauaaaaaca    1080 gaagccaaac agccugccac ccuaaggaag uacuguauag aggcaaagcu aaccaacaca    1140
acaacagaau cucgcugccc aacacaaggg gaacccagcc uaaaugaaga gcaggacaaa    1200
agguucgucu gcaaacacuc cauggugaca gaggaugggg aaauggaug uggacuauuu    1260 ggaaagggag gcauugugac cugugcuaug uucagaugca aaagaacau ggaaggaaaa    1320 guugugcaac cagaaaacuu ggaauacacc auugugauaa caccucacuc aggggaagag    1380
caugcagucg gaaaugacac aggaaaacau ggcaaggaaa ucaaauaac accacagagu    1440 uccaucacag aagcagaauu gacagguuau ggcacuguca caauggagug cucuccaaga    1500 acggccucg acuucaauga gauggugug cugcagaugg aaaauaaagc uuggcuggug    1560
cacaggcaau gguccuaga ccugccguua ccaugguugc ccggagcgga cacacaagag    1620
ucaaauugga uacagaagga gacauugguc acuucaaaa aucccaugc gaagaaacag    1680 gauguuguug uuuuaggauc ccaagaaggg gccaugcaca cagcacuuac aggggccaca    1740
gaaauccaaa ugucaucagg aaacuuacuc uucacaggac aucucaagug caggcugaga    1800
auggacaagc uacagcucaa aggaaugca uacucuaugu gcacaggaaa guuuaaaguu    1860
gugaaggaaa uagcagaaac acaacaugga acaauaguua ucagugca auaugaaggg    1920 gacggcucuc caugcaagau ccccuuugag auaauggauu uggaaaaaag acaugucuua    1980
ggucgccuga uuacaguaa cccaauugug acagaaaaag auagcccagu caacauagaa    2040
gcagaaccuc cauuuggaga cagcuacauc aucauaggag uagagccggg acaacugaag    2100
cucaacuggu uuaagaaagg aaguucuauc ggccaaaugu uugagacaac aaugagggggg    2160 gcgaagagaa uggccauuuu aggugacaca gccugggauu uggauccuu ggaggagug    2220 uuuacaucua uaggaaaggc ucuccaccaa gucuuuggag caaucuaugg agcugccuuc    2280
agugggguuu caauggacuau gaaaauccuc auaggaguca uuaucacaug gauaggaaug    2340
aauucacgca gcaccucacu gucugugaca cuaguauugg uggaauugu gacacuguau    2400 uugggaguca ugguguaggc cgauaguggu ugcguuguga gcuggaaaaa caaagaacug    2460
aaauguggca gugggauuuu caucacagac aacgugcaca auggacaga acaauacaaa    2520 uccaaccag aauccccuuc aaaacuagcu ucagcuaucc agaaagccca ugaagaggac    2580
auuuguggaa uccgcucagu aacaagacug gagaaucuga uggaaaca auaacacca    2640 gaauugaauc acauucuauc agaaaaugag gugaaguuaa cuauuaugac aggagacauc    2700
aaaggaauca ugcaggcagg aaaacgaucu cugcggccuc agcccacuga gcugaaguau    2760
ucauggaaaa caugggcaa agcaaaaaug cucucuacag agucucauaa ccagaccuuu    2820
cucauugaug gccccgaaac agcagaaugc cccaacacaa auagagcuug gaauucguug    2880
gaaguugaag cuauggcuu uggaguauuc accaccauua uauggcuaaa auugaaagaa    2940
aaacaggaug uauucugcga cucaaaacuc augucagcgg ccauaaaaga caacagagcc    3000
guccaugccg auauggguuu auggauagaa agugcacuca augacacaug gaagauagag    3060
```

```
aaagcccucuu ucauugaagu uaaaaacugc cacuggccaa aaucacacac ccucuggagc    3120
aauggagugc uagaaaguga gaugauaauu ccaaagaauc ucgcuggacc agugucucaa    3180
cacaacuaua gaccaggcua ccauacacaa auaacaggac cauggcaucu agguaagcuu    3240
gagauggacu uugauuucug ugauggaaca acaguggag ugacugagga cugcggaaau    3300
agaggacccu cuuugagaac aaccacugcc ucuggaaaac ucauaacaga auggugcugc    3360
cgaucuugca cauuaccacc gcuaagauac agaggugagg augggugcug guacgggaug    3420
gaaaucagac cauugaagga gaaagaagag aauuugguca acuccuuggu cacagcugga    3480
caugggcagg ucgacaaccuu ucacuagga gucuuuggga uggcauuguu ccuggaggaa    3540
augcuuagga cccgaguagg aacgaaacau gcaauacuac uaguugcagu ucuuuugug    3600 acauugauca cagggaacau guccuuuaga gaccugggaa gagugauggu uaugguaggc    3660 gccacauga cggaugacau agguaugggc gugacuuauc uugcccuacu agcagccuuc    3720
aaagucagac caacuuuugc agcuggacua cucuugagaa agcugaccuc caaggaauug    3780
augaugacua cuauaggaau uguacccuc ucccagagca ccauaccaga gaccauucuu    3840 gaguugcug augcguuagc cuuaggcaug augguccuca aaauggugag aaauauggaa    3900
aaguaucaau uggcagugac uaucauggcu aucuugugcg ucccaaacgc agugauauua    3960
caaaacgcau ggaaagugag uugcacaaua uuggcagugg uguccguuuc cccacuguuc    4020
uuaacauccu cacagcaaaa aacagauugg auaccauuag cauugacgau caaaggucuc    4080
aauccaacag cuauuuuucu aacaacccuc ucaagaacca gcaagaaaag gagcuggcca    4140
uuaaaugagg cuaucauggc agucgggaug gugagcauuu uagccaguuc ucuccuaaaa    4200
aaugauauuc ccaugacagg accauuagug gcuggagggc uccucacugu gugcuacgug    4260
cucacuggac gaucggccga uuggaacug gagagagcag ccgaugucaa augggaagac    4320
caggcagaga uaucaggaag caguccaauc cugucaauaa caauaucaga agauggagc    4380 augucgauaa aaaaugaaga ggaagaacaa acacugacca uacucauuag aacaggauug    4440 cugguaucu caggacuuuu uccuguauca uaccaauca cggcagcagc auguuaccug    4500
ugggaaguga agaaacaacg ggccggagua uuguggaug uccuucacc cccacccaug    4560 ggaaaggcug aacuggaaga uggagccuau agaauuaagc aaaaaggau ucuuggauau    4620 ucccagaucg gagccggagu uuacaaagaa ggaacauucc auacaaugug gcaugucaca    4680
cguggcgcug uucuaaugca uaaggaaag aggauugaac caacaugggc ggacgucaag    4740
aaagaccuaa uacauaugg aggaggcugg aaguuagaag gagaauggaa ggaagagaa    4800 gaaguccagg uauuggcacu ggagccugga aaaaauccaa gagccgucca aacgaaaccu    4860
ggucuuuuca aaaccaacgc cggaacaaua ggugcuguau cucggacuu uucuccugga    4920 acgucaggau ucccaauuau cgacaaaaaa ggaaaaguug ugggucuuua gguaauggu    4980 guuguuacaa ggaguggagc auaugugagu gcuauagccc agacgaaaaa aagcauugaa    5040
gacaacccag agaucgaaga ucacauuuuc cgaaagagaa gacugaccau caugaccuc    5100 cacccaggag cgggaaagac gaagagauac cuuccggcca uagucagaga agcuauaaaa    5160 cggguuuga gaacauuaau cuuggccccc acuagaguug uggcagcuga aauggaggaa    5220
gcccuuagag gacuuccaau aagauaccag accccagcca ucagagcuga gcacaccggg    5280
cgggagauug uggaccuaau gugucaugcc acauuuacca ugaggcugcu aucaccaguu    5340
agagugccaa acuacaaccu gauuaucaug gacgaagccc auucacaga cccagcaagu    5400
```

```
auagcagcua gaggauacau cucaacucga guggagaugg gugaggcagc ugggauuuuu    5460
augacagcca cuccccgggg aagcagagac ccauuccuc agagcaaugc accaaucaua    5520
gaugaagaaa gagaaauccc ugaacgcucg uggaauuccg gacaugaaug ggucacggau    5580
uuuaaaggga agacuguuug guucguucca aguauaaaag caggaaauga uauagcagcu    5640
ugccugagga aaaauggaaa gaaagugaua caacucagua ggaagaccuu ugauucugag    5700
uaugucaaga cuagaaccaa ugauugggac uucguggruua caacugacau uucagaaaug    5760
ggugccaauu ucaaggcuga gagggguuaua daccccagac gcugcaugaa accagucaua    5820
cuaacagaug gugaagagcg ggugauucug gcaggaccua ugccagugac ccacucuagu    5880
gcagcacaaa gaagagggag aauaggaaga aauccaaaaa augagaauga ccaguacaua    5940
uacauggggg aaccucugga aaaugaugaa gacugugcac acuggaaaga agcuaaaaug    6000
cuccuagaua acaucaacac gccagaagga aucauuccua gcauguucga accagagcgu    6060
gaaaaggugg augccauuga uggcgaauac cgcuugagag agaagcaag gaaaaccuuu    6120
guagacuuaa ugagaagagg agaccuacca gucugguugg ccuacagagu ggcagcugaa    6180
ggcaucaacu acgcagacag aagguggugu uuugauggag ucaagaacaa ccaaauccua    6240
gaagaaaacg uggaaguuga aaucuggaca aaagaagggg aaaggaagaa auugaaaccc    6300
agauggguugg augcuaggau cuauucugac ccacuggcgc uaaaagaauu uaaggaauuu    6360
gcagccggaa gaaagucucu gacccugaac cuaaucacag aaaugggguag gcucccaacc    6420
uucaugacuc agaaggcaag agacgcacug gacaacuuag cagugcugca cacggcugag    6480
gcagguggaa gggcguacaa ccaugcucuc agugaacugc cggagacccu ggagacauug    6540
cuuuuacuga cacuucuggc uacagucacg ggagggaucu uuuuauucu ugaugagcgca    6600
aggggcauag gaagaugac ccugggaaug ugcugcauaa ucacggcuag cauccuccua    6660
ugguacgcac aaauacagcc acacugguga gcagcuucaa uaauacugga guuuuucuc    6720
auaguuuugc uuauuccaga accugaaaaa cagagaacac cccaagacaa ccaacugacc    6780
uacguuguca uagccauccu cacaguggug gccgcaacca uggcaaacga daugggguuc    6840
cuagaaaaa cgaagaaga ucucggauug gaagcauug caaccagca acccgagagc    6900
aacauccugg acauagaucu acguccugca ucagcaugga cgcuguaugc cguggccaca    6960
acauuuguua caccaaugu gagacauagc auugaaaauu cucagugaa uguguccua    7020
acagcuauag ccaaccaagc cacaguguua augggucucg ggaaaggaug gccauuguca    7080
aagauggaca ucggaguucc ccuucucgcc auuggaugcu acucacaagu caaccccaua    7140
acucucacag cagcucuuuu cuuauugua gcacauuaug ccaucauagg gccaggacuc    7200
caagcaaaag caaccagaga agcucagaaa agagcagcgg cgggcaucau gaaaaaccca    7260
acugucgaug gaauaacagu gauugaccua gauccaauac cuuaugaucc aaaguuugaa    7320
aagcaguugg gacaaguaau gcuccuaguc cucugcguga cucaaguauu gaugaugagg    7380
acuacauggg cucuguguga ggcuuuaacc uuagcuaccg ggcccaucuc cacauugugg    7440
gaaggaaauc cagggagguu uuggaacacu accaugcgg ugucaauggc uaacauuuuu    7500
agagggaguu acuggccgg agcuggacuu cucuuuucua uuaugaagaa cacaccaac    7560
acaagaaggg gaacuggcaa cauaggagag acgcuuggag agaaauggaa agccgauug    7620
aacgcauugg gaaaagguga auccagauc uacaagaaaa guggaaucca ggaaguggau    7680
agaaccuuag caaagaagg cauuaaaga ggagaaacgg accacacgc ugucgcga    7740
ggcucagcaa aacugagaug guucguugag agaaacaugg ucacaccaga agggaaagua    7800
```

```
guggaccucg guuguggcag aggaggcugg ucauacuauu guggaggacu aaagaaugua    7860
agagaaguca aaggccuaac aaaaggagga ccaggacacg aagaacccau ccccauguca    7920
acauaugggu ggaaucuagu gcgucuucaa aguggaguug acguuuucuu caucccgcca    7980
gaaaagugug acacauuauu gugugacaua ggggagucau caccaaaucc cacaguggaa    8040
gcaggacgaa cacucagagu ccuuaacuua guagaaaaau gguugaacaa caacacucaa    8100
uuuugcauaa agguucucaa cccauauaug cccucaguca uagaaaaaau ggaagcacua    8160
caaaggaaau auggaggagc cuuagugagg aauccacucu cacgaaacuc cacacaugag    8220
auguacuggg uauccaaugc uuccgggaac auagugucau cagugaacau gauuucaagg    8280
auguugauca acagauuuac aaugagauac aagaaagcca cuuacgagcc ggauguugac    8340
cucggaagcg gaacccguaa caucgggauu gaaagugaga uaccaaaccu agauauaauu    8400
gggaaaagaa uagaaaaaau aaagcaagag caugaaacau cauggcacua ugaccaagac    8460
cacccauaca aaacgugggc auaccauggu agcuaugaaa caaaacagac uggaucagca    8520
ucauccaugg ucaacggagu ggucaggcug cugacaaaac cuugggacgu gucccccaug    8580
gugacacaga uggcaaugac agacacgacu ccauuuggaa acagcgcgu uuuuaaagag    8640 aaaguggaca cgagaaccca agaaccgaaa gaaggcacga agaaacuaau gaaaauaaca    8700
gcagaguggc uuuggaaaga auuagggaag aaaaagacac ccaggaugug caccagagaa    8760
gaauucacaa gaaaggugag aagcaaugca gccuuggggg ccauauucac ugaugagaac    8820
aaguggaagu cggcacguga ggcuguugaa gauagauaggu uuugggagcu gguugacaag    8880
gaaaggaauc uccaucuuga aggaaagugu gaaacaugug uguacaacau gaugggaaaa    8940
agagagaaga agcuagggga auucggcaag gcaaaaggca gcagagccau auggacaug    9000 uggcuuggag cacgcuucuu agaguuugaa gcccuaggau ucuuaaauga agaucacugg    9060
uucuccagag agaacccccu gagugga gaag gaagagaag ggcugcacaa gcuagguuac    9120
auucuaagag acgugagcaa gaaagaggga ggagcaaugu augccgauga caccgcagga    9180
ugggauacaa aaaucacacu agaagaccua aaaaaugaag agauggguaac aaaccacaug    9240 gaaggagaac acaagaaacu agccgaggcc auuuucaaac uaacguacca aaacaaggug    9300
gugcgcgugc aaagaccaac accaagaggc acaguaaugg acaucauauc gagaagagac    9360
caaagaggua guggacaagu uggcaccuau ggacucaaua cuuucaccaa uauggaagcc    9420
caacuaauca gacagaugga gggagaagga gucuuuaaaa gcauucagca ccuaacaauc    9480
acagaagaaa ucgcgugca aaacgguua gcaagaguugg ggcgcgaaag guuaucaaga    9540
auggccauca guggagauga uuguguugug aaaccuuuag augacaagguu cgcaagcgcu    9600 uuaacagcuc uaaaugacau gggaaagauu aggaaagaca acaacaaug ggaaccuuca    9660 agaggaugga augauuggac acaagugccc uucuguucac accauuucca ugaguuaauc    9720
augaaagacg gucgcuacu cguuguucca auguagaaaac aagaugaacu gauuggcaga    9780
gcccgaaucu cccaaggagc agggugucu uugcgggaga cggccuguuu ggggaagucu    9840
uacgcccaaa uguggagcuu gauguacuuc cacagacgcg accucaggcu ggcggcaaau    9900
gcuauuugcu cggcaguacc aucacauugg guucaacaa gucgaacaac cuguccaua    9960 caugcuaaac augaauggau gacaacggaa gacaugcuga cagucuggaa cagggugugg    10020
auucaagaaa acccauggau ggaagacaaa acuccaguugg aaacauggga ggaauccca    10080 uacuugggga aagagaagag ccaaugggcg ggcucauuga uugggguuaac aagcagggcc    10140
```

-continued

```
accugggcaa agaacaucca agcagcaaua aaucaaguua gaucccuuau aggcaaugaa  10200
gaauacacag auuacaugcc auccaugaaa agauucagaa gagaagagga agaagcagga  10260
guucuguggu agaaagcaaa acuaacauga aacaaggcua gaagucaggu cggauuaagc  10320
cauaguacgg aaaaaacuau gcuaccugug agccccgucc aaggacguua aaagaaguca  10380
ggccaucaua aaugccauag cuugaguaaa cuaugcagcc uguagcucca ccugagaagg  10440
uguaaaaaau ccgggaggcc acaaaccaug gaagcuguac gcauggcgua guggacuagc  10500
gguuagggga gaccccuccc uuacaaaucg cagcaacaau gggggcccaa ggcgagauga  10560
agcuguaguc ucgcuggaag gacuagaggu uagaggagac cccccgaaa caaaaaacag  10620 cauauugacg cugggaaaga ccagagaucc ugcugucucc ucagcaucau uccaggcaca  10680
gaacgccaga aaauggaaug gugcuguuga aucaacaggu ucu                   10723
```

COMPOSITIONS FOR BOOSTER VACCINATION AGAINST DENGUE

CROSS-REFERENCE TO APPLICATION

This application is a U.S. national phase application of International Patent Application No. PCT/IB2018/001219 filed Oct. 5, 2018, which claims the benefit of U.S. Patent Application No. 62/568,525 filed Oct. 5, 2017, the disclosure of each of which is hereby incorporated by reference in its entirety.

This application incorporates-by-reference nucleotide and/or amino acid sequences which are present in the accompanying sequence listing as part of this application.

FIELD OF THE INVENTION

The present invention relates to vaccine compositions and uses of such compositions as booster vaccines in a method of generating a neutralizing antibody response against dengue virus, in human subjects.

BACKGROUND

Dengue is the second most important infectious tropical disease after malaria with approximately one-half of the world's population living in areas where there is a risk of epidemic transmission. There are estimated to be 390 million cases of dengue every year and roughly 96 million people have clinically apparent disease. Each year, an estimated 500,000 people, including children, have a severe form of dengue requiring hospitalization, which puts a huge strain on health care systems during outbreaks. Approximately 2.5% of those affected with a severe form of dengue will die (World Health Organization. Dengue and dengue haemorrhagic fever, Fact sheet N° 117, Updated May 2015. Available from URL: http://www.who.int/mediacentre/factsheets/fs117/en/.) Thus, according to WHO, there is an urgent need to develop a safe and effective vaccine against the four serotypes of dengue virus to protect people in endemic countries.

Dengue disease is caused by four antigenically distinct, but closely related dengue virus serotypes of the flavivirus genus (Gubler et al., 1988, in: Epidemiology of arthropod-borne viral disease. Monath TPM, editor, Boca Raton (Fla.): CRC Press: 223-60; Kautner et al., 1997, J. of Pediatrics, 131: 516-524; Rigau-Perez et al., 1998, Lancet, 352: 971-977; Vaughn et al., 1997, J. Infect. Dis., 176: 322-30). Dengue viruses are positive-sense, single-stranded RNA viruses.

Dengue disease is usually transmitted by injection of the dengue virus during the blood meal of an *Aedes aegypti* mosquito infected by the virus. After an incubation period of 4-10 days, the illness begins abruptly and is followed by three phases: febrile (2 to 7 days), critical (24-48 hours—during which severe complications may occur) and recovery (48-72 hours). During the critical phase, life threatening complications such as haemorrhages, shock and acute organ impairment may occur. A proper management of these unpredictable outcomes can reduce the case fatality rate. Cure of dengue fever is complete after 7 to 10 days, but prolonged asthenia is normal. Reduced leukocyte and platelet numbers are frequently observed.

Severe forms of dengue disease including dengue haemorrhagic fever (DHF) are potentially deadly complication of dengue virus infection. DHF is characterized by a high fever and symptoms of dengue disease, but with extreme lethargy and drowsiness. Increased vascular permeability and abnormal homeostasis can lead to a decrease in blood volume, hypotension, and in severe cases, hypovolemic shock and internal bleeding. Two factors appear to play a major role in the occurrence of DHF—rapid viral replication with a high level of viraemia (the severity of the disease being associated with the level of viraemia; Vaughn et al., 2000, J. Inf. Dis., 181: 2-9) and a major inflammatory response with the release of high levels of inflammatory mediators (Rothman and Ennis, 1999, Virology, 257: 1-6; Alan L. Rothman. 2011, Nature Reviews Immunology, 11: 532-543). The mortality rate for DHF can reach 10% without treatment, but is <1% in most centres with access to treatment. Dengue disease infections are endemic in more than 100 tropical countries and DHF has been documented in 60 of these countries (Gubler, 2002, TRENDS in Microbiology, 10: 100-103).

Dengue shock syndrome (DSS) is a common progression of DHF and is frequently fatal. DSS results from generalized vasculitis leading to plasma leakage into the extravascular space. DSS is characterized by rapid and poor volume pulse, hypotension, cold extremities, and restlessness.

In Asia, DHF and DSS are observed primarily in children, with approximately 90% of those with DHF being less than 15 years of age (Malavige et al., 2004, Postgrad Med. J., 80: 588-601; Meulen et al., 2000, Trop. Med. Int. Health, 5:325-9). In contrast, outbreaks in the Caribbean and Central America have predominantly affected adults (Malavige et al., 2004, Postgrad Med. J., 80: 588-601). Incidence of dengue disease has increased in older age groups in many countries where dengue is endemic (Sabchareon et al, 2012, Lancet, 380, 1559-1567; Messina et al., 2014, Trends Microbiol., 22, 138-146).

The four serotypes of dengue virus possess approximately 60-80% sequence homology. Infection with one dengue serotype provides durable homologous immunity but limited heterologous immunity (Sabin, 1952, Am. J. Trop. Med. Hyg., 1: 30-50). Accordingly, an individual that has been infected with one serotype of dengue may subsequently become infected with a different serotype. It is considered that a second infection arising from a different dengue virus serotype is theoretically a risk factor for the development of DHF, since the majority of patients that exhibit DHF have been previously exposed to at least one of the other four serotypes of dengue virus.

To date, there is no specific treatment for dengue disease. Treatment for dengue disease is symptomatic, with bed rest, control of the fever and pain through antipyretics and analgesics, and adequate drinking. The treatment of DHF requires balancing of liquid losses, replacement of coagulation factors and the infusion of heparin.

Since dengue prevention measures, such as mosquito control and personal protection from bites are limited in efficacy, difficult to enforce and expensive, a safe and efficacious dengue vaccine would be the best mode of prevention.

The Applicant has previously developed a dengue vaccine, marketed under the commercial name Dengvaxia®. The vaccine efficacy of this dengue vaccine was demonstrated inter alia in subjects from 2 to 16 years (Capeding M R, et al., 2014, Lancet; 384(9951):1358-65 and Villar L, et al., 2015, N Engl J Med., 372(2):113-23).

A close analysis of the results obtained with this dengue vaccine however shows that it is particularly effective in the protection against dengue disease of subjects who were already seropositive at the time of the vaccination, i.e.

subjects who had previously been infected by a dengue virus, irrespective of the serotype.

For subjects initially dengue naïve, i.e. who have not previously been infected by a dengue virus, the neutralizing antibody levels after the primary vaccination are however lower that the neutralizing antibody response generated in dengue immune subjects.

Based on analysis of the results from different Phase III efficacy studies, namely that higher levels of neutralizing antibodies (as measured by $PRNT_{50}$) decrease the probability of developing dengue disease, and although no absolute correlate of protection has yet been established for the dengue vaccine, it is considered that higher neutralizing antibody levels are associated with higher vaccine efficacy, i.e. a lower risk of dengue disease. In other words, $PRNT_{50}$ titres 28 days post vaccination are considered to be an inverse correlate of risk (Moodie, Z. et al., Neutralizing Antibody Correlates Analysis of Tetravalent Dengue Vaccine Efficacy Trials in Asia and Latin America, Journal of Infectious Diseases (2018), vol. 217, pages 742-753).

There is thus a need to develop a vaccine composition or a method useful in a vaccination course aiming at enhancing the neutralizing antibody response of human subjects not previously naturally infected by a dengue virus, with a view to efficiently protecting them against dengue, irrespective of the serotype.

SUMMARY OF THE INVENTION

The present invention relates to a vaccine composition for use in a method of booster vaccination for inducing in a human subject a neutralizing antibody response against dengue virus, said composition comprising a dengue antigen of at least one of serotypes 1 to 4 or a nucleic acid construct capable of expressing said antigens in the subject, wherein said subject has previously received a primary vaccination course against each of serotypes 1 to 4 of dengue virus, and said subject was dengue naïve before said primary vaccination course, and wherein said booster vaccination results in at least a 2-fold increase in the neutralizing antibody titre against each of serotypes 1 to 4.

The present invention further relates to a vaccine composition for use in a method of inducing in a human subject a neutralizing antibody response against dengue virus, said composition comprising a dengue antigen of each of serotypes 1 to 4, or a nucleic acid construct capable of expressing in said subject a dengue antigen of each of serotypes 1 to 4;

wherein said composition is administered as:
(a) a primary vaccination, followed by
(b) a booster vaccination,
and wherein the human subject is initially dengue naïve.

Definitions

The term "dengue disease", as used herein, refers to the clinical symptoms, of all grades of severity, exhibited by an individual following infection by a dengue virus. As used herein, the term dengue disease encompasses both the milder manifestations of dengue disease such as dengue fever and the more severe manifestations of dengue fever such as severe dengue as defined herein or dengue haemorrhagic fever (DHF) as defined herein. Since 1975, clinical dengue has been classified according to World Health Organization guidelines (updated in 1997) as (i) dengue fever or (ii) dengue haemorrhagic fever (World Health Organization. Dengue hemorrhagic fever: Diagnosis, treatment, prevention and control $2^{nd}$ Ed. Geneva: WHO, 1997; ISBN 92 4 154500 3). In 2009, the WHO issued new guidelines that classify clinical dengue as (i) dengue with or without warning signs or (ii) severe dengue. Both classifications are shown in FIGS. 1 & 2 of Srikiatkachorn et al., Clin. Infect. Dis. (2011) 53(6): 563. According to the earlier 1997 WHO classification, dengue fever is diagnosed by: (i) the presence of fever with at least two symptoms selected from headache, arthralgia, retro-orbital pain, rash, myalgia, haemorrhagic manifestations, and leucopenia; together with (ii) supportive serology or occurrence at the same location and time as other confirmed dengue cases. Progression to Dengue haemorrhagic fever is confirmed when fever, haemorrhagic manifestations, thrombocytopenia and evidence of plasma leakage are all observed. According to the 2009 WHO classification, diagnosis of dengue requires the presence of: (i) fever and at least two clinical symptoms selected from nausea, vomiting, rash, aches and pains, a positive tourniquet test, or any warning signs selected from abdominal pain and tenderness, persistent vomiting, clinical fluid accumulation, mucosal bleed, lethargy or restlessness, liver enlargement>2 cm or an increase in haematocrit concurrent with a rapid decrease in platelet count; together with (ii) supportive serology or occurrence at the same location and time as other confirmed dengue cases. According to the 2009 WHO classification, severe dengue is defined as a diagnosis of dengue with the observation of any of the following additional events: (i) severe plasma leakage leading to shock or respiratory distress (fluid accumulation); (ii) severe bleeding as evaluated by clinicians; or (iii) severe organ involvement (i.e. liver: AST, ALT≥1000; CNS: impaired consciousness or heart or other organs).

The terms "Dengue haemorrhagic fever" or "DHF", as used herein, are consistent with the 1997 WHO definition and refer to the following symptoms—1) Clinical manifestations: (a) Fever: acute onset, high (≥38° C.) and continuous lasting 2 to 7 days; (b) Any of the following haemorrhagic manifestations: a positive tourniquet test, petechiae, purpura, ecchymosis, epitaxis, gum bleeding, and hematesis and/or melena; 2) Laboratory findings: (a) Thrombocytopenia (platelet count≤$100\times10^9$/L); (b) Plasma leakage as shown by hemoconcentration (haematocrit increased by 20% or more) or pleural effusion (seen on chest X-ray) and/or ascites and/or hypoalbuminemia. The first two clinical criteria (i.e. fever and haemorrhagic manifestations), plus thrombocytopenia and signs of plasma leakage are sufficient to establish a clinical diagnosis of DHF. Pleural effusion (seen on chest X-ray) and/or hypoalbuminemia provide supporting evidence of plasma leakage. DHF, as used herein, may be further defined on the basis of its severity. Thus DHF may be defined as being of Grade I, Grade II, Grade III or Grade IV (World Health Organization. Dengue hemorrhagic fever: Diagnosis, treatment, prevention and control $2^{nd}$ Ed. Geneva: WHO, 1997; ISBN 92 4 154500 3). Grade I is defined as fever accompanied by non-specific constitutional symptoms; the only haemorrhagic manifestation is a positive tourniquet test. Grade II is defined as spontaneous bleeding in addition to the manifestations of Grade I patients, usually in the form of skin or other haemorrhages. Grade III is defined as circulatory failure manifested by a rapid, weak pulse and narrowing of pulse pressure (20 mmHg or less) or hypotension, with the presence of cold clammy skin and restlessness. Grade IV is defined as profound shock with undetectable blood pressure and pulse. As would be understood by a person of skill in the art, in the practice of the present invention, e.g. a method of protecting against DHF, said DHF need not be virologically-confirmed.

The term "viroloqically-confirmed dengue", as used herein, refers to an acute febrile episode (i.e. temperature≥38° C. on at least two consecutive days) which is confirmed to be induced by a dengue virus, e.g. by reverse transcriptase polymerase chain reaction (RT-PCR) and/or by a dengue non-structural 1 (NS1) protein enzyme-linked immunosorbent assay (ELISA). In the RT-PCR method, RNA is extracted from the serum to discard potential Taq polymerase inhibitors or interfering factors, using a commercial kit. Then a dengue screen RT-PCR reaction is carried out with primers from a gene sequence conserved among dengue viruses. Results are expressed as a concentration of logo plaque forming unit (PFU)/mL, by comparison with standards containing known concentrations of viral genomic nucleic acid sequences. Serotype identification of post-infectious dengue viremia is determined by testing serum samples with the Simplexa™ Dengue RT-PCR assay (Focus Diagnostics, Inc. CA, USA). Briefly, RNA is extracted from the serum to discard potential polymerase inhibitors or interfering factors, using a commercial kit. Then the Simplexa™ assay is carried out which incorporates serotype-specific primers from dengue sequences. The results are expressed qualitatively and reported for each dengue serotype as detected or not detected. The Simplexa™ assay is used on all dengue screen RT-PCR positive or dengue NS1 Ag ELISA positive samples for serotype identification. The NS1 ELISA is performed using a commercially available kit (Platella™ Dengue NS1 Ag, Bio-Rad, Marnes-la-Coquette, France). The manufacturer's instructions are followed. The Dengue NS1 Ag test is a one-step sandwich-ELISA based assay that enables detection of NS1 Ag in serum. The test uses murine monoclonal Abs (MAbs) for capture and revelation. Samples and controls are directly and simultaneously incubated with the conjugate within the microplate wells coated with MAb. If NS1 Ag is present in the sample, an immune-complex MAb-NS1-MAb/peroxidase will be formed. The presence of immune-complex is demonstrated by addition of a chromogenic solution that initiates a colour development reaction. After 30 minutes of incubation at room temperature, the enzymatic reaction is stopped by addition of an acid solution. The optical density (OD) reading obtained with a spectrophotometer set at 450/620 nm is proportional to the amount of NS1 Ag present in the sample. The presence of NS1 Ag in an individual sample is determined by comparing the OD reading of the sample to the OD of the cut-off control serum. Sample ratios of <0.5, ≥0.5 to <1.0, and ≥1 are indicative of negative, equivocal, and positive results, respectively.

The terms "severe dengue" or "severe dengue disease", as used herein refer to severe dengue as defined by the Independent Data Monitoring Committee (IDMC) established to oversee the Phase III clinical trials reported herein. According to the IDMC definition, in a case of dengue fever, the appearance of any one of the following criteria results in a diagnosis of severe dengue: (i) Shock (pulse pressures 20 mmHg in a child or adolescent, or hypotension [≤90 mmHg] with tachycardia, weak pulse and poor perfusion); (ii) Bleeding requiring blood transfusion; (iii) Encephalopathy i.e., unconsciousness or poor conscious state or convulsions not attributable to simple febrile convulsion or focal neurological signs. Poor conscious state or unconsciousness must be supported by Glasgow Coma Scale (GCS) score; (iv) Liver impairment (AST>1000 U/L or prothrombin time [PT] International normalized ratio [INR]>1.5); (v) Impaired kidney function (Serum creatinine≥1.5 mg/dL) or (vi) Myocarditis, pericarditis or heart failure (clinical heart failure) supported by chest X ray (CXR), echocardiography, electrocardiogram (ECG) or cardiac enzymes where these are available. As would be understood by a person of skill in the art, in the practice of the present invention, e.g. a method of protecting against severe dengue, said severe dengue need not be virologically-confirmed and may simply occur in the same location as other virologically-confirmed cases of dengue disease.

The terms "dengue fever virus", "dengue virus" and "DEN" are used interchangeably. They refer to positive single-strand RNA viruses belonging to the Flavivirus genus of the family of flaviviridae. There are four different serotypes of dengue virus (serotypes 1, 2, 3 and 4), which possess approximately 60-80% sequence homology. The organization of the genome comprises the following elements: a 5' non-coding region (NCR), a region encoding structural proteins (capsid (C), pre-membrane (prM) and envelope (E)) and a region encoding non-structural proteins (NS1-NS2A-NS2B-NS3-NS4A-NS4B-NS5) and a 3' NCR. The dengue viral genome encodes an uninterrupted coding region which is translated into a single polyprotein which undergoes post-translational processing.

The term "live attenuated dengue virus", as used herein, refers to a live dengue virus derived from a virulent wild-type dengue virus by genetic modification resulting in attenuation of virulence and an inability to induce a disease state characterised by the same sets of symptoms associated with the corresponding wild type dengue virus. A live attenuated dengue virus may be prepared from a wild type virus, for example, by recombinant nucleic acid technology, site directed mutagenesis, serial passages on replication competent cells, chemical mutagenesis, electromagnetic radiation or genetic manipulation such as the deletion of a small section of the viral nucleic acid. Examples of live attenuated dengue viruses useful in the practice of the present invention include VDV1 (WO 2006/134433), VDV2 (WO 2006/134443), and the strains described for example in applications WO 02/066621, WO 00/57904, WO 00/57908, WO 00/57909, WO 00/57910, WO 02/0950075 and WO 02/102828. Live attenuated dengue viruses of serotype 1 which may be used as the dengue antigen of serotype 1 in the composition of the invention include LAV1 and VDV1. Live attenuated dengue viruses of serotype 2 which may be used as the dengue antigen of serotype 2 in the composition of the invention include LAV2 and VDV2. The term "VDV" designates a live attenuated dengue virus capable of replication in Vero cells and capable of inducing a specific humoral response, including the induction of neutralizing antibodies, in a human.

The live attenuated dengue virus of serotype 1 known as 16007/PDK13, also called "LAV1", was derived from the wild-type DEN-1 (dengue virus serotype 1) 16007 strain by submitting the wild type strain to 13 passages through primary dog kidney (PDK) cells. LAV1 has been described in EP1159968 and has been filed with the National Microorganisms Cultures Collection (CNCM, Institut Pasteur, Paris, France) under number 1-2480. "VDV1" is a virus derived from LAV1 by subsequent adaptation to Vero cells; in this regard, the RNA from LAV1 has been extracted and purified before being transfected into Vero cells. The VDV1 strain has subsequently been obtained by plate purification and amplification in Vero cells. The VDV1 strain has 3 additional mutations in comparison with the DEN-1 16007/PDK13 strain. The complete nucleotide sequence of the VDV1 strain, as well as a process for preparing and characterizing the VDV1 strain have been described in international patent publication WO 2006/134433. The complete nucleic acid sequence of the VDV1 strain is as set forth in SEQ ID NO: 6.

The live attenuated dengue virus of serotype 2 known as 16681/PDK53, also called "LAV2", has been obtained from the wild-type DEN-2 (dengue virus serotype 2) 16681 strain by submitting the wild type strain to 53 passes through PDK cells. LAV2 has been described in EP1159968 and has been filed with the National Microorganisms Cultures Collection (CNCM, Institut Pasteur, Paris, France) under number 1-2481. "VDV2" is a strain derived from LAV2 by subsequent adaptation to Vero cells; in this regard, the RNA from LAV2 has been extracted and purified before being transfected in Vero cells. The VDV2 strain has subsequently been obtained by plate purification and amplification in Vero cells. The VDV2 strain has 10 additional mutations in comparison with the 16681/PDK53 strain, including 3 silent mutations and 1 mutation in a non-coding region. The complete nucleotide sequence of the VDV2 strain, as well as a process for preparing and characterizing the VDV2 strain have been described in the international patent publication WO 2006/134443. The complete nucleic acid sequence of the VDV2 strain is as set forth in SEQ ID NO: 7.

In the context of the invention, "dengue chimera" or "chimeric dengue virus" means a recipient flavivirus in which the genetic backbone has been modified by exchanging the sequence of at least the E protein of the recipient flavivirus by the corresponding sequence of a dengue virus. Alternatively, and more preferably, the genetic backbone of the recipient flavivirus is modified by exchanging the nucleic acid sequences encoding both the prM and E proteins of the recipient flavivirus by the corresponding sequences of a dengue virus. Typically, the recipient flavivirus may be attenuated. The recipient flavivirus may be a yellow fever (YF) virus, in which case, the chimera is referred to herein as a "chimeric YF/dengue virus". Preferably, the YF backbone of a chimeric YF/dengue virus according to the present invention is from an attenuated YF virus. The recipient flavivirus may also be a dengue virus and in that case, the chimeric dengue virus is referred to herein as a "chimeric dengue/dengue virus", the dengue virus serotype characteristic of the E or the prM and E proteins being identical or different from the recipient dengue virus serotype characteristic of the genetic backbone. When the recipient flavivirus is a dengue virus, said dengue virus is preferably attenuated. When the serotypes of the recipient and donor dengue viruses are identical, the recipient dengue virus and the donor dengue virus from which the prM and E protein encoding sequences originate are two different virus strains of the same serotype. For use in the present invention, chimeric dengue viruses are typically chimeric YF/dengue viruses.

In one embodiment, the chimeric YF/dengue virus comprises the genomic backbone of the attenuated yellow fever virus strain YF17D (Theiler M. and Smith H. H., 1937, J. Exp. Med., 65. 767-786). Examples of other attenuated YF strains which may be used include YF17D204 (YF-VAX®, Sanofi-Pasteur, Swiftwater, Pa., USA; Stamaril®, Sanofi-Pasteur, Marcy l'Etoile, France; ARILVAX™, Chiron, Speke, Liverpool, UK; FLAVIMUN®, Berna Biotech, Bern, Switzerland; YF17D-204 France (X15067, X15062); YF17D-204,234 US (Rice et al., 1985, Science, 229: 726-733), or the related strains YF17DD (Genbank access number U17066), YF17D-213 (Genbank access number U17067) and the strains YF17DD described by Galler et al. (1998, Vaccines, 16(9/10): 1024-1028). Advantageously, the recipient flavivirus of a live attenuated chimeric YF/dengue virus of the present invention is YF 17D or YF 17D204.

Examples of chimeric dengue viruses useful in the practice of the present invention include the chimeric YF/dengue viruses described in patent application WO 98/37911 and the chimeric dengue/dengue viruses such as those described in patent applications WO 96/40933 and WO 01/60847.

One example of a chimeric YF/dengue virus particularly suitable for use in the practice of the present invention is a Chimerivax® YF/dengue virus, which is also referred to herein as a "CYD" virus. As used herein, a Chimerivax® YF/dengue (or CYD) virus is a live attenuated chimeric YF/dengue virus which comprises the genomic backbone of a suitable attenuated YF virus (e.g. YF17D or YF17D204 (YF-VAX®)) in which the nucleic acid sequences encoding the pre-membrane (prM) and envelope (E) proteins have been replaced by nucleic acid sequences encoding the corresponding structural proteins of a dengue virus. Construction of such Chimerivax® viruses may be achieved in accordance with, or in substantial accordance with, the teaching of Chambers, et al. (1999, J. Virology 73(4): 3095-3101). The particular Chimerivax® (CYD) viruses described in WO2016/034629 have been generated by using prM and E sequences from strains DEN 1 PUO 359 (TVP1 140), DEN2 PUO 218, DEN3 PaH881/88 and DEN 4 1228 (TVP 980). For convenience, the particular Chimerivax® (CYD) viruses described in the examples of WO2016/034629 are referred to herein as "CYD1", "CYD2", "CYD3" and "CYD4". The preparation of these particular strains has been described in detail in international patent applications WO 98/37911, WO 03/101397, WO 07/021672, WO 08/007021, WO 08/047023 and WO 08/065315, to which reference may be made for a precise description of the processes for their preparation. The nucleotide sequences of the prM-E regions of CYD1, CYD2, CYD3 and CYD4 are set out in WO2016/034629 and in the enclosed sequence listing. Alternatively, other dengue fever virus strains may be used as a source of nucleic acids to facilitate construction of chimeric viruses useful in the practice of the present invention, as described elsewhere herein, for example in the construction of other Chimerivax® YF/Dengue viruses. An alternative embodiment of chimeric dengue virus usable in the method of protection of the invention is a recipient flavivirus in which the genetic backbone has been modified by exchanging (i) the sequence encoding the E protein of the recipient flavivirus by the corresponding sequence of a dengue virus and (ii) the sequence encoding the prM protein of the recipient flavivirus by the corresponding sequence of a non-dengue flavivirus, e.g. a JEV virus. Examples of such chimeric dengue viruses are described in WO 2011/138586.

The term "dengue virus-like particle" or "dengue VLP", as used herein, refers to a virus particle that does not contain replicative genetic material but presents at its surface a dengue E protein in a repetitive ordered array similar to the native virion structure. Typically, dengue VLPs also contain dengue prM and/or M proteins. VLPs may be produced in vitro (Zhang et al, J. Virol. (2011) 30 (8):333). VLPs may also be produced in vivo. To that end, a nucleic acid construct or constructs (e.g. DNA or RNA) encoding prM/M and E dengue proteins may be introduced into a cell of a subject, e.g. a human subject, via methods known in the art, e.g. via use of at least one viral vector. The VLP particles are then formed in vivo. Non-limiting examples of viral vectors that may be used in the method of the present invention include the poxviruses (e.g. the attenuated pox Ankara virus) and the measles virus. For use in the present invention, a particular category of viral vector expressing VLPs in vivo includes replication-deficient pseudoinfectious (PIV) viruses, e.g. according to the Replivax™ technology. (Rumyantsev A A, et al. Vaccine. 2011 Jul. 18; 29(32):5184-94).

The ability of a vaccine composition of the present invention to provoke an immune response in a subject (i.e. induce the production of neutralizing antibodies) can be assessed, for example, by measuring the neutralizing antibody titre raised against the dengue virus serotype(s) comprised within the composition. The neutralizing antibody titre may be measured by the Plaque Reduction Neutralization Test ($PRNT_{50}$) test (Timiryasova, T. M. et al., Am. J. Trop. Med. Hyg. (2013), vol. 88(5), 962-970). Briefly, neutralizing antibody titre is measured in sera collected from subjects to be tested for their level of dengue neutralising antibodies. If the subject is a vaccinated subject, a sample is collected from said subject at least 28 days following administration of a vaccine composition of the present invention. Serial, two-fold dilutions of the sera (previously heat-inactivated) are mixed with a constant challenge-dose of each dengue virus of serotype 1, 2, 3 or 4 as appropriate (expressed as PFU/mL). The parental dengue virus strains of the CYD dengue vaccine constructs are used as the challenge strains. The mixtures are then inoculated into wells of a microplate with confluent Vero cell monolayers. After adsorption, cell monolayers are incubated for a few days. The presence of dengue virus infected cells is indicated by the formation of infected foci (i.e. plaques) and a reduction in virus infectivity due to the presence of neutralising antibodies in the serum samples (i.e. a reduction in the number of plaques) can thus be detected. The reported value (end point neutralization titre) represents the highest dilution of serum at which 50% of dengue challenge virus (in plaque counts) is neutralized when compared to the mean viral plaque count in the negative control wells (which represents the 100% virus load). The end point neutralization titres are presented as continuous values. The lower limit of quantification (LLOQ) of the assay is 10 (1/dil). It has been commonly considered that seroconversion occurs when the titre is superior or equal to 10 (1/dil). As PRNT tests may slightly vary from a laboratory to another the LLOQ may also slightly vary. Accordingly, in a general manner, it is considered that seroconversion occurs when the titre is superior or equal to the LLOQ of the test. However, as an alternative, a higher cut-off for determining seroconversion (i.e. a positive result) may be used in the context of the $PRNT_{50}$, for example, 25 (1/dil), 50 (1/dil), 75 (1/dil) or 100 (1/dil). As a further alternative to $PRNT_{50}$, it may be preferable to use the more stringent $PRNT_{90}$ test to assess the presence of neutralizing antibodies against dengue. Use of the $PRNT_{90}$ may be especially preferable to assess the level of neutralising antibodies in samples obtained from subjects resident in dengue endemic areas, since the $PRNT_{90}$ test is more specific than the $PRNT_{50}$ test.

In accordance with the invention, the "seroconversion rate after a booster vaccination" of dengue vaccine refers to the percentage of subjects with either a pre-booster neutralizing antibody titer below titer 10 (1/dil) and a post-booster titer above 40 (1/dil), or a pre-booster titer above 10 (1/dil) and at least a 4-fold increase in post-booster titer as determined by $PRNT_{50}$ (Plaque Reduction Neutralization Test) immediately prior and 28 days post-booster injection, for each of the four dengue virus serotypes.

The term "$CCID_{50}$" refers to the quantity of virus (e.g. vaccinal virus) infecting 50% of the cell culture. The $CCID_{50}$ assay is a limit dilution assay with statistical titer calculation (Morrison D et al, J Infect Dis. 2010; 201(3): 370-7)).

As used herein, a "dengue naïve", "dengue non-immune" or "dengue seronegative" subject refers to a subject who has not been infected by a dengue virus nor previously immunized with a dengue vaccine, i.e. a serum sample taken from said subject would produce a negative result in a dengue ELISA or $PRNT_{50}$ assay. An example of a dengue ELISA would be the Panbio® Dengue IgG Indirect ELISA available from Alere/Abbott. Assessment of the dengue serostatus of a subject is preferably assessed using a $PRNT_{50}$ assay. In respect of the $PRNT_{50}$ assay, a serum sample from a "dengue naïve", "dengue non-immune" or "dengue seronegative" subject would produce a result below the LLOQ of the assay.

As used herein, a "dengue immune" or "dengue seropositive" subject refers to a subject who has been infected by a dengue virus or immunized by a dengue vaccine before administration of the vaccine composition of the present invention, i.e. a serum sample taken from said subject would produce a positive result in a dengue ELISA or $PRNT_{50}$ assay. An example of a dengue ELISA would be the Panbio® Dengue IgG Indirect ELISA available from Alere/Abbott. Assessment of the dengue serostatus of a subject is preferably assessed using a $PRNT_{50}$ assay. In respect of the $PRNT_{50}$ assay, a serum sample from a "dengue immune" or "dengue seropositive" subject would produce a result above the LLOQ of the assay.

In accordance with the present invention, a "method of protecting", as used herein, results in a reduction in the severity or in the likelihood of developing dengue disease in a human subject exposed to a dengue virus. Advantageously, said reduction is statistically significant. A method of protecting, according to the present invention, may result in any one or more of the following:
  (i) a statistically significant reduction in the incidence or likelihood of, e.g. the prevention of, dengue disease caused by a dengue virus of serotype 1, dengue disease caused by a dengue virus of serotype 2, dengue disease caused by a dengue virus of serotype 3 and/or dengue disease caused by a dengue virus of serotype 4;
  (ii) prevention of dengue disease, regardless of severity, caused by serotypes 1, 2, 3 and 4;
  (iii) a statistically significant reduction in the incidence or likelihood of, e.g. the prevention of, severe dengue disease caused by a dengue virus of serotype 1, severe dengue disease caused by a dengue virus of serotype 2, severe dengue disease caused by a dengue virus of serotype 3 and/or severe dengue disease caused by a dengue virus of serotype 4;
  (iv) a reduction in the incidence or likelihood of, e.g. the prevention of, DHF caused by a dengue virus of serotype 1, DHF caused by a dengue virus of serotype 2, DHF caused by a dengue virus of serotype 3 and/or DHF caused by a dengue virus of serotype 4; preferably said reduction is statistically significant;
  (v) a statistically significant reduction in the incidence or likelihood of, e.g. the prevention of, hospitalization due to: dengue disease caused by a dengue virus of serotype 1; dengue disease caused by a dengue virus of serotype 2; dengue disease caused by a dengue virus of serotype 3 and/or dengue disease caused by a dengue virus of serotype 4;
  (vi) a statistically significant reduction in the incidence or likelihood, e.g. the prevention of, repeated symptomatic virologically-confirmed dengue cases due to any serotype, defined as ≥2 episodes of dengue due to different serotypes occurring more than 14 days apart.

(vii) any one of (i) to (vi) in human subjects who are at least 5 years of age;

(viii) any one of (i) to (vi) in human subjects who are at least 7 years of age;

(ix) any one of (i) to (vi) in human subjects who are at least 9 years of age;

(x) any one of (i) to (vi) in human subjects who are at least 11 years of age;

(xi) any one of (i) to (vi) in human subjects who are at least 12 years of age;

(xii) any one of (i) to (vi) in human subjects who are between 9 and 16 years of age;

(xiii) any one of (i) to (vi) in human subjects who are between 12 and 16 years of age;

(xiv) prevention of dengue disease caused by dengue virus serotypes 1, 2, 3 and 4 in individuals 9 through 60 years of age living in endemic areas;

(xv) prevention of dengue disease caused by dengue virus serotypes 1, 2, 3 and 4 in individuals 12 through 60 years of age living in endemic areas.

(xvi) prevention of dengue disease caused by dengue virus serotypes 1, 2, 3 and 4 in individuals 9 through 45 years of age living in endemic areas;

(xvii) prevention of dengue disease caused by dengue virus serotypes 1, 2, 3 and 4 in individuals 12 through 45 years of age living in endemic areas;

As used herein, a homotypic neutralizing antibody against dengue virus refers to an antibody that binds epitopes that are unique to a single serotype of dengue virus and does not cross-react with epitopes of the 3 other serotypes. A heterotypic neutralizing antibody refers to an antibody that binds to epitopes that are conserved between at least 2 serotypes of dengue virus, such an antibody is thus a serotype cross-neutralizing antibody.

DETAILED DESCRIPTION OF THE PRESENT INVENTION

The present inventors have demonstrated that the administration of a booster dengue vaccine unexpectedly induces an increase of the neutralizing antibody titres in subjects who were dengue naïve before the primary vaccination, which is proportionally greater than the increase in subjects who were dengue immune before said primary vaccination. Whereas the immune response to primary vaccination against dengue virus is more effective in human subjects who are dengue immune prior to the primary vaccination, the inventors have now demonstrated that the degree of modulation of the immune response to a booster vaccination is modest in this population, with respect to human subjects who have not been infected (i.e. who were dengue naïve prior to the primary vaccination) for which the degree of modulation is unexpectedly high.

According to a first aspect, the present invention thus relates to a method of booster vaccination and to a vaccine composition for use in such a method for inducing in a human subject an immune response, wherein said subject has previously received a primary vaccination against each of serotypes 1 to 4 of dengue virus and was dengue naïve before said primary vaccination, preferably was flavivirus naïve before said primary vaccination. Such a subject has preferably not previously been naturally infected by a dengue virus, and preferably not previously been naturally infected by a flavivirus.

The method of booster vaccination according to the invention comprises the step of administering the vaccine composition to the human subject.

The immune response induced by the vaccine composition of the invention or by the method of the invention is preferably a humoral response, especially a response comprising the production of neutralizing antibodies against dengue virus, i.e. a neutralizing antibody response. According to a preferred embodiment, the neutralizing antibodies are directed against each of serotypes 1 to 4 of dengue virus.

In a preferred embodiment, the method of booster vaccination and the vaccine composition for use as a booster according to this aspect of the invention induces at least a two-fold increase in the titers of neutralizing antibodies in the subjects receiving the booster, for at least one of the dengue serotypes, preferably for at least two, most preferably for at least 3, and even more preferably for each of serotypes 1 to 4, by comparison to the titers of neutralizing antibodies before the booster administration. Preferably the comparison is made between the levels measured a few days before the booster administration and around 28 days or one month after its administration. Alternatively, the level after the booster administration is measured around one or two months after said administration, preferably between around 20 days and 60 days after said booster vaccination, especially around 28 days after said booster vaccination. The titre of neutralizing antibodies is advantageously measured by the $PRNT_{50}$ test. The neutralizing antibody titre is thus advantageously assimilated to the $PRNT_{50}$ titre in the following.

In another preferred embodiment, the vaccine composition for use as a booster and the corresponding method according to this aspect of the invention induces at least a four-fold increase in the titres of neutralizing antibodies in a human subject receiving the booster, for at least one of the dengue serotypes, preferably for at least two dengue serotypes, or more, preferably for at least serotype 4, or for serotypes 3 and 4.

The present inventors have also demonstrated that such a booster vaccination unexpectedly induces a seroconversion rate after the booster, for each serotype of the dengue virus, which is greatly increased in subjects who were dengue non-immune before the primary vaccination, with respect to the seroconversion rate in subjects who were dengue immune before the primary vaccination, by a factor of at least 2 to 5 (see table 8 of the experimental section). According to a preferred embodiment, the seroconversion rate after the booster vaccination according to the invention, in human subjects who have previously received a primary vaccination against each of serotypes 1 to 4 of dengue virus but who were dengue naïve before said primary vaccination, is at least about 30% for each serotype, preferably at least 35% for serotype 1 or at least 35% for serotype 2, at least 45% for serotype 3. The seroconversion rate after a booster vaccination is preferably estimated on a population of at least 10 different human subjects receiving the booster vaccination, preferably on a population of at least 50 subjects, even more preferably on a population of at least 100 subjects.

The inventors have demonstrated that, not only is the seroconversion rate of the booster vaccination increased in subjects who were dengue non-immune before the primary vaccination, with respect to the seroconversion rate in subjects who were dengue immune before the primary vaccination, but also that the relative rate of decline in the titre of neutralizing antibodies is lower in subjects who were dengue non-immune before the primary vaccination, with respect to the relative rate of decline in subjects who were dengue immune before the primary vaccination. Indeed, as illustrated in table 15, one year after the booster vaccination, the additive effect of the booster dose, on the titre of neutralizing antibodies, is still present in baseline naïve subjects and has disappeared in baseline immune subjects. The additive effect of the booster dose is thus more durable in baseline naïve subjects than in baseline immune subjects. More specifically, one year after the booster vaccination or more, the titre of neutralizing antibodies in the subjects receiving the booster is preferably still increased with respect to the level before the booster vaccination, preferably by a factor of at least 1.2, or at least 1.3 or more, in dengue-naïve subjects before the primary vaccination. Such an increased titre over at least one year after the booster vaccination is for at least one serotype, preferably at least two or three, preferably for the 4 serotypes.

The vaccine composition for use in a booster vaccination according to the invention is for use in a human subject who has previously been vaccinated against dengue disease, and was flavivirus naïve before said primary vaccination. Preferably, the subject has not been naturally infected by a flavivirus, i.e. has not been infected by a flavivirus before the booster vaccination. Preferably the subject has not been previously naturally infected by a yellow fever virus, a dengue virus, irrespective of the serotype, or a Zika virus. Even more preferably, the subject to receive the booster vaccination has not been naturally infected by a dengue virus or a Zika virus. Most preferably, the human subject has not previously been naturally infected by a dengue virus, irrespective of the serotype. Before the primary vaccination, a human subject was thus dengue naïve, preferably dengue naïve and Zika naïve and even more preferably yellow fever naïve, dengue naïve and Zika naïve.

A preferred human subject is thus a subject who has, before the administration of the booster, a $PRNT_{50}$ titre against each of serotypes 1 to 4 of at least 10, (i.e. the subject is dengue immune due to the primary vaccination), but who has a $PRNT_{50}$ titre of less than 150, preferably less than 120, or preferably less than 100, preferably less than 80, preferably less than 60, preferably less than 40 or even less than 30, indicating that the subject has not been naturally infected by a dengue virus and was dengue naïve prior to the primary vaccination.

The absence of a prior natural infection by a dengue virus can also been confirmed by the absence of detection of antibodies against dengue virus antigens which may not be present in a dengue vaccine, for example antibodies against dengue non-structural protein 1 (NS1) antigen, which is absent from at least Dengvaxia®. Various tests for detecting antibodies against dengue NS1 protein are well known in the art.

A subject likely to be treated by the method of the invention, i.e. a subject who has received a primary vaccination but who has not been naturally infected, or a subject who was dengue naïve before the primary vaccination, is also characterized by the type or quality of neutralizing antibodies present in the subject. Such a subject is for example characterized as exhibiting an essentially homotypic neutralizing antibody response against only one of the 4 serotypes, and a mixed homotypic and heterotypic neutralizing antibody response against the 3 other serotypes. Preferably, the subject to be treated according to this $1^{st}$ aspect exhibits an essentially homotypic neutralizing antibody response against dengue virus serotype 4, and a mixed homotypic and heterotypic neutralizing antibody response against dengue virus serotypes 1-3.

The previous dengue infection according to the present invention may be virologically-confirmed dengue disease.

The vaccine composition according to the invention comprises a dengue antigen of at least one of serotypes 1 to 4 or a nucleic acid construct capable of expressing said antigen(s) in the subject. According to a preferred embodiment, the vaccine composition comprises:
  (i) a dengue antigen of at least one of serotypes 1 to 4, wherein said dengue antigen(s) of at least one of serotypes 1 to 4 is (are each independently) selected from the group consisting of:
    (a) a live attenuated dengue virus; and
    (b) a live attenuated chimeric dengue virus;
  or
  (ii) a nucleic acid construct(s) which is (are) able to express in said human subject a dengue antigen of at least one of serotypes 1 to 4, wherein said dengue antigen(s) is (are) dengue VLPs.

According to a preferred embodiment, the vaccine composition comprises:
  (i) a dengue antigen of each of serotypes 1 to 4, wherein said dengue antigens of each of serotypes 1 to 4 are each independently selected from the group consisting of:
    (a) a live attenuated dengue virus; and
    (b) a live attenuated chimeric dengue virus;
  or
  (iii) a nucleic acid construct or constructs which is (are) able to express in said human subject a dengue antigen of each of serotypes 1 to 4, wherein said dengue antigens are dengue VLPs.

According to another embodiment, the vaccine composition comprises a dengue antigen, or nucleic acid able to express a dengue antigen, of least 2 serotypes, preferably at least 3 serotypes, for example serotypes 1, 2 and 4.

Preferably a vaccine composition according to the present invention comprises a dengue antigen of each of serotypes 1 to 4 which are each independently selected from the group consisting of: (a) a live attenuated dengue virus and (b) a live attenuated chimeric virus.

Preferably a vaccine composition according to the present invention comprises a dengue antigen of at least one, two, three or each of serotypes 1 to 4, wherein at least one of said dengue antigens is a live attenuated chimeric virus, preferably a live attenuated chimeric dengue virus, even more preferably a live attenuated chimeric dengue/dengue virus or a live attenuated chimeric YF/dengue virus. For example, the dengue antigen of serotype 2 is a live attenuated chimeric dengue/dengue virus. For example, a vaccine composition according to the present invention may be any of the tetravalent mixtures of dengue antigens of each of serotypes 1 to 4 (referred to as TV001, TV002, TV003 and TV004) which are disclosed in Durbin et al., Journal of Infectious Diseases (2013), 207, 957-965. Preferably, a vaccine composition according to this embodiment of the invention is TV003.

Preferably a vaccine composition according to the present invention comprises a dengue antigen of at least one, two, three or each of serotypes 1 to 4, wherein said dengue antigens are each a live attenuated chimeric dengue virus. For example, a vaccine composition of the present invention may comprise a dengue antigen of each of serotypes 1 to 4, wherein said dengue antigens of serotypes 1, 3 and 4 are each a live attenuated chimeric dengue/dengue virus and said dengue antigen of serotype 2 is a live attenuated dengue virus. For example, a vaccine composition according to the present invention may be the tetravalent mixture of dengue antigens of each of serotypes 1 to 4 (referred to as DENVax) which is disclosed in Huang et al., PLoS Negl Trop Dis 7(5): e2243 (2013). Alternatively, a vaccine composition of the present invention may comprise a dengue antigen of each of serotypes 1 to 4, wherein said dengue antigens of serotypes 1, 3 and 4 are each a live attenuated chimeric YF/dengue virus and said dengue antigen of serotype 2 is a live attenuated dengue virus.

Preferably a vaccine composition according to the present invention comprises a dengue antigen of each of serotypes 1 to 4, wherein each of said dengue antigens is a live attenuated chimeric dengue virus, preferably a chimeric YF/dengue virus, more preferably a chimeric YF/dengue virus which comprises an attenuated YF genomic backbone whose prM-E sequence has been substituted with the prM-E sequence of dengue virus.

Preferably, a live attenuated chimeric dengue virus of the present invention comprises one or more proteins from a dengue virus and one or more proteins from a different flavivirus. Preferably, the different flavivirus is a yellow fever virus (i.e. a chimeric YF/dengue virus). Preferably a live attenuated chimeric dengue virus according to the present invention comprises an attenuated yellow fever virus genome whose prM-E sequence has been substituted with the prM-E sequence of a dengue virus. Alternatively, a live attenuated chimeric dengue virus of the present invention comprises one or more proteins from a first dengue virus and one or more proteins from a second dengue virus (i.e. a chimeric dengue/dengue virus). Preferably said first dengue virus and said second dengue virus are of different serotypes. Where said first dengue virus and said second dengue virus are of the same serotype, said first and second dengue viruses are different strains.

A preferred example of a dengue antigen of serotype 1 for use in the present invention is a live attenuated chimeric YF/dengue virus which comprises a nucleotide sequence having at least 90%, at least 95%, at least 98% or 100% sequence identity to SEQ ID NO: 1. Another preferred example of a dengue antigen of serotype 1 for use in the present invention is a live attenuated dengue virus which comprises a nucleotide sequence having at least 90%, at least 95%, at least 98% or 100% sequence identity to SEQ ID NO: 6. Preferably a nucleotide sequence that has less than 100% identity to SEQ ID NO: 6 does not comprise mutations at the positions within said nucleic acid sequence which correspond to positions 1323, 1541, 1543, 1545, 1567, 1608, 2363, 2695, 2782, 5063, 5962, 6048, 6806, 7330, 7947 and 9445 of SEQ ID NO: 6.

A preferred example of a dengue antigen of serotype 2 for use in the present invention is a live attenuated chimeric YF/dengue virus which comprises a nucleotide sequence having at least 90%, at least 95%, at least 98% or 100% sequence identity to SEQ ID NO: 2. Another preferred example of a dengue antigen of serotype 2 for use in the present invention is a live attenuated chimeric YF/dengue virus which comprises a nucleotide sequence having at least 90%, at least 95%, at least 98% or 100% sequence identity to SEQ ID NO: 5. Another preferred example of a dengue antigen of serotype 2 for use in the present invention is a live attenuated dengue virus which comprises a nucleotide sequence having at least 90%, at least 95%, at least 98% or 100% sequence identity to SEQ ID NO: 7. Preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7.

Advantageously, a dengue antigen of serotype 2 for use in the present invention (whether said dengue antigen is, for example, a live attenuated dengue virus, a chimeric dengue virus or a VLP) comprises a Thr residue at position E-226 and/or a Val residue at position E-251. More advantageously, said dengue antigen of serotype 2 comprises a Thr residue at position E-226, a Gly residue at position E-228 and a Val residue at position E-251 In this context, E-226 designates position 226 of the Envelope (E) protein etc. The identity of an amino acid residue at a particular position can easily be determined by protein alignment, for example by alignment with the protein sequence of the E protein from CYD2, which may be easily derived from SEQ ID NO: 2.

A preferred example of a dengue antigen of serotype 3 for use in the present invention is a live attenuated chimeric YF/dengue virus which comprises a nucleotide sequence having at least 90%, at least 95%, at least 98% or 100% sequence identity to SEQ ID NO: 3.

A preferred example of a dengue antigen of serotype 4 for use in the present invention is a live attenuated chimeric YF/dengue virus which comprises a nucleotide sequence having at least 90%, at least 95%, at least 98% or 100% sequence identity to SEQ ID NO: 4.

In order to form a tetravalent dosage form of a booster composition for use according to the present invention (i.e. one containing a dengue antigen of each of serotypes 1 to 4), the preferred examples of dengue antigens of serotypes 1, 2, 3 and 4 disclosed in the preceding four paragraphs may be combined in any combination possible. Alternatively, a booster composition for use according to the present invention may be administered to a subject as bivalent dosage forms, or tetravalent dosage forms, wherein the preferred examples of dengue antigens of serotypes 1, 2, 3 and 4 disclosed in the preceding four paragraphs may be combined in any pair of bivalent or tetravalent combinations that are possible. Thus, in particularly preferred combinations of dengue antigens of serotypes 1, 2, 3 and 4, the dengue antigens of serotypes 3 and 4 are respectively a live attenuated chimeric YF/dengue virus which comprises a nucleotide sequence having at least 90%, at least 95%, at least 98% or 100% sequence identity to SEQ ID NO: 3 and a live attenuated chimeric YF/dengue virus which comprises a nucleotide sequence having at least 90%, at least 95%, at least 98% or 100% sequence identity to SEQ ID NO: 4. In such particularly preferred combinations, the dengue antigens of serotypes 1 and 2 may respectively be:

(i) a live attenuated chimeric YF/dengue virus which comprises a nucleotide sequence having at least 90%, at least 95%, at least 98% or 100% sequence identity to SEQ ID NO: 1 and a live attenuated chimeric YF/dengue virus which comprises a nucleotide sequence having at least 90%, at least 95%, at least 98% or 100% sequence identity to SEQ ID NO: 2; or (ii) a live attenuated chimeric YF/dengue virus which comprises a nucleotide sequence having at least 90%, at least 95%, at least 98% or 100% sequence identity to SEQ ID NO: 1 and a live attenuated chimeric YF/dengue virus which comprises a nucleotide sequence having at least 90%, at least 95%, at least 98% or 100% sequence identity to SEQ ID NO: 5; or (iii) a live attenuated chimeric YF/dengue virus which comprises a nucleotide sequence having at least 90%, at least 95%, at least 98% or 100% sequence identity to SEQ ID NO: 1 and a live attenuated dengue virus which comprises a nucleotide sequence having at least 90%, at least 95%, at least 98% or 100% sequence identity to SEQ ID NO: 7 (preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7); or (iv) a live attenuated dengue virus which comprises a nucleotide sequence having at least 90%, at least 95%, at least 98% or 100% sequence identity to SEQ ID NO: 6 (preferably a nucleotide sequence that has less than 100% identity to SEQ ID NO: 6 does not comprise mutations at the positions within said nucleic acid sequence which correspond to positions 1323, 1541, 1543, 1545, 1567, 1608, 2363, 2695, 2782, 5063, 5962, 6048, 6806, 7330, 7947 and 9445 of SEQ ID NO: 6 and a live attenuated dengue virus which comprises a nucleotide sequence having at least 90%, at least 95%, at least 98% or 100% sequence identity to SEQ ID NO: 7 (preferably a nucleotide sequence that has less than 100% identity to SEQ ID NO: 7 does not comprise mutations at the positions within said nucleic acid sequence which correspond to positions 736, 1619, 4723, 5062, 9191, 10063, 10507, 57, 524, 2055, 2579, 4018, 5547, 6599 and 8571 of SEQ ID NO: 7).

The vaccine composition for use according to this $1^{st}$ aspect of the invention, as a booster vaccination, may advantageously be identical to the vaccine composition previously administered during the primary vaccination course. Alternatively, according to a different embodiment, the vaccine composition for use as a booster vaccination, may be different from the vaccine composition previously administered during the primary vaccination course. It may inter alia comprise antigen of only one serotype whereas the primary vaccination comprises antigens of each of serotypes 1-4; it may also comprise different excipients, different dosages. It may also be an entirely different vaccine composition; for example the primary vaccination is based on live attenuated chimeric dengue/dengue viruses, and the booster vaccination is based on live attenuated chimeric YF/dengue viruses.

According to a second aspect, the present invention is directed to a method of inducing in a human subject a neutralizing antibody response against dengue virus, and to a vaccine composition for use in such a method, said composition comprising a dengue antigen of each of serotypes 1 to 4, or a nucleic acid construct capable of expressing in said subject a dengue antigen of each of serotypes 1 to 4; wherein said composition is administered as:

(a) a primary vaccination, followed by
(b) a booster vaccination, and wherein the human subject is initially dengue naïve.

The method of inducing in a human subject a neutralizing antibody response against dengue virus according to this second aspect comprises the steps of (a) administering a vaccine composition as a primary vaccination, and of (b) subsequently administering a vaccine composition (which may be the same or different as the primary vaccination composition) as a booster vaccination.

Preferably, the dengue antigens of serotypes 1 to 4 are each independently selected from the group consisting of a live attenuated dengue virus and a live attenuated chimeric dengue virus.

Alternatively, the vaccine composition for use according this second aspect of the invention comprises one or more nucleic acid constructs capable of expressing dengue VLPs of each of serotypes 1 to 4.

All the preferred types and combinations of antigens of serotypes 1 to 4 detailed with regard to the first aspect of the invention are entirely applicable to this second aspect of the invention; inter alia, according to a preferred embodiment, the dengue antigens of serotypes 1 to 4 are each independently live attenuated chimeric dengue viruses, especially they are each independently selected from the group consisting of live attenuated chimeric dengue/dengue and YF/dengue viruses. According to preferred embodiments, the dengue antigens of serotypes 1 to 4 are all live attenuated chimeric dengue/dengue viruses, or they are all live attenuated chimeric YF/dengue viruses.

Preferably, said immune response comprising the production of neutralizing antibodies against dengue virus, or said neutralizing antibody response, according to the first and second aspects of the invention results in a certain level of vaccine efficacy, preferably it is protecting the human subject against dengue disease caused by a dengue virus of at least one of serotype 1, 2, 3 and 4, and most preferably against the four serotypes. For example, a vaccine composition for use in a booster vaccination according to the present invention results in a vaccine efficacy (after booster) in respect of dengue disease caused by any serotype (in a human subject as defined herein) of at least 30%, more preferably at least 40%, more preferably at least 50%, more preferably 60% and even more preferably 70%. For example, a vaccine composition for use in a booster vaccination according to the present invention results in a vaccine efficacy (after booster) in respect of dengue disease caused by serotype 1, serotype 2, serotype 3 or serotype 4 (in a human subject as defined herein) of at least 30%, more preferably at least 40%, more preferably at least 50%, more preferably 60% and even more preferably 70%.

Preferably, said dengue disease caused by a dengue virus is severe dengue disease. Preferably, the method of the invention results in a reduction in the incidence or likelihood of hospitalisation due to dengue disease caused by a dengue virus, irrespective of the dengue virus serotype. Preferably, said dengue disease caused by a dengue virus is DHF.

A vaccine composition according to the $1^{st}$ aspect of the present invention is administered as a booster to a human subject who has already received a primary vaccination regimen against dengue virus; the vaccine composition is thus administered to a human subject who is preferably at least 2 years old. Preferably said human subject is at least 5 years old. Preferably said human subject is at least 7 years old, even more preferably said human subject is at least 9 years old.

Most preferably, especially when the primary vaccination consists in a 3-dose regimen, administered around 6 months apart from each other, the human subject to be administered the booster dose according to the $1^{st}$ aspect of the invention, is at least 10 years old, or even more preferably 11 years old. Preferably said human subject is at least 11 or 12 years old.

The vaccine composition according to the $1^{st}$ aspect is administered to a subject who is preferably less than 62 years old, preferably less than 55, and even more preferably less than 47 years old. A preferred subject according to this aspect of the invention is thus aged between 2 years and 62 years, preferably between 5 years and 55 years, and more preferably between 11 years and 47 years.

A vaccine composition according to the $2^{nd}$ aspect of the invention, which is to be administered as a primary vaccination followed by a booster vaccination, is to be administered to a human subject who is preferably at least 9 months old. Preferably said human subject is at least 2 years old, or 4 or 5 years old. Preferably said human subject is at least 7 years old, even more preferably said human subject is at least 9 years old.

The vaccine composition according to the $2^{nd}$ aspect is administered to a subject who is preferably less than 60 years old, preferably less than 55, and even more preferably less than 45 years old. A preferred subject according to this aspect of the invention is thus aged between 9 months and 60 years, preferably between 4 years and 55 years, and more preferably between 9 years and 45 years Alternatively, according to both aspects of the invention, said human subject is aged between 2 and 60 years old. Preferably said human subject is aged between 10 and 60 years old, for example between 10 and 50 years old. According to a preferred embodiment, said human subject is aged between 11 and 50 years old. According to an even more preferred embodiment, the subject is aged between 12 and 45 years old, for example between 12 and 30 years old.

A human subject according to the present invention is preferably not pregnant, lactating or of childbearing potential, does not have self-reported or suspected congenital or acquired immunodeficiency, has not been in receipt of immunosuppressive therapy within the 6 months prior to vaccination or systemic corticosteroids therapy for more than 2 weeks within the 3 months prior to vaccination, is not HIV seropositive and does not have systemic hypersensitivity to any of the vaccine components as defined herein.

A vaccine composition of the present invention is administered as a booster vaccination, or as a primary vaccination followed by a booster vaccination, to a human subject who is yellow fever immune or yellow fever naïve, preferably yellow fever naïve. As used herein, a yellow fever immune subject refers to a subject who has been infected by a YF virus or immunized by a YF vaccine before administration of the primary vaccination or booster composition of the present invention, i.e. a serum sample taken from said subject will produce a positive result in a YF ELISA or YF $PRNT_{50}$ assay. Conversely, a yellow fever naïve subject refers to a subject who has not been infected by a YF virus or immunized by a YF vaccine before administration of the vaccine or booster composition of the invention, i.e. a serum sample taken from said subject will produce a negative result in a YF ELISA or YF $PRNT_{50}$ assay. Briefly, a YF $PRNT_{50}$ assay is carried out as follows. Serial two-fold dilutions of serum to be tested (previously heat-inactivated) are mixed with a constant concentration of the YF vaccinal strain 17D (expressed as PFU/mL). The mixtures are inoculated in duplicate into wells of a plate of confluent Vero cells. After adsorption, cell monolayers are overlaid and incubated for a few days. The reported value (end point neutralization titre) represents the highest dilution of serum at which ≥50% of YF challenge virus (in plaque counts) is neutralized when compared to the negative control wells, which represents the 100% virus load. The LLOQ for the YF $PRNT_{50}$ assay is 10 (1/dil).

Preferably a vaccine composition of the present invention is administered as a booster vaccination to a human subject who is yellow fever naïve and dengue immune, more specifically to a subject who has not been infected by a YF or dengue virus, has not been immunized by a YF vaccine but has been immunized by a dengue vaccine before administration of the booster composition of the present invention.

The primary vaccination course according to both aspects of the present invention may be administered in one dose or in multiple doses, for example in one, two or three doses. When the primary vaccination consists in three doses, the first dose and the third dose are preferably administered approximately twelve months apart. For instance, a primary vaccination may consist in a first dose, a second dose and a third dose, wherein said second dose is to be administered about six months after said first dose and wherein said third dose is to be administered about twelve months after said first dose. Alternatively, the three doses may be administered at zero months, at about three to four months (e.g. at about three-and-a-half months) and at about twelve months (i.e. a regimen wherein the second dose of the primary vaccination is administered at about three-and-a-half months after the first dose, and wherein the third dose of the primary vaccination is administered at about twelve months after the first dose).

A primary vaccination according to both aspects of the present invention may consist in two doses. Preferably, the first dose and the second dose are administered approximately about three, six, eight or nine months apart. Preferably, the second dose is administered about six months after the first dose. Alternatively, two doses may be administered to a subject simultaneously or almost simultaneously (e.g. within 24 hours of each other).

A primary vaccination according to both aspects of the present invention may also consist of a single dose.

The booster vaccination according to the invention may also be administered in one or several doses, preferably in one, two or three doses. All the different variations disclosed above with respect to the primary vaccination apply mutatis mutandis to the booster vaccination. According to a preferred embodiment, the vaccine composition of the invention is administered as a single booster dose.

Preferably, according to the present invention, the vaccine composition administered as a booster vaccination is to be administered at least one year after the end of the primary vaccination course, i.e. the first dose of the booster is administered at least one year after administration of the last dose scheduled in the initial immunization regimen, more preferably at least two years after the primary vaccination course, and even more preferably around 4 to 6 years after the primary vaccination.

According to a preferred embodiment, the booster vaccination is administered less than 20 years after the end of the primary vaccination, i.e. the first dose of the booster is administered less than 20 years after administration of the last dose scheduled in the initial immunization regimen. For example, the booster administration is administered between 1 year and 20 years after the end of the primary vaccination course, preferably between 1.5 and 15 years after the end, more preferably between 2 years and 10 years after the end of the primary vaccination course. More preferably, the booster vaccination is administered between around 4 years after the end of the primary vaccination and about 8 years, more preferably around 4 to 5 years after the end of the primary vaccination.

In the context of the present invention, the booster vaccination may also advantageously be repeated, i.e. administered more than once, for example twice, or three times. Preferably the booster vaccination is repeated around every 4 or 5 years after the first booster vaccination, or every 7 years, or every 10 years.

A human subject according to the present invention (to which a vaccine composition is administered as a booster) is preferably resident in or travelling to a dengue endemic area. More preferably, said human subject is resident in a dengue endemic area. A human subject according to the present invention may also be resident in an area that is experiencing a dengue epidemic. The term resident is given its conventional meaning herein and refers to a person who is normally domiciled in the area in question. Dengue endemic areas are well-known to a person of skill in the art and include, according to the present invention, most of the tropics and sub-tropics, for instance any country identified as an endemic country by the WHO. For instance, a dengue endemic area according to the present invention may comprise those American countries or parts thereof which fall within the tropics and sub-tropics. A dengue endemic area according to the present invention may thus comprise any one or more of the following countries or parts thereof: Brazil, Venezuela, Colombia, Ecuador, Peru, Bolivia, Paraguay, Panama, Costa Rica, Nicaragua, Honduras, El Salvador, Guatemala, Belize, Mexico, the USA and the islands of the Caribbean. In a particular embodiment, a dengue endemic area of the present invention may consist of the following: Brazil, Colombia, Honduras, Mexico and Puerto Rico. In another particular embodiment, a dengue endemic area of the present invention may consist of the following: Brazil, Colombia and Honduras. A dengue endemic area according to the present invention may also include south Asian and Oceania countries within the tropics and sub-tropics. A dengue endemic area according to the present invention may thus consist of any one or more of the following: India, Myanmar (Burma), Thailand, Laos, Viet Nam, Cambodia, Indonesia, Malaysia, Singapore, the Philippines, Taiwan, Papua New Guinea and Australia. A dengue endemic area according to the present invention, (which may be national or subnational), is an area where epidemiological data indicate a high burden of disease. For example, a dengue endemic area may be defined as an area wherein the dengue seroprevalence rate in the population targeted for vaccination is at least 50%, at least 60%, at least 70%, at least 80% or at least 90%. In a preferred embodiment, a subject according to the present invention is resident in an area where the dengue seroprevalence in local population aged nine years old is at least 50%, more preferably at least 70%. In this regard, it is considered that older sub-populations exhibit greater seroprevalence rates, since as age increases, the likelihood of having been infected with a dengue virus increases.

When the vaccine composition to be used in a method according to the present invention comprises dengue antigens of serotypes 1 to 4 which comprise nucleic acid sequences having at least 90%, at least 95%, at least 98% or 100% identity to SEQ ID NOs: 1, 2, 3 and 4 respectively (for example the dengue antigens CYD1, CYD2, CYD3 and CYD4), a human subject according to the present invention (to which a vaccine composition of the present invention is administered) is advantageously resident in a dengue endemic area in which the dominant circulating strains of dengue are of serotypes 1, 3 and 4. For example, at least 50%, at least 60%, at least 70%, at least 80% or at least 90% of the cases of dengue disease in said dengue endemic area are caused by a dengue virus of serotypes 1, 3 or 4. A human subject according to the present invention (to which a vaccine composition of the present invention is administered) is advantageously resident in a dengue endemic area in which the dominant circulating strains of dengue are of serotypes 3 and 4. For example, at least 50%, at least 60%, at least 70%, at least 80% or at least 90% of the cases of dengue disease in said dengue endemic area are infections by a dengue virus of serotype 3 or 4.

When the vaccine composition to be used in a method according to the present invention comprises dengue antigens of serotypes 1 to 4 which comprise nucleic acid sequences having at least 90%, at least 95%, at least 98% or 100% identity to SEQ ID NOs: 1, 2, 3 and 4 respectively (for example the dengue antigens CYD1, CYD2, CYD3 and CYD4), a human subject according to the present invention (to which a vaccine composition of the present invention is administered) is advantageously resident in a dengue endemic area in which the circulating dengue strain of serotype 2 has a genotype which is characterised by the presence of Thr and Gly at positions E-226 and E-228. Advantageously, the circulating dengue strain of serotype 2 has a genotype which is characterised by the presence of at least five of or all six of the following residues Arg, Asn, Asp, Thr, Gly and His at positions prM-16, E-83, E-203, E-226, E-228 and E-346 respectively, wherein the residues at positions E-226 and E-228 must be Thr and Gly respectively. In this context, prM-16 designates position 16 of the prM protein and E-83 designates position 83 of the E protein etc. A human subject according to the present invention (to which a vaccine composition of the present invention is administered) is preferably resident in a dengue endemic area in which the circulating serotype 2 dengue virus has a genotype as defined in this paragraph, i.e. at least 50%, at least 60%, at least 70%, at least 80%, at least 90%, at least 95% or 100% of the cases of dengue disease of serotype 2 in said dengue endemic area are caused by dengue virus of serotype 2 having said genotype. Dengue disease caused by a dengue virus of serotype 2, as referred to herein, is preferably dengue disease caused by a dengue virus of serotype 2 having a genotype as defined in this paragraph.

When the vaccine composition to be used in a method according to the present invention comprises dengue antigens of serotypes 1 to 4 which comprise nucleic acid sequences having at least 90%, at least 95%, at least 98% or 100% identity to SEQ ID NOs: 1, 2, 3 and 4 respectively (for example the dengue antigens CYD1, CYD2, CYD3 and CYD4) a human subject according to the present invention (to which a vaccine composition of the present invention is administered) is advantageously resident in a dengue endemic area in which the circulating dengue strain of serotype 2 does not have an Asian-1 genotype. Dengue viruses of serotype 2 can be sub-divided into several genotypes, which are referred to as: American, Asian/American, Asian-1, Asian-2, Cosmopolitan and Sylvatic (Twiddy S S et al. (2002) Phylogenetic relationships and differential selection pressures among genotypes of dengue-2 virus. Virology; 298(1): 63-72). Thus, a human subject according to the present invention (to which a vaccine composition of the present invention is administered) is advantageously resident in a dengue endemic area in which the circulating dengue strain of serotype 2 has an American, Asian/American, Asian-2, Cosmopolitan or Sylvatic genotype. More preferably, a human subject according to the present invention (to which a vaccine composition of the present invention is administered) is advantageously resident in a dengue endemic area in which the circulating dengue strain of serotype 2 has an American, Asian/American, or Cosmopolitan genotype. A human subject according to the present invention (to which a vaccine composition of the present invention is administered) is preferably resident in a dengue endemic area in which the circulating serotype 2 dengue virus has a genotype as defined in this paragraph, i.e. at least 50%, at least 60%, at least 70%, at least 80%, at least 90%, at least 95% or 100% of the cases of dengue disease of serotype 2 in said dengue endemic area are caused by dengue virus of serotype 2 having an American, Asian/American, Asian-2, Cosmopolitan or Sylvatic genotype, preferably an American, Asian/American or Cosmopolitan genotype. Dengue disease caused by a dengue virus of serotype 2, as referred to herein, is preferably dengue disease caused by a dengue virus of serotype 2 having an American, Asian/American, Asian-2, Cosmopolitan or Sylvatic genotype. More preferably, dengue disease caused by a dengue virus of serotype 2, as referred to herein, is preferably dengue disease caused by a dengue virus of serotype 2 having an American, Asian/American, or Cosmopolitan genotype. The genotype of a particular dengue-2 virus strain is determined by sequence alignment and phylogenetic tree analysis. Briefly, reference sequences (which are selected nucleotide sequences encoding the E proteins of a representative strain of each genotype as described in Twiddy et al.) are aligned with the nucleotide sequences encoding the E proteins of the serotype-2 strains to be genotyped. Then a phylogenetic tree is calculated and a genotype is assigned to each unknown serotype-2 strain according to their respective clustering with the reference-genotype sequences. Phylogenetic trees are calculated according to the maximum likelihood method using FastTree 2 software (Price M N et al., FastTree 2-approximately maximum-likelihood trees for large alignments, PLoS One. 2010; 5(3): e9490) and the Whelan and Goldman model of amino acid evolution (Whelan S, Goldman N. A general empirical model of protein evolution derived from multiple protein families using a maximum-likelihood approach. Mol. Biol. Evol. 2001; 18(5): 691-699).

When the vaccine composition to be used in a method according to the present invention comprises dengue antigens of serotypes 1 to 4 which comprise nucleic acid sequences having at least 90%, at least 95%, at least 98% or 100% identity to SEQ ID NOs: 1, 2, 3 and 4 respectively (for example the dengue antigens CYD1, CYD2, CYD3 and CYD4), a human subject according to the present invention (to which a vaccine composition of the present invention is administered) is advantageously resident in a dengue endemic area in which the circulating dengue strain of serotype 4 is of the DEN4-II genotype. In particular, a circulating dengue strain of serotype 4 preferably has residues at "signature" positions pr73, M65, E46, E120, E160, E203, E329, E429, E455, E461 and E478 which match with the equivalent residues in the prM, M and E protein sequences of CYD4 as may be easily derived from SEQ ID NO: 4. Preferably, at least 4, at least 5, at least 6, at least 7, at least 8, at least 9 or all 10 of the "signature" residues must match. M65 refers to position 65 of the M protein and pr73 refers to position 73 of the prM protein etc. A human subject according to the present invention (to which a vaccine composition of the present invention is administered) is preferably resident in a dengue endemic area in which the circulating serotype 4 dengue virus has a DEN4-II genotype as defined in this paragraph, i.e. at least 50%, at least 60%, at least 70%, at least 80%, at least 90%, at least 95% or 100% of the cases of dengue disease of serotype 4 in said dengue endemic area are caused by dengue virus of serotype 4 having said genotype. Dengue disease caused by a dengue virus of serotype 4, as referred to herein, is preferably dengue disease caused by a dengue virus of serotype 4 having a genotype as defined in this paragraph.

When the vaccine composition to be used in a method according to the present invention comprises dengue antigens of serotypes 1 to 4 which comprise nucleic acid sequences having at least 90%, at least 95%, at least 98% or 100% identity to SEQ ID NOs: 1, 2, 3 and 4 respectively (for example the dengue antigens CYD1, CYD2, CYD3 and CYD4), a human subject according to the present invention (to which a vaccine composition of the present invention is administered) is advantageously resident in a dengue endemic area in which the circulating dengue strains of serotypes 1, 2, 3 and 4 comprise prM-E nucleotide sequences which have at least 90%, at least 95%, at least 98% or 100% identity to SEQ ID NOs: 1, 2, 3 and 4 respectively.

Preferably, a booster vaccination according to the present invention, i.e. a composition for use in a method according to the first or the second aspect of the present invention, reduces the incidence or likelihood of dengue disease.

Preferably, a booster vaccination according to the present invention, i.e. a composition for use in a method according to the first or the second aspect of the present invention, results in the prevention of (i.e. is for use in the prevention of) dengue disease caused by dengue virus serotypes 1, 2, 3 and 4 in individuals 9 through 60 years of age, or 9 through 45 years of age, living in endemic areas. In this context, an individual is understood to be a human subject.

Preferably, a booster vaccination according to the present invention, i.e. a composition for use in a method according to the first or the second aspect of the present invention, results in the prevention of (i.e. is for use in the prevention of) dengue disease caused by dengue virus serotypes 1, 2, 3 and 4 in individuals 12 through 60 years of age, or 12 through 45 years of age, living in endemic areas. In this context, an individual is understood to be a human subject.

The exact quantity of a live attenuated dengue virus or a live attenuated chimeric dengue virus of the present invention to be administered in a primary vaccination or in a booster vaccination may vary according to the age and the weight of the subject being vaccinated, the frequency of administration as well as the other ingredients in the composition. Generally, the quantity of a live attenuated dengue virus (e.g. VDV1 or VDV2) comprised in a dose of a vaccine composition of the present invention, for primary or booster vaccination, lies within a range of from about $10^3$ to about $10^6$ $CCID_{50}$, for example within a range of from about $5\times10^3$ to about $5\times10^5$, for example about $10^4$ $CCID_{50}$. The quantity of a chimeric dengue virus (such as a chimeric YF/dengue virus or a Chimerivax® (CYD) virus) comprised in a vaccine composition of the present invention, for primary or booster vaccination, lies within a range of about $10^5$ $CCID_{50}$ to about $10^6$ $CCID_{50}$. The quantity of a live attenuated dengue virus or live attenuated chimeric dengue virus of each of serotypes 1 to 4 comprised in a tetravalent dosage form or bivalent dosage forms according to the present invention is preferably equal. Advantageously, a vaccine composition for use according to the present invention in a primary or booster vaccination comprises an effective amount of a dengue antigen as defined herein.

A vaccine composition for use in a booster vaccination according to the $1^{st}$ aspect of the present invention, or for use in a primary vaccination followed by a booster vaccination according to the $2^{nd}$ aspect, may further comprise a pharmaceutically acceptable carrier or excipient. A pharmaceutically acceptable carrier or excipient according to the present invention means any solvent or dispersing medium etc., commonly used in the formulation of pharmaceuticals and vaccines to enhance stability, sterility and deliverability of the active agent and which does not produce any secondary reaction, for example an allergic reaction, in humans. The excipient is selected on the basis of the pharmaceutical form chosen, the method and the route of administration. Appropriate excipients, and requirements in relation to pharmaceutical formulation, are described in "Remington's Pharmaceutical Sciences" (19th Edition, A. R. Gennaro, Ed., Mack Publishing Co., Easton, Pa. (1995)). Particular examples of pharmaceutically acceptable excipients include water, phosphate-buffered saline (PBS) solutions and a 0.3% glycine solution. A vaccine composition according to the present invention may advantageously comprise 0.4% saline.

A vaccine composition for use as a booster in a method of the present invention may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccine composition may optionally comprise pharmaceutically acceptable additives including, for example, diluents, binders, stabilizers, and preservatives. Preferred stabilizers are described in WO 2010/003670.

As appreciated by skilled artisans, a vaccine composition for use as a booster according to the first or $2^{nd}$ aspect of the present invention, is suitably formulated to be compatible with the intended route of administration. Examples of suitable routes of administration include for instance intramuscular, transcutaneous, subcutaneous, intranasal, oral or intradermal. Advantageously, the route of administration is subcutaneous.

The vaccine compositions for use according to the first or $2^{nd}$ aspect of the present invention may be administered using conventional hypodermic syringes or safety syringes such as those commercially available from Becton Dickinson Corporation (Franklin Lakes, N.J., USA) or jet injectors. For intradermal administration, conventional hypodermic syringes may be employed using the Mantoux technique or specialized intradermal delivery devices such as the BD Soluvia™ microinjection system (Becton Dickinson Corporation, Franklin Lakes, N.J., USA), may be used.

The volume of a vaccine composition administered will depend on the method of administration. In the case of subcutaneous injections, the volume is generally between 0.1 and 1.0 ml, preferably approximately 0.5 ml.

According to one embodiment, the invention also provides a kit comprising a vaccine composition of the invention and instructions for the use of said vaccine composition as a booster vaccination according to the first aspect of the invention, or as a primary vaccination and a booster vaccination according to the $2^{nd}$ aspect, in a method of protecting a human subject against dengue disease. The kit may comprise said vaccine composition in the form of a single tetravalent dosage form or said kit may comprise said vaccine composition in the form of two bivalent dosage forms. The kit can comprise at least one dose (typically in a syringe) of any vaccine composition contemplated herein. According to one embodiment the kit may comprises a multi-dose formulation of any vaccine composition as described herein. The kit further comprises a leaflet mentioning the use of the said vaccine composition for the prevention of dengue disease or the use of the said vaccine for the prophylaxis of dengue disease, as a booster vaccination or as a primary vaccination and a booster vaccination. The leaflet may further mention the vaccination regimen and the human subject population to be vaccinated, namely subjects who have not previously been naturally infected by a dengue virus, irrespective of the serotype.

The efficacy of a booster composition of the present invention in reducing the likelihood or severity of dengue disease may be measured in a number of ways. For instance, the efficacy of a booster composition of the present invention in reducing the likelihood or severity of dengue disease may be calculated by measuring after the administration of at least one dose of said booster composition (e.g. after administration of one, two or three doses of said booster composition):

(i) the number of cases of dengue disease caused by dengue virus of any serotype;
(ii) the number of severe dengue cases caused by dengue virus of any serotype;
(iii) the number of DHF cases caused by dengue virus of any serotype; and/or
(iv) the number of hospitalized cases of dengue disease caused by dengue virus of any serotype;

in a group of subjects that has received said booster composition, and comparing those measurements with the equivalent measurements from a control group of subjects that has not received said booster composition, wherein the subjects in both said groups are resident in a dengue endemic region, have received a primary vaccination and have not been naturally infected by a dengue virus. A statistically conclusive reduction in any one or more of (i) to (iv) in the group of subjects receiving the booster when compared with the control group of subjects not receiving the booster, is indicative of the efficacy of a booster composition according to the present invention.

The efficacy of a booster composition according to the present invention in reducing the severity or likelihood of dengue disease may also be calculated by measuring after the administration of at least one dose of said booster composition (e.g. after administration of one, two or three doses of said booster composition):

(i) the mean duration and/or intensity of fever;
(iii) the mean value for plasma leakage as defined by a change in haematocrit;
(iii) the mean value for thrombocytopenia (platelet count); and/or
(iv) the mean value of the level of liver enzymes including alanine aminotransferase (ALT) and aspartate aminotransferase (AST);

in a group of subjects that has received said booster composition and who have developed virologically-confirmed dengue disease after the administration of the booster, and comparing those measurements with the equivalent measurements from a control group of subjects that has not received said booster composition and who have developed virologically-confirmed dengue disease, wherein the subjects in both said groups have received a primary vaccination and have not been naturally infected by a dengue virus before the booster. A statistically significant reduction in any one or more of (i) to (iv) in the group of subjects who have received the booster dose and have developed virologically-confirmed dengue disease when compared with the control group of subjects who have not received the booster and have developed virologically-confirmed dengue disease is indicative of the efficacy of a booster composition according to the present invention in reducing the severity or likelihood of dengue disease.

The efficacy of a booster composition according to the present invention in reducing the severity or likelihood of dengue disease may also be calculated by measuring after the administration of at least one dose of said booster composition (e.g. administration of one, two or three doses of said booster composition) the neutralising antibody titre induced by said booster composition in a group of subjects that has received said booster composition and using a correlate of risk or a correlate of protection (if available) to convert the neutralizing antibody titre into a measure of efficacy.

Alignments of the nucleic sequences disclosed herein with other nucleic acid sequences may be achieved by any of the suitable sequence alignment methods well known to a person skilled in the art. For example, sequence alignments may be carried out by hand. More conveniently, an alignment may be carried out using a specialised computer program. For example, optimal sequence alignment can be achieved and percent identity can be determined by global sequence alignment algorithms such as the Multiple Sequence Alignment (MSA) algorithms Clustal W and Clustal Omega algorithms, or the Multiple Sequence Comparison by Log-Expectation (MUSCLE) algorithm (Edgar R C, Nucl. Acids Res. (2004): 32 (5): 1792). These algorithms are available on the European Bioinformatics Institute (EBI) web site at http://www.ebi.ac.uk/services. Where such algorithms have user-defined parameters, the default parameters should be used.

It is understood that the various features and preferred embodiments of the present invention as disclosed herein may be combined together.

Throughout this application, various references are cited. The disclosures of these references are hereby incorporated by reference into the present disclosure.

The present invention will be further illustrated by the following examples. It should be understood however that the invention is defined by the claims, and that these examples are given only by way of illustration of the invention and do not constitute in any way a limitation thereof.

EXPERIMENTAL SECTION

CYD64 Clinical Trial: Immunogenicity and Safety of a Tetravalent Dengue Vaccine Given as a Booster Injection in Adolescents and Adults Who Previously Completed the 3-Dose Schedule in a Study Conducted in Latin America.

1) Summary

The aim of the study is to assess and describe the booster effect of a CYD dengue vaccine dose administered 4 to 5 years after the completion of a 3-dose vaccination schedule.

Primary Objective

To demonstrate the non-inferiority, in terms of geometric mean of titer ratios (GMTRs), of a CYD dengue vaccine booster compared to the third CYD dengue vaccine injection in subjects from previous CYD dengue vaccine trials.

Secondary Objectives:

If the primary objective of non-inferiority is achieved: To demonstrate the superiority, in terms of GMTRs, of a CYD dengue vaccine booster compared to the third CYD dengue vaccine injection in subjects from previous CYD dengue vaccine trials.

To describe the immune responses elicited by a CYD dengue vaccine booster and placebo injection in subjects who received 3 doses of the CYD dengue vaccine in previous CYD dengue vaccine trials.

To describe the neutralizing Antibodies (Ab) levels of each dengue serotype post-dose 3 (previous CYD dengue vaccine trials' subjects) and immediately prior to booster or placebo injection in all subjects.

To describe the neutralizing Ab persistence 6 months and 1 year post booster or placebo injection in all subjects.

To evaluate the safety of booster vaccination with the CYD dengue vaccine in all subjects.

Primary Outcome Measures:

Neutralizing antibody levels against each dengue virus serotype measured 28 days after the third CYD dengue vaccine injection and 28 days after the booster injection in the study group [Time Frame: Day 28 post booster vaccination].

Secondary Outcome Measures:

Neutralizing antibody levels against each of the 4 parental dengue virus strains of the CYD dengue vaccine immediately prior and 28 days post booster or placebo injection [Time Frame: Before and Day 28 post booster vaccination]

Neutralizing antibody levels against each of the 4 parental dengue virus strains of the CYD dengue vaccine 6 months and 1 year post booster or placebo injection [Time Frame: 6 months and 12 months post booster vaccination]

Percentages of subjects with seroconversion 28 days after the booster injection for each of the four parental dengue virus strain of CYD dengue vaccine: percentages of subjects with either a pre-booster titer <10 (1/dil) and a post-booster titer 40 (1/dil), or a pre-booster titer 10 (1/dil) and a 4-fold increase in post-booster titer as determined by PRNT immediately prior and 28 days post-booster or placebo injection [Time Frame: Before and Day 28 post booster vaccination]

Number of participants reporting solicited injection site reactions, solicited systemic reactions, unsolicited adverse events, and serious adverse events occurring during trial [Time Frame: Day 0 up to 2 years post vaccination]

Solicited injection site reactions: Pain, Erythema, and Swelling. Solicited systemic reactions: Fever (temperature), Headache, Malaise, Myalgia, and Asthenia Neutralizing antibody levels against each dengue virus serotype are measured using dengue plaque reduction neutralization test (PRNT).

2) Statistical Methods

Hypothesis and Statistical Method for the Primary Objective (Group 1 only) Hypotheses:

Individual Hypotheses for Each Serotype:

A non-inferiority testing approach was performed for each serotype to demonstrate the non-inferiority, in terms of GMTRs, 28 days post-injection, of a CYD dengue vaccine booster dose compared to the third CYD dengue vaccine dose in subjects from CYD13 (Villar L A, et al, 2013, Pediatr Infect Dis J; 32(10):1102-1109) and CYD30 (Dayan G H, et al, 2013, Am J Trop Med Hyg 2013; 89(6): 1058-1065) trials.

Individual hypotheses for each serotype were as follows:

$H_0^i: GM(V_{Booster}^i / V_{PD3}^i) \le \frac{1}{2}$
$H_1^i: GM(V_{Booster}^i / V_{PD3}^i) > \frac{1}{2}$ Where i=1, 2, 3 and 4; $V_{Booster}^i$ is the immunogenicity titer 28 days after the CYD dengue vaccine booster dose and $V_{PD3}^i$ is the immunogenicity titer 28 days after the third CYD dengue vaccine dose in CYD13 and CYD30 subjects.

Overall Hypothesis:

The overall null hypothesis can be stated as for at least 1 serotype, the post booster dose response (28 days after the CYD dengue vaccine booster injection) is inferior to the PD3 response (28 days after the third CYD dengue vaccine dose in CYD13 and CYD30 subjects)

$H_0^G$ at least one $H_0^i$ not rejected
$H_1^G$: all $H_0^i$ are rejected

Statistical Methods

A non-inferiority test was performed using the 95% two-sided CI of GM($V_{Booster}/V_{PD3}$) for each serotype; the 95% CI was calculated using paired t-test.

Subjects with non-missing PD3 and post booster dose titer were included in this analysis. For each serotype, non-inferiority was demonstrated if the lower limit of the two-sided 95% CI was greater than ½. If the null hypothesis is rejected, then the alternative hypothesis of non-inferiority is supported.

The overall null hypothesis was rejected if the four individual null hypotheses were rejected simultaneously.

Hypotheses and Statistical Methods for the First Secondary Objective

As non-inferiority was demonstrated for the primary endpoint, then superiority hypotheses will be performed.

Hypotheses:

Individual Hypotheses for Each Serotype:

A superiority hypothesis testing approach was performed for each serotype to demonstrate the superiority, in terms of GMTRs, 28 days post-injection, of a CYD dengue vaccine booster dose compared to the third CYD dengue vaccine dose in subjects from CYD13 and CYD30 trials. Individual hypotheses for each serotype will be as follows:

$H_0^i$: GM($V_{Booster}^i/V_{PD3}^i$) ≤ 1

$H_1^i$: GM($V_{Booster}^i/V_{PD3}^i$) > 1

Where i=1, 2, 3 and 4; $V_{Booster}^i$ is the immunogenicity titer 28 days after the CYD dengue vaccine booster dose and is $V_{PD3}^i$ the immunogenicity titer 28 days after the third CYD dengue vaccine dose in CYD13 and CYD30 subjects.

Overall Hypothesis:

The overall null hypothesis can be stated as for at least 1 serotype, the post booster dose response (28 days after the CYD dengue vaccine booster injection) is not superior to the PD3 response (28 days after the third CYD dengue vaccine dose in CYD13 and CYD30 subjects).

$H_0^G$ at least one $H_0^i$ not rejected $H_1^G$: all $H_0^i$ are rejected

Statistical Methods

A superiority test was performed using the 95% two-sided CI of GM($V_{Booster}/V_{PD3}$) for each serotype; the 95% CI was calculated using paired t-test.

Subjects with non-missing PD3 and post booster dose titer were included in this analysis. For each serotype, superiority was to be demonstrated if the lower limit of the two-sided 95% CI is greater than 1. If the null hypothesis was rejected, then the alternative hypothesis of superiority was supported.

The overall null hypothesis was to be rejected if the four individual null hypotheses were rejected simultaneously.

Statistical Methods for Other Secondary and Additional Objectives

All other analyses are descriptive; no hypotheses are tested.

For immunogenicity, 2 sample t-test on the $\log_{10}$ transformed titers were used for 95% CI for the ratio of geometric mean titers (GMTs) (difference between GMTs on log scale).

The 95% CIs for percentages were calculated using the exact binomial distribution (Clopper-Pearson's method). Assuming that logo transformation of the titers/titers ratio followed a normal distribution, first, the mean and 95% CIs were calculated on logo (titers/titers ratio) using the usual calculation for normal distribution, then antilog transformations were applied to the results of calculations, to compute GMTs/GMTRs and their 95% CIs.

For safety, the exact binomial distribution (Clopper-Pearson method) for proportions was used in calculations of the 95% CIs.

Calculation of Sample Size:

There was to be 279 subjects in Group 1 and 93 subjects in Group 2. Assuming a dropoutrate of approximately 2% for each group 28 days post injection, a total of 273 and 91 evaluable subjects was anticipated for Groups 1 and 2, respectively. With 273 evaluable subjects, the probability of observing at least 1 AE with true incidence of 1.1% was approximately 95%. Sample size for the primary endpoint (only for Group 1) was estimated to demonstrate non-inferiority, in terms of GMTRs, 28 days post-injection, of a CYD dengue vaccine booster compared to the third CYD dengue vaccine dose in subjects from CYD13 and CYD30 trials. With 273 evaluable subjects in Group 1, the overall power (see Table 1) using paired test to reject the 4 individual null hypotheses simultaneously was expected to be 88.3%; calculation assumed a non-inferiority margin (delta) =2, one-sided type I error=0.025 and correlation between the responses PD3 and post booster dose of the same serotype in the same subject=0.5.

TABLE 1

Power/Sample size calculation summary table for primary endpoint

| Component (Antigen) | Standard deviation (log 10) | Non-Inferiority Definition | Power for N = 273 |
|---|---|---|---|
| Serotype 1 | (sd1 = 0.88, sd2 = 1.76) | >1/2 | 0.902 |
| Serotype 2 | (sd1 = 0.70, sd2 = 1.40) | >1/2 | 0.983 |
| Serotype 3 | (sd1 = 0.62, sd2 = 1.24) | >1/2 | 0.996 |
| Serotype 4 | (sd1 = 0.50, sd2 = 1.00) | >1/2 | 1.000 |
| Overall | | | 0.883 |

The calculation of the standard deviation for PD3 (sd1) was based on the weighted average of 28-day PD3 standard deviations of titers from the Phase II trials CYD13 and CYD30 and the standard deviation for post booster dose (sd2) was estimated based on standard deviation for PD3.

Since 4 individual null hypotheses should be rejected simultaneously to reject the overall null hypothesis, no multiplicity adjustment for alpha is necessary.

A 3:1 randomization ratio between Group 1 and Group 2 was chosen, so 279 and 93 subjects were expected to be enrolled in Group 1 and Group 2, respectively.

Calculation of Geometric Mean of Titer (GMT) and Geometric Mean of Titer Ratios (GMTR):

The geometric mean of the neutralizing antibody titer was calculated assuming that Log10 transformation of the titers follows a normal distribution, such that the mean and the 95% CI were calculated on Log10 (titers) using the usual calculation for normal distribution (using Student's t distribution with n-1 degree of freedom). The antilog transformation is then applied to the results of calculations, in order to provide geometric mean of titers (GMTs). For the computation of GMTs, a titer reported as below LLOQ is converted to a value of 0.5 LLOQ.

The GM is defined as follows:

$$GM = \left(\prod_{i=1}^{n} y_i\right)^{1/n} = 10^{\frac{1}{n}\sum_{i=1}^{n} \log_{10}(y_i)}$$

With respect to Geometric Mean Ratios, they were obtained by first calculating the difference of the log transformed data between two comparable groups, and then the ratios are obtained by anti-log transformation of the difference.

For calculating the geometric mean titer ratio (GMTR), the values below LLOQ are converted to 0.5 LLOQ for a numerator, and the values below LLOQ are converted to LLOQ for a denominator.

This method provides the most conservative results for GMTR.

3) Method for Assessing the Dengue Neutralizing Antibody Level and Seroconversion:

Dengue neutralizing Ab levels are measured by PRNT (using parental dengue virus strains of CYD dengue vaccine constructs) by Sanofi Pasteur GCI, Swiftwater, USA (or outsourced with a GCI selected external laboratory).

Serial, 2-fold dilutions of serum to be tested (previously heat-inactivated) are mixed with a constant challenge-dose of each dengue virus serotype 1, 2, 3 or 4 (expressed as plaque-forming unit [PFU/mL]. The mixtures are inoculated into wells of a microplate with confluent

TABLE 7A

NAb titres against each serotype at PD3, pre-booster injection and 28 days post-booster injection in subjects dengue naïve (non-immune) at baseline (i.e. at D0 in the previous trials CYD13 and CYD30)

| Component | Time point/ratio | CYD Dengue Vaccine Group (N = 177) | | | Placebo Group (N = 64) | | |
|---|---|---|---|---|---|---|---|
| | | M | GM | (95% CI) | M | GM | (95% CI) |
| Serotype 1 [PRNT-1/dil] | Post dose 3 in CYD13 and CYD30 (PD3) | 40 | 26.2 | (17.0; 40.4) | 18 | 39.9 | (19.3; 82.4) |
| | V01 (D0) | 41 | 29.6 | (15.6; 56.1) | 18 | 54.0 | (21.4; 136) |
| | V04 (D28) | 41 | 100 | (52.5; 192) | 18 | 40.4 | (12.6; 130) |
| | Ratio V01 (D0)/PD3 | 40 | 0.801 | (0.431; 1.49) | 18 | 1.16 | (0.524; 2.57) |
| | Ratio V04 (D28)/PD3 | 40 | 2.86 | (1.48; 5.51) | 18 | 0.866 | (0.318; 2.36) |
| | Ratio V04 (D28)/V01 (D0) | 41 | 2.54 | (1.57; 4.11) | 18 | 0.616 | (0.356; 1.07) |
| Serotype 2 [PRNT-1/dil] | Post dose 3 in CYD13 and CYD30 (PD3) | 40 | 57.1 | (39.6; 82.3) | 18 | 79.9 | (39.3; 163) |
| | V01 (D0) | 41 | 48.9 | (25.4; 94.1) | 18 | 55.0 | (20.2; 150) |
| | V04 (D28) | 41 | 213 | (121; 375) | 18 | 61.0 | (17.5; 213) |
| | Ratio V01 (D0)/PD3 | 40 | 0.757 | (0.416; 1.38) | 18 | 0.637 | (0.201; 2.03) |
| | Ratio V04 (D28)/PD3 | 40 | 3.45 | (1.93; 6.18) | 18 | 0.706 | (0.181; 2.75) |
| | Ratio V04 (D28)/V01 (D0) | 41 | 3.38 | (2.23; 5.12) | 18 | 0.880 | (0.415; 1.86) |
| Serotype 3 [PRNT-1/dil] | Post dose 3 in CYD13 and CYD30 (PD3) | 41 | 129 | (98.1; 168) | 18 | 138 | (82.0; 234) |
| | V01 (D0) | 41 | 51.8 | (27.4; 97.9) | 18 | 68.3 | (28.7; 163) |
| | V04 (D28) | 41 | 288 | (163; 510) | 18 | 74.8 | (27.8; 201) |
| | Ratio V01 (D0)/PD3 | 41 | 0.403 | (0.227; 0.714) | 18 | 0.493 | (0.256; 0.950) |
| | Ratio V04 (D28)/PD3 | 41 | 2.24 | (1.30; 3.88) | 18 | 0.540 | (0.240; 1.22) |
| | Ratio V04 (D28)/V01 (D0) | 41 | 4.55 | (2.86; 7.22) | 18 | 0.976 | (0.556; 1.71) |
| Serotype 4 [PRNT-1/dil] | Post dose 3 in CYD13 and CYD30 (PD3) | 41 | 103 | (65.9; 162) | 18 | 119 | (71.9; 197) |
| | V01 (D0) | 41 | 54.9 | (37.2; 80.9) | 18 | 31.2 | (16.1; 60.3) |
| | V04 (D28) | 41 | 347 | (183; 657) | 18 | 37.0 | (17.9; 76.6) |
| | Ratio V01 (D0)/PD3 | 41 | 0.487 | (0.278; 0.854) | 18 | 0.252 | (0.133; 0.476) |
| | Ratio V04 (D28)/PD3 | 41 | 3.08 | (1.50; 6.36) | 18 | 0.299 | (0.148; 0.604) |
| | Ratio V04 (D28)/V01 (D0) | 41 | 5.91 | (2.99; 11.7) | 18 | 0.980 | (0.632; 1.52) |

TABLE 7B

NAb titres against each serotype at PD3, pre-booster injection and 28 days post-booster injection in subjects dengue immune at baseline (i.e. at D0 in the previous trials CYD13 and CYD30)

| Component | Time point/ratio | CYD Dengue Vaccine Group (N = 177) | | | Placebo Group (N = 64) | | |
|---|---|---|---|---|---|---|---|
| | | M | GM | (95% CI) | M | GM | (95% CI) |
| Serotype 1 [PRNT-1/dil] | Post dose 3 in CYD13 and CYD30 (PD3) | 136 | 656 | (501; 861) | 46 | 463 | (278; 771) |
| | V01 (D0) | 136 | 668 | (498; 895) | 46 | 725 | (413; 1273) |
| | V04 (D28) | 136 | 940 | (723; 1222) | 46 | 650 | (358; 1181) |
| | Ratio V01 (D0)/PD3 | 136 | 1.00 | (0.803; 1.25) | 46 | 1.52 | (0.913; 2.53) |
| | Ratio V04 (D28)/PD3 | 136 | 1.41 | (1.15; 1.73) | 46 | 1.36 | (0.840; 2.21) |
| | Ratio V04 (D28)/V01 (D0) | 136 | 1.38 | (1.16; 1.65) | 46 | 0.882 | (0.668; 1.17) |
| Serotype 2 [PRNT-1/dil] | Post dose 3 in CYD13 and CYD30 (PD3) | 135 | 613 | (474; 792) | 46 | 511 | (365; 713) |
| | V01 (D0) | 136 | 657 | (505; 853) | 46 | 647 | (408; 1025) |
| | V04 (D28) | 136 | 922 | (734; 1158) | 46 | 705 | (439; 1132) |
| | Ratio V01 (D0)/PD3 | 135 | 1.07 | (0.827; 1.38) | 46 | 1.27 | (0.794; 2.02) |
| | Ratio V04 (D28)/PD3 | 135 | 1.50 | (1.17; 1.94) | 46 | 1.38 | (0.871; 2.19) |
| | Ratio V04 (D28)/V01 (D0) | 136 | 1.38 | (1.16; 1.65) | 46 | 1.09 | (0.782; 1.52) |
| Serotype 3 [PRNT-1/dil] | Post dose 3 in CYD13 and CYD30 (PD3) | 134 | 1045 | (849; 1286) | 46 | 921 | (627; 1353) |
| | V01 (D0) | 136 | 638 | (502; 811) | 46 | 918 | (581; 1452) |
| | V04 (D28) | 136 | 866 | (689; 1089) | 46 | 857 | (561; 1311) |
| | Ratio V01 (D0)/PD3 | 134 | 0.585 | (0.483; 0.710) | 46 | 0.997 | (0.655; 1.52) |
| | Ratio V04 (D28)/PD3 | 134 | 0.817 | (0.668; 0.999) | 46 | 0.931 | (0.617; 1.40) |
| | Ratio V04 (D28)/V01 (D0) | 136 | 1.34 | (1.12; 1.61) | 46 | 0.934 | (0.724; 1.20) |

TABLE 7B-continued

NAb titres against each serotype at PD3, pre-booster injection and 28 days post-booster injection in subjects dengue immune at baseline (i.e. at D0 in the previous trials CYD13 and CYD30)

| Component | Time point/ratio | CYD Dengue Vaccine Group (N = 177) | | | Placebo Group (N = 64) | | |
|---|---|---|---|---|---|---|---|
| | | M | GM | (95% CI) | M | GM | (95% CI) |
| Serotype 4 [PRNT-1/dil] | Post dose 3 in CYD13 and CYD30 (PD3) | 135 | 315 | (249; 400) | 45 | 346 | (253; 475) |
| | V01 (D0) | 136 | 224 | (186; 269) | 46 | 307 | (214; 441) |
| | V04 (D28) | 136 | 343 | (281; 418) | 46 | 287 | (205; 402) |
| | Ratio V01 (D0)/PD3 | 135 | 0.664 | (0.527; 0.838) | 45 | 0.876 | (0.584; 1.31) |
| | Ratio V04 (D28)/PD3 | 135 | 1.03 | (0.786; 1.34) | 45 | 0.825 | (0.551; 1.24) |
| | Ratio V04 (D28)/V01 (D0) | 136 | 1.52 | (1.25; 1.86) | 46 | 0.933 | (0.744; 1.17) |

Vero cell monolayers. After adsorption, cell monolayers are incubated for a few days. The presence of dengue virus infected cells is indicated by formation of plaques. A reduction in virus infectivity due to neutralization by Ab present in serum samples is detected. The reported value (end point neutralization titer) represents the highest dilution of serum at which ≥50% of dengue challenge virus (in plaque counts) is neutralized when compared to the mean viral plaque count in the negative control wells which represents the 100% virus load. The end point neutralization titers are presented as discontinuous values. The lower limit of quantitation (LLOQ) of the assay is 10 (1/dil).

Seroconversion rates 28 days after the booster injection for each of the four parental dengue virus strain of CYD-TDV dengue vaccine, was defined as the percentages of subjects with either a pre-booster titer <10 (1/dil) and a post-booster titer ≥40 (1/dil), or a pre-booster titer ≥10 (1/dil) and a ≥4-fold increase in post-booster titer as determined by $PRNT_{50}$ (Plaque Reduction Neutralization Test) immediately prior and 28 days post-booster or placebo injection. The safety profile of the booster dose was also analyzed with no specific findings.

4) Introduction:

CYD64 is a multi-center, observer-blind, randomized, placebo controlled, Phase II non-inferiority trial conducted in 251 healthy adolescents and adults in Brazil, Colombia, Honduras, Mexico and Puerto Rico, who received one CYD-TDV dengue vaccine (Dengvaxia®) booster dose between Apr. 14, 2016 and Oct. 19, 2016. It was conducted in accordance with the Declaration of Helsinki and the International Conference on Harmonisation guidelines for good clinical practice as well as with all local and/or national regulations. In addition, each study site's Institutional Review Board and Independent Ethics Committee approved the study protocol. No protocol amendments have been done to date. Written informed consent was obtained from all participants and/or participants' parents/guardians before study entry. Eligible participants were healthy adolescents and adults aged 15.3-23.8 years that had received 3 doses of the CYD-TDV dengue vaccine 4-5 years earlier in two previous specific trials (CYD30 and CYD13, NCT01187433 and NCT00993447 respectively). Exclusion criteria included previous vaccination against dengue that was not part of the previous mentioned trials; pregnant, lactating or childbearing potential women; participation at any time of study enrollment in another trial; reception of any vaccine in the 4 weeks preceding the trial vaccination or planned to receipt any vaccine in the 4 week following the trial vaccination; reception of immune globulins, blood or blood-derived products in the past 3 months; known or suspected congenital or acquired immunodeficiency; reception of any immunosuppressive therapy; known systemic hypersensitivity to any of the vaccine components, or history of a life-threatening reaction to the vaccines used in the trial or to a vaccine containing any of the same substances; chronic illness that, in the opinion of the Investigator, could interfere with trial conduct or completion; deprivation of freedom by an administrative or court order, or in an emergency setting, or hospitalized involuntarily; current alcohol abuse or drug addiction; moderate or severe acute illness/infection on the day of vaccination or febrile illness (temperature≥38.0° C.); identified as an Investigator or employee of the Investigator or study center with direct involvement in the proposed study, or any identified immediate family member.

Each of the 251 participants enrolled in the trial were randomly assigned to one of the two study groups (group 1 or group 2) via an interactive voice response system or interactive web response system according to a 3:1 ratio (3 subjects in the CYD-TDV Dengue Vaccine Group for 1 subject included in the Placebo Group). Randomization was performed with permuted block method with stratification by site. A double randomization system was used, this implies that the subject treatment allocation was separated from doses dispensing. The unique dose numbers was defined according to a random list to ensure that dose numbers could not be used to distinguish between treatment groups. Subject numbers were not reassigned for any reason.

All participants in Group 1 received a CYD-TDV Dengue vaccine and all participants in Group 2 received a placebo injection at enrollment (day 0); also all participants provided 1 pre-injection blood sample at enrollment to assess baseline dengue immune status before the first vaccination, and 1 blood sample 28 days post-injection for dengue immunogenicity. Neutralizing antibodies against each of the 4 parental dengue virus strains were measured 28 days after the third CYD-TDV dengue vaccine injection and 28 days post-booster injection (Group 1 only).

For both groups, neutralizing antibodies (Nabs) against each of the 4 parental dengue virus strains were measured immediately prior the booster or placebo injection. Also, individual post-booster/pre-booster Geometric Mean Titers Ratios (GMTRs) for each of the four parental dengue virus strains of the CYD-TDV dengue vaccine were measured immediately prior and 28 days post-booster or placebo injection.

For both groups, Nabs against each of the 4 parental dengue virus strains were measured 6 months and one year post booster or placebo injection.

5) Results of the CYD64 Trial, 28 Days Post-Booster Dose

A total of 251 were randomized out of the 372 planned subjects. Following randomization, 187 subjects were allocated to the CYD-TDV Dengue Vaccine Group and 64 subjects to the Placebo Group. The overall distribution of randomized subjects by country and treatment group is summarized in table 2.

TABLE 2

Subjects randomized per country

| Country | CYD Dengue Vaccine Group (N = 187) n (%) | Placebo Group (N = 64) n (%) | All (N = 251) n (%) |
|---|---|---|---|
| All | 187 (100.0) | 64 (100.0) | 251 (100.0) |
| Brazil | 32 (17.1) | 11 (17.2) | 43 (17.1) |
| Colombia | 57 (30.5) | 19 (29.7) | 76 (30.3) |
| Honduras | 32 (17.1) | 10 (15.6) | 42 (16.7) |
| Mexico | 49 (26.2) | 18 (28.1) | 67 (26.7) |
| Puerto Rico | 17 (9.1) | 6 (9.4) | 23 (9.2) |

Overall, at 28 days post-booster injection, 250 (99.6%) subjects were present (i.e. 1 subject from the CYD-TDV Dengue Vaccine Group was absent) and 249 (99.2%) subjects provided a blood sample (i.e., 2 subjects from the CYD-TDV Dengue Vaccine Group did not provide a sample). At 28 days post-booster injection there was only 1 (0.5%) subject who was discontinued from the study. The reason for discontinuation was non-compliance with the protocol.

Non-Inferiority of CYD-TDV Dengue Vaccine Booster Compared to the 3rd CYD-TDV Dengue Vaccine Dose in Previous Trials.

Non-inferiority of dengue Nab after CYD-TDV dengue vaccine booster dose compared to the $3^{rd}$ CYD-TDV dengue vaccine dose (PD3) in terms of Dengue PRNT was demonstrated for the 4 serotypes (lower limit of 2-sided 95% CI greater than ½). A Post booster/PD3 ratio with a 95% CI was calculated for each serotype. (Table 3) A covariance analysis of post booster titers against each of the 4 serotypes was done for controlling the baseline Nab levels (removing pre booster effect); a Dengue/Placebo GMT ratio with a 95% CI was calculated for each serotype: serotype 1, ratio 2.04 (1.50; 2.78), p value 0.0004; serotype 2, ratio 1.74 (1.28; 2.38), p value 0.0021; serotype 3, ratio 1.85 (1.37; 2.50), p value 0.0002; and serotype 4, ratio 2.19 (1.53; 3.13), p value<0.0001. This shows that the immunological response is better in the vaccinated group compared with placebo. (Table 4).

Superiority of CYD-TDV Dengue Vaccine Booster Compared to the 3rd CYD-TDV Dengue Vaccine Dose in Previous Trials.

As the overall non-inferiority of the CYD-TDV dengue vaccine booster could be demonstrated, a superiority analysis of the booster dose compared to the third dose of the selected previous trials was performed for each serotype using GMTRs. The superiority of the booster dose was demonstrated for serotype 1, serotype 2, and serotype 4. The superiority of the booster dose could not be demonstrated for serotype 3 as the lower limit of the two-sided 95% CI of the GMTR was <1 for this serotype. (Table 5).

Immune Response 28 Days Post-Booster Injection

At pre-booster injection, GMTs were comparable between treatment groups. They also tended to be within a similar range for serotype 1, serotype 2 and serotype 3. The GMTs of serotype 4 were lower in both groups. After the CYD-TDV dengue vaccine booster injection, GMTs increased as compared to pre-booster injection level. After the placebo injection, pre-booster injection seropositivity rates per serotype tended to remain stable after placebo injection. (Table 6).

TABLE 3

Non-inferiority of CYD-TDV dengue vaccine booster dose compared to the third CYD-TDV dengue vaccine dose from CYD13 or CYD30-Dengue PRNT-Per-Protocol Analysis Set

| Component | Post dose 3 in CYD13 and CYD30 (PD3) (N = 177) | | | Post booster dose in CYD64 (V04) (N = 177) | | | Ratio (Post booster/PD3) | | | Non-inferiority |
|---|---|---|---|---|---|---|---|---|---|---|
| | M | GM | (95% CI) | M | GM | (95% CI) | M | GM | (95% CI) | |
| Serotype 1 [PRNT-1/dil] | 176 | 316 | (233; 428) | 177 | 560 | (421; 744) | 176 | 1.66 | (1.33; 2.06) | Yes |
| Serotype 2 [PRNT-1/dil] | 175 | 356 | (275; 462) | 177 | 657 | (520; 830) | 175 | 1.82 | (1.43; 2.31) | Yes |
| Serotype 3 [PRNT-1/dil] | 175 | 640 | (516; 794) | 177 | 671 | (535; 843) | 175 | 1.04 | (0.841; 1.27) | Yes |
| Serotype 4 [PRNT-1/dil] | 176 | 243 | (195; 303) | 177 | 344 | (279; 424) | 176 | 1.32 | (1.01; 1.74) | Yes |

M: number of subjects with available data at both time points

For each serotype, non-inferiority was demonstrated if the lower limit of the two-sided 95% CI for the ratio is greater than ½. Overall non-inferiority will be demonstrated if all 4 serotypes achieve non-inferiority

TABLE 4

Analysis of covariance of post-booster titers against each of the four serotypes with the parental dengue virus strains-Dengue PRNT-Per-Protocol Analysis Set.

| Component | CYD Dengue Vaccine Group (N = 177) | | | Placebo Group (N = 64) | | | Difference (Dengue-Placebo) | | Ratio (Dengue/Placebo) | | p value for baseline*group interaction term* | p value for group*country interaction term* |
|---|---|---|---|---|---|---|---|---|---|---|---|---|
| | M | LSMEAN | (95% CI) | M | LSMEAN | (95% CI) | LSMEAN | (95% CI) | GM | (95% CI) | | |
| Serotype 1 [PRNT-1/dil] | 177 | 2.74 | (2.67; 2.82) | 64 | 2.43 | (2.32; 2.55) | 0.310 | (0.176; 0.445) | 2.04 | (1.50; 2.78) | 0.0004 | 0.3250 |
| Serotype 2 [PRNT-1/dil] | 177 | 2.79 | (2.71; 2.86) | 64 | 2.55 | (2.43; 2.66) | 0.242 | (0.107; 0.376) | 1.74 | (1.28; 2.38) | 0.0021 | 0.7881 |

TABLE 4-continued

Analysis of covariance of post-booster titers against each of the four serotypes with the parental dengue virus strains-Dengue PRNT-Per-Protocol Analysis Set.

| Component | CYD Dengue Vaccine Group (N = 177) | | | Placebo Group (N = 64) | | | Difference (Dengue-Placebo) | | Ratio (Dengue/Placebo) | | p value for baseline*group interaction term* | p value for group*country interaction term* |
|---|---|---|---|---|---|---|---|---|---|---|---|---|
| | M | LSMEAN | (95% CI) | M | LSMEAN | (95% CI) | LSMEAN | (95% CI) | GM | (95% CI) | | |
| Serotype 3 [PRNT-1/dil] | 177 | 2.86 | (2.79; 2.93) | 64 | 2.59 | (2.48; 2.71) | 0.266 | (0.135; 0.398) | 1.85 | (1.37; 2.50) | 0.0002 | 0.1830 |
| Serotype 4 [PRNT-1/dil] | 177 | 2.55 | (2.47; 2.64) | 64 | 2.21 | (2.08; 2.35) | 0.341 | (0.186; 0.495) | 2.19 | (1.53; 3.13) | 0.0001 | 0.6498 |

M: number of subjects available for the endpoint
LSMEAN: least squares of mean
Difference in LSMEANS and 95% CI were calculated using the analysis of covariance with pre-booster titer value and country as covariates without any interaction term
*p value for the interaction terms were derived from the analysis of covariance on post-booster titers with pre-booster titer value and country as covariates with the interaction term between the pre-booster titers and the randomized group, plus the interaction term between country and the randomized group.

TABLE 5

Superiority of CYD-TDV dengue vaccine booster dose compared to the third CYD-TDV dengue vaccine dose from previous trials-Dengue PRNT-Full Analysis Set

| Component | Post dose 3 in CYD13 and CYD30 (PD3) (N = 185) | | | Post booster dose in CYD64 (V04) (N = 185) | | | Ratio (Post booster/PD3) | | | Superiority |
|---|---|---|---|---|---|---|---|---|---|---|
| | M | GM | (95% CI) | M | GM | (95% CI) | M | GM | (95% CI) | |
| Serotype 1 [PRNT-1/dil] | 184 | 302 | (224; 406) | 185 | 536 | (404; 710) | 184 | 1.66 | (1.34; 2.06) | Yes |
| Serotype 2 [PRNT-1/dil] | 183 | 340 | (264; 439) | 185 | 653 | (519; 823) | 183 | 1.90 | (1.49; 2.41) | Yes |
| Serotype 3 [PRNT-1/dil] | 183 | 611 | (495; 755) | 185 | 662 | (529; 827) | 183 | 1.07 | (0.870; 1.31) | No |
| Serotype 4 [PRNT-1/dil] | 184 | 239 | (193; 295) | 185 | 347 | (283; 426) | 184 | 1.37 | (1.05; 1.78) | Yes |

M: number of subjects with available data at both time points
For each serotype, superiority will be demonstrated if the lower limit of the two-sided 95% CI for the ratio is greater than 1. Overall superiority will be demonstrated if all 4 serotypes achieve superiority

TABLE 6

Summary of geometric means of titers and geometric means of individual titer ratios of antibody against each serotype with the parental dengue virus strains at pre- and post-booster injection-Dengue PRNT-Per-Protocol Analysis Set

| Component | Time point/ratio | CYD Dengue Vaccine Group (N = 177) | | | Placebo Group (N = 64) | | |
|---|---|---|---|---|---|---|---|
| | | M | GM | (95% CI) | M | GM | (95% CI) |
| Serotype 1 [PRNT-1/dil] | V01 (D0) | 177 | 325 | (233; 452) | 64 | 349 | (201; 607) |
| | V04 (D28) | 177 | 560 | (421; 744) | 64 | 297 | (162; 547) |
| | Ratio V04 (D28)/V01 (D0) | 177 | 1.59 | (1.33; 1.90) | 64 | 0.798 | (0.623; 1.02) |
| Serotype 2 [PRNT-1/dil] | V01 (D0) | 177 | 360 | (267; 484) | 64 | 323 | (195; 535) |
| | V04 (D28) | 177 | 657 | (520; 830) | 64 | 354 | (205; 610) |
| | Ratio V04 (D28)/V01 (D0) | 177 | 1.70 | (1.43; 2.03) | 64 | 1.03 | (0.754; 1.40) |
| Serotype 3 [PRNT-1/dil] | V01 (D0) | 177 | 357 | (269; 472) | 64 | 442 | (270; 724) |
| | V04 (D28) | 177 | 671 | (535; 843) | 64 | 432 | (266; 700) |
| | Ratio V04 (D28)/V01 (D0) | 177 | 1.78 | (1.47; 2.16) | 64 | 0.946 | (0.749; 1.19) |
| Serotype 4 [PRNT-1/dil] | V01 (D0) | 177 | 162 | (134; 195) | 64 | 161 | (108; 242) |
| | V04 (D28) | 177 | 344 | (279; 424) | 64 | 161 | (110; 237) |
| | Ratio V04 (D28)/V01 (D0) | 177 | 2.09 | (1.65; 2.63) | 64 | 0.946 | (0.777; 1.15) |

M: number of subjects available for the endpoint

The seroconversion rates for 3 of the 4 serotypes were meaningfully different between treatment groups 28 days post-booster injection. The seroconversion rate for serotype 1 was 16.9% (95% CI: 11.7; 23.3) in CYD-TDV Dengue Vaccine Group and 3.1% (95% CI: 0.4; 10.8) in the Placebo Group; for serotype 2, it was 19.2% (95% CI: 13.7; 25.8) and 17.2% (95% CI: 8.9; 28.7); for serotype 3, the seroconversion rate was 20.3% (95% CI: 14.7; 27.0) and 4.7% (95% CI: 1.0; 13.1); and for serotype 4, it was 19.8% (95% CI: 14.2; 26.4) and 6.3% (95% CI: 1.7; 15.2), respectively. One of the plausible explanations of the high seroconversion rate against serotype 2 in the Placebo Group as compared to the CYD-TDV Dengue Vaccine Group is the impact of a natural infection booster effect on GMTs.

Dengue Serostatus at Baseline

The immune response to CYD-TDV dengue vaccine booster injection was analyzed according to the serostatus of subjects at baseline (i.e. at D0 in the previous trials CYD13 and CYD30). Among the 177 subjects enrolled in the CYD-TDV Dengue Vaccine Group, 136 (77%) subjects were dengue-immune at baseline and 41 (23%) were dengue non-immune. In the Placebo Group, there were 46 subjects dengue-immune at baseline and 18 non-immune subjects. Overall, NAb titers against each serotype at PD3, at pre-booster injection, as well as 28 days post-booster injection, were higher in subjects dengue-immune at baseline (Tables 7A and 7B).

Dengue Serostatus at Pre-Booster Injection

At pre-booster injection, GMTs (1/dil) ranged from 224 (serotype 4) to 668 (serotype 1) in dengue-immune subjects and from 29.6 (serotype 1) to 54.9 (serotype 4) in dengue non-immune subjects. At 28 days post-booster injection, GMTs (1/dil) ranged from 343 (serotype 4) to 940 (serotype 1) in dengue-immune subjects and from 100 (serotype 1) to 347 (serotype 4) in dengue non-immune subjects. Dengue serostatus at baseline had a meaningful difference in the seroconversion rate against each serotype. The seroconversion rates were higher in the dengue non-immune group of subjects. (Table 8).

Safety Evaluations

After the CYD-TDV dengue vaccine or the placebo injection, all subjects were assessed for immediate reactions, solicited reactions and unsolicited events or reactions. SAEs were collected throughout the study and serious and non-serious AESIs were collected in defined time-windows according to the type of AESI. An overview of the safety and reactogenicity up to 28 days post-booster injection is provided in table 9.

TABLE 8

Seroconversion rate against each serotype in dengue immune and non-immune subjects

| | Seroconversion Rate | |
| --- | --- | --- |
| Serotype | Dengue Immune | Dengue Non-Immune |
| 1 | 10.3% (95% CI: 5.7; 16.7) | 39.0% (95% CI: 24.2; 55.5) |
| 2 | 13.2% (95% CI: 8.0; 20.1) | 39.0% (95% CI: 24.2; 55.5) |
| 3 | 11.0% (95% CI: 6.3; 17.5) | 51.2% (95% CI: 35.1; 67.1) |
| 4 | 15.4% (95% CI: 9.8; 22.6) | 34.1% (95% CI: 20.1; 50.6) |

TABLE 9

Safety overview after booster injection.

| | CYD Dengue Vaccine Group (N = 187) | | | Placebo Group (N = 64) | | |
| --- | --- | --- | --- | --- | --- | --- |
| Subjects experiencing at least one: | n/M | % | (95% CI) | n/M | % | (95% CI) |
| Within 30 minutes after booster injection | | | | | | |
| Immediate unsolicited AE | 1/187 | 0.5 | (0.0; 2.9) | 0/64 | 0.0 | (0.0; 5.6) |
| Immediate unsolicited AR | 1/187 | 0.5 | (0.0; 2.9) | 0/64 | 0.0 | (0.0; 5.6) |
| Within 28 days after booster injection | | | | | | |
| Solicited reaction | 114/187 | 61.0 | (53.6; 68.0) | 31/64 | 48.4 | (35.8; 61.3) |
| Solicited injection site reaction | 47/187 | 25.1 | (19.1; 32.0) | 12/64 | 18.8 | (10.1; 30.5) |
| Solicited systemic reaction | 105/187 | 56.1 | (48.7; 63.4) | 28/64 | 43.8 | (31.4; 56.7) |
| Unsolicited AE | 48/187 | 25.7 | (19.6; 32.6) | 13/64 | 20.3 | (11.3; 32.2) |
| Unsolicited AR | 2/187 | 1.1 | (0.1; 3.8) | 0/64 | 0.0 | (0.0; 5.6) |
| Unsolicited non-serious AE | 48/187 | 25.7 | (19.6; 32.6) | 13/64 | 20.3 | (11.3; 32.2) |
| Unsolicited non-serious AR | 2/187 | 1.1 | (0.1; 3.8) | 0/64 | 0.0 | (0.0; 5.6) |
| Unsolicited non-serious injection site AR | 1/187 | 0.5 | (0.0; 2.9) | 0/64 | 0.0 | (0.0; 5.6) |
| Unsolicited non-serious systemic AE | 48/187 | 25.7 | (19.6; 32.6) | 13/64 | 20.3 | (11.3; 32.2) |
| Unsolicited non-serious systemic AR | 1/187 | 0.5 | (0.0; 2.9) | 0/64 | 0.0 | (0.0; 5.6) |
| AE leading to study discontinuationt | 0/187 | 0.0 | (0.0; 2.0) | 0/64 | 0.0 | (0.0; 5.6) |
| SAE | 0/187 | 0.0 | (0.0; 2.0) | 0/64 | 0.0 | (0.0; 5.6) |
| Death | 0/187 | 0.0 | (0.0; 2.0) | 0/64 | 0.0 | (0.0; 5.6) |
| Serious AESI | 0/187 | 0.0 | (0.0; 2.0) | 0/64 | 0.0 | (0.0; 5.6) |
| Non-serious AESI | 0/187 | 0.0 | (0.0; 2.0) | 0/64 | 0.0 | (0.0; 5.6) |
| During the study | | | | | | |
| SAE | 1/187 | 0.5 | (0.0; 2.9) | 0/64 | 0.0 | (0.0; 5.6) |
| Death | 0/187 | 0.0 | (0.0; 2.0) | 0/64 | 0.0 | (0.0; 5.6) |
| Serious AESI | 0/187 | 0.0 | (0.0; 2.0) | 0/64 | 0.0 | (0.0; 5.6) | n: number of subjects experiencing the endpoint listed in the first column

M: number of subjects with available data for the relevant endpoint

† Identified in the termination form as SAE or other AE or in an AE form that was at least Grade 1 and was within the time period indicated Overall, 61.0% of subjects in the CYD-TDV Dengue Vaccine Group and 48.4% in the Placebo Group experienced at least 1 solicited reaction after the booster injection. Among these subjects, 8.0% of subjects in the CYD-TDV Dengue Vaccine Group and 6.3% in the Placebo Group reported at least 1 Grade 3 solicited reaction. The Grade 3 solicited reactions that were reported in each group were mostly systemic reactions. Following the booster injection, the 2 treatment groups were comparable in terms of number, intensity, time of onset, and duration of solicited reactions. The most frequently reported solicited injection site reaction in both groups was injection site pain (24.6% in the CYD-TDV Dengue Vaccine Group and 18.8% in the Placebo Group). One (0.5%) subject experienced an injection site erythema (in the CYD-TDV Dengue Vaccine Group), and no injection site swelling was reported in either group. Most solicited injection site reactions reported were of Grade 1 intensity, occurred within 3 days, and resolved spontaneously within 3 days. One (0.5%) subject in the CYD-TDV Dengue Vaccine Group reported a Grade 3 reaction (injection site pain). The most frequently reported solicited systemic reaction in both groups was headache. At least 1 episode of headache was reported in 46.5% of subjects in the CYD-TDV Dengue Vaccine Group and in 34.4% of subjects in the Placebo Group after injection. The proportions of subjects who reported at least 1 episode of myalgia, malaise, and asthenia were within the same range and were similar across treatment groups (between 21% and 32%). Some 7.9% of subjects in the CYD-TDV Dengue Vaccine Group and 9.5% of subjects in the Placebo Group experienced at least 1 episode of fever. A total of 15 (8.0%) subjects in the CYD-TDV Dengue Vaccine Group and 4 (6.3%) subjects in the Placebo Group experienced at least 1 Grade 3 solicited systematic reaction. Headache was the most frequent Grade 3 systemic reaction, it was reported by 11 (5.9%) subjects from the CYD-TDV Dengue Vaccine Group and by 2 (3.1%) subjects in the Placebo Group. In the CYD-TDV Dengue Vaccine Group, one (0.5%) subject experienced at least 1 immediate unsolicited non-serious AR. The subject experienced a Grade 2 lump in the right axilla. This systemic event spontaneously resolved after 5 days and was assessed as related to the booster injection by the Investigator. Few unsolicited non-serious AEs reported within 28 days after injection were related to vaccination by the Investigator. One subject in the CYD-TDV Dengue Vaccine Group experienced an immediate unsolicited systemic AR (Grade 2 lump in the right axilla). A second subject in the same Group experienced 1 unsolicited non-serious AR (Grade 1 muscular weakness). For both subjects, the ARs occurred within 3 days after booster injection, spontaneously resolved within 4-7 days. Five SAE had been reported, it was considered as not related to vaccination. No AEs considered as significant (i.e., AEs and SAEs leading to discontinuation, AESIs, and hospitalized VCD cases) and None deaths were reported within 28 days after booster injection.

Long Term Follow Up

Persistence of neutralizing antibodies at six months and 1 year post-booster/placebo dose was measured by PRNT in available subjects (both dengue naïve and dengue immune at baseline) and the results are shown by serotype in Tables 10 to 14. As has been seen with other long term follow up analyses of recipients of CYD dengue vaccine, there was a decline in neutralizing antibody titres in the six month period following the administration of Dengvaxia® (booster dose), but after that point, neutralizing antibody titres stabilized, at least until 1 year post booster. Surprisingly, in subjects who were dengue naïve at baseline, the relative rate of decline was lower than in subjects who were dengue immune at baseline. For example, in immune subjects, the GMT levels at 12 months post booster dose for all four serotypes had already fallen below the GMT levels measured just before administration of the booster dose (i.e. at V01/D0). However, in naïve subjects, the GMT levels at 12 months post booster dose for all four serotypes were higher than the GMT levels measured just before administration of the booster dose (i.e. at V01/D0). This result is most easily seen in Table 15, which shows the M12:D0 GMT ratios for each serotype in both baseline naïve and baseline immune subjects. Thus it can be seen that the additive effect of the booster dose in baseline naïve subjects is surprisingly more durable in baseline naïve subjects than in baseline immune patients.

TABLE 11

Summary of Geometric Mean Titers of antibodies against each serotype with the parental dengue virus strains by baseline dengue status in CYD13/CYD30-Dengue PRNT-Per Protocol Analysis Set. SEROTYPE 1

| | SEROTYPE 1 [PRNT-1/dil] | | | | | | | | | | | |
|---|---|---|---|---|---|---|---|---|---|---|---|---|
| | IMMUNE | | | | | | NAIVE | | | | | |
| | CYD Dengue Vaccine Group (N = 177) | | | Placebo Group (N = 64) | | | CYD Dengue Vaccine Group (N = 177) | | | Placebo Group (N = 64) | | |
| Time point | M | GM | (95% CI) | M | GM | (95% CI) | M | GM | (95% CI) | M | GM | (95% CI) |
| Post dose 3 in CYD13 and CYD30 (PD3) | 136 | 656 | (501; 861) | 46 | 463 | (278; 771) | 40 | 26.2 | (17.0; 40.4) | 18 | 39.9 | (19.3; 82.4) |
| V01 (D0) | 136 | 668 | (498; 895) | 46 | 725 | (413; 1273) | 41 | 29.6 | (15.6; 56.1) | 19 | 54.0 | (21.4; 136) |
| V04 (D28) | 136 | 940 | (723; 1222) | 46 | 650 | (358; 1181) | 41 | 100 | (52.5; 192) | 18 | 40.4 | (12.6; 130) |
| V05 (M6) | 134 | 469 | (362; 607) | 45 | 396 | (237; 663) | 40 | 42.4 | (25.1; 71.6) | 18 | 31.2 | (11.0; 88.2) |
| V06 (M12) | 132 | 473 | (366; 611) | 46 | 351 | (221; 559) | 38 | 38.6 | (23.0; 64.6) | 16 | 29.2 | (11.0; 77.9) |

M: number of subjects available for the endpoint
V01 (D0): pre-booster or placebo injection
V0 (M6): 6 months post booster or placebo injection
GM: Geometric Mean
V04 (D28): 28 days post booster or placebo injection
V06 (M12): 12 months post booster or placebo injection

TABLE 12

Summary of Geometric Mean Titers of antibodies against each serotype with the parental dengue virus strains by baseline dengue status in CYD13/CYD30-Dengue PRNT-Per Protocol Analysis Set. SEROTYPE 2

| | SEROTYPE 2 [PRNT-1/dil] | | | | | | | | | | | |
|---|---|---|---|---|---|---|---|---|---|---|---|---|
| | IMMUNE | | | | | | NAIVE | | | | | |
| | CYD Dengue Vaccine Group (N = 177) | | | Placebo Group (N = 64) | | | CYD Dengue Vaccine Group (N = 177) | | | Placebo Group (N = 64) | | |
| Time point | M | GM | (95% CI) | M | GM | (95% CI) | M | GM | (95% CI) | M | GM | (95% CI) |
| Post dose 3 in CYD13 and CYD30 (PD3) | 135 | 613 | (474; 792) | 46 | 511 | (365; 713) | 40 | 57.1 | (39.6; 82.3) | 18 | 79.9 | (39.3; 163) |
| V01 (D0) | 136 | 657 | (505; 853) | 46 | 647 | (408; 1025) | 41 | 48.9 | (25.4; 94.1) | 18 | 55.0 | (20.2; 150) |
| V04 (D28) | 136 | 922 | (734; 1158) | 46 | 705 | (439; 1132) | 41 | 213 | (121; 375) | 18 | 61.0 | (17.5; 213) |
| V05 (M6) | 134 | 609 | (500; 741) | 45 | 617 | (435; 873) | 40 | 151 | (89.5; 256) | 18 | 72.6 | (27.7; 191) |
| V06 (M12) | 132 | 398 | (327; 485) | 46 | 388 | (288; 523) | 38 | 69.4 | (42.3; 114) | 16 | 47.2 | (18.1; 123) |

M: number of subjects available for the endpoint
V01 (D0): pre-booster or placebo injection
V05 (M6): 6 months post booster or placebo injection
GM: Geometric Mean
V04 (D28): 28 days post booster or placebo injection
V06 (M12): 12 months post booster or placebo injection

TABLE 13

Summary of Geometric Mean Titers of antibodies against each serotype with the parental dengue virus strains by baseline dengue status in CYD13/CYD30-Dengue PRNT-Per Protocol Analysis Set. SEROTYPE 3

| | SEROTYPE 3 [PRNT-1/dil] | | | | | | | | | | | |
|---|---|---|---|---|---|---|---|---|---|---|---|---|
| | IMMUNE | | | | | | NAIVE | | | | | |
| | CYD Dengue Vaccine Group (N = 177) | | | Placebo Group (N = 64) | | | CYD Dengue Vaccine Group (N = 177) | | | Placebo Group (N = 64) | | |
| Time point | M | GM | (95% CI) | M | GM | (95% CI) | M | GM | (95% CI) | M | GM | (95% CI) |
| Post dose 3 in CYD13 and CYD30 (PD3) | 134 | 1045 | (849; 1286) | 46 | 921 | (627; 1353) | 41 | 129 | (98.1; 168) | 18 | 138 | (82.0; 234) |
| V01 (D0) | 136 | 638 | (502; 811) | 46 | 918 | (581; 1452) | 41 | 51.8 | (27.4; 97.9) | 18 | 68.3 | (28.7; 163) |
| V04 (D28) | 136 | 866 | (689; 1089) | 46 | 857 | (561; 1311) | 41 | 288 | (163; 510) | 18 | 74.8 | (27.8; 201) |
| V05 (M6) | 134 | 748 | (596; 939) | 45 | 776 | (503; 1197) | 40 | 132 | (79.5; 221) | 18 | 113 | (44.5; 284) |
| V06 (M12) | 132 | 433 | (347; 540) | 46 | 528 | (362; 769) | 38 | 88.0 | (54.5; 142) | 16 | 83.4 | (34.4; 202) |

M: number of subjects available for the endpoint
V01 (D0): pre-booster or placebo injection
V05 (M6): 6 months post booster or placebo injection
GM: Geometric Mean
V04 (D28): 28 days post booster or placebo injection
V06 (M12): 12 months post booster or placebo injection

TABLE 14

Summary of Geometric Mean Titers of antibodies against each serotype with the parental dengue virus strains by baseline dengue status in CYD13/CYD30-Dengue PRNT-Per Protocol Analysis Set. SEROTYPE 4

| | SEROTYPE 4 [PRNT-1/dil] | | | | | | | | | | | |
|---|---|---|---|---|---|---|---|---|---|---|---|---|
| | IMMUNE | | | | | | NAIVE | | | | | |
| | CYD Dengue Vaccine Group (N = 177) | | | Placebo Group (N = 64) | | | CYD Dengue Vaccine Group (N = 177) | | | Placebo Group (N = 64) | | |
| Time point | M | GM | (95% CI) | M | GM | (95% CI) | M | GM | (95% CI) | M | GM | (95% CI) |
| Post dose 3 in CYD13 and CYD30 (PD3) | 135 | 315 | (249; 400) | 45 | 346 | (253; 475) | 41 | 103 | (65.9; 162) | 18 | 119 | (71.9; 197) |

TABLE 14-continued

Summary of Geometric Mean Titers of antibodies against each serotype with the parental dengue virus strains by baseline dengue status in CYD13/CYD30-Dengue PRNT-Per Protocol Analysis Set. SEROTYPE 4

| | SEROTYPE 4 [PRNT-1/dil] | | | | | | | | | | | |
|---|---|---|---|---|---|---|---|---|---|---|---|---|
| | IMMUNE | | | | | | NAIVE | | | | | |
| | CYD Dengue Vaccine Group (N = 177) | | | Placebo Group (N = 64) | | | CYD Dengue Vaccine Group (N = 177) | | | Placebo Group (N = 64) | | |
| Time point | M | GM | (95% CI) | M | GM | (95% CI) | M | GM | (95% CI) | M | GM | (95% CI) |
| V01 (D0) | 136 | 224 | (186; 269) | 46 | 307 | (214; 441) | 41 | 54.9 | (37.2; 80.9) | 18 | 31.2 | (16.1; 60.3) |
| V04 (D28) | 136 | 343 | (281; 418) | 46 | 287 | (205; 402) | 41 | 347 | (183; 657) | 18 | 37.0 | (17.9; 76.6) |
| V05 (M6) | 134 | 249 | (213; 292) | 45 | 247 | (193; 315) | 40 | 185 | (117; 295) | 18 | 49.9 | (26.2; 95.0) |
| V06 (M12) | 132 | 192 | (164; 225) | 46 | 193 | (157; 238) | 38 | 110 | (69.1; 175) | 16 | 37.8 | (20.9; 68.3) |

M: number of subjects available for the endpoint
V01 (D0): pre-booster or placebo injection
V05 (M6): 6 months post booster or placebo injection
GM: Geometric Mean
V04 (D28): 28 days post booster or placebo injection
V06 (M12): 12 months post booster or placebo injection

TABLE 15

M12:D0 GMT ratios for each serotype in baseline naïve and baseline immune subjects

| | Baseline naïve | Baseline immune |
|---|---|---|
| Serotype 1 | 1.30 | 0.71 |
| Serotype 2 | 1.42 | 0.61 |
| Serotype 3 | 1.70 | 0.68 |
| Serotype 4 | 2.00 | 0.85 |

CONCLUSIONS

The primary objective of the CYD64 study is met. In subjects having received a 3-dose primary series of the CYD dengue vaccine 4-5 years before, the booster dose is non-inferior to the third dose, in terms of GMTRs.

In subjects having received a 3-dose primary series of the CYD dengue vaccine 4-5 years before, the booster dose is not superior to the third dose of the primary series, in terms of GMTRs. Overall superiority is not attained as individual serotypes' superiority is not demonstrated for serotype 3.

The CYD dengue vaccine booster increases GMTs of each serotype 28 days after injection.

The CYD dengue vaccine booster increases seropositivity rates against each and any serotypes.

The dengue serostatus at baseline influences both the persistence of GMTs at pre-booster injection and the level of GMTs post-booster injection; i.e., subjects that were dengue-immune at baseline tended to have higher GMTs both at pre- and post-booster injection.

At 28 days after injection, dengue non-immune subjects at baseline have a higher seroconversion rate for each serotype than dengue-immune subjects at baseline; i.e., the increases of GMTs between pre-booster and post-booster injection are greater in subjects that were dengue non-immune (i.e. dengue naïve) at baseline compared to dengue immune subjects at baseline. This difference between dengue immune and dengue non-immune subjects at baseline is also demonstrated in the GMT ratios comparing the GMTs 28 days post booster compared to the GMTs PD3 of the primary vaccination course.

The additive effect of the booster dose in baseline naïve subjects is more durable in baseline naïve subjects than in baseline immune patients.

A booster injection administered 4-5 years after a 3-dose primary schedule is quite similar, in terms of reactogenicity, to the first CYD dengue vaccine injection administered in CYD13 and CYD30.

Sequences Referred to in this Application:

TABLE 16

Sequences of the Sequence Listing

| SEQ ID NO. | Sequence |
|---|---|
| 1 | prM-E nucleotide sequence of the serotype 1 vaccinal strain which is derived from the PUO 359 (TVP-1140) wild type strain |
| 2 | prM-E nucleotide sequence of the serotype 2 vaccinal strain which is derived from the PUO 218 wild type strain |
| 3 | prM-E nucleotide sequence of the serotype 3 vaccinal strain which is derived from the PaH881/88 wild type strain |
| 4 | prM-E nucleotide sequence of the serotype 4 vaccinal strain which is derived from the 1228 (TVP 980) wild type strain |
| 5 | prM-E nucleotide sequence of the serotype 2 vaccinal strain derived from the MD1280 wild type strain (CYD-2V) |
| 6 | Entire nucleotide sequence of the VDV1 strain |
| 7 | Entire nucleotide sequence of the VDV2 strain |

The above listed nucleotide sequences constitute the positive strand RNA of the listed dengue viruses (i.e. the nucleotide sequence which is found in the corresponding viral particles). The equivalent DNA sequences (which may be used to manipulate and express the corresponding virus and which also form part of the disclosure of the present application), can be generated by replacing the nucleotide U with the nucleotide T. Such DNA sequences constitute the cDNA sequences of the corresponding dengue viruses.

The invention claimed is:

1. A method of booster vaccination for inducing in a human subject a neutralizing antibody response against dengue virus, said method comprising administering to said human subject a composition comprising a dengue antigen of each of serotypes 1 to 4 wherein each of said dengue antigens is independently selected from the list consisting of: (a) a live attenuated dengue virus and (b) a live attenuated chimeric dengue virus,
   wherein said subject has previously received a primary vaccination course against each of serotypes 1 to 4 of dengue virus, and said subject was dengue naïve before said primary vaccination course,
   wherein said booster vaccination is administered at least one year after the end of the primary vaccination course and results in at least a 2-fold increase in the neutralizing antibody titre against each of serotypes 1 to 4,
   wherein said dengue antigens of serotypes 1 to 4 comprise nucleic acid sequences having at least 90% identity to SEQ ID NOs: 1, 2, 3 and 4 respectively, and wherein
      the amino acid at position 226 of the Envelope (E) protein of the dengue antigen of serotype 2 is threonine,
      the amino acid at position 228 of the Envelope (E) protein of the dengue antigen of serotype 2 is glycine, and
      the amino acid at position 251 of the Envelope (E) protein of the dengue antigen of serotype 2 is valine.

2. The method according to claim 1, wherein the booster vaccination is administered at least two years after the end of the primary vaccination course.

3. The method according to claim 1, wherein said primary vaccination course is administered in one, two or three doses.

4. The method according to claim 1, wherein the subject has, before booster administration, a neutralizing antibody titer as measured using a dengue Plaque Reduction Neutralization Test (PRNT$_{50}$) test against each of serotypes 1 to 4 of at least 10 and less than 150.

5. The method according to claim 1, wherein said 2-fold increase in the neutralizing antibody titre against each of serotypes 1 to 4 is measured between 20 and 60 days after said booster vaccination.

6. The method according to claim 1, wherein said neutralizing antibody titre is measured using a dengue Plaque Reduction Neutralization Test (PRNT$_{50}$) test.

7. The method according to claim 1, wherein said vaccine composition administered for booster vaccination is identical to the vaccine composition previously administered during the primary vaccination course.

8. A method of inducing in a human subject a neutralizing antibody response against dengue virus, said method comprising administering to said human subject a composition comprising a dengue antigen of each of serotypes 1 to 4, wherein said dengue antigens of serotypes 1 to 4 are each independently selected from the group consisting of a live attenuated dengue virus and a live attenuated chimeric dengue virus, wherein said dengue antigens of serotypes 1 to 4 comprise nucleic acid sequences having at least 90% identity to SEQ ID NOs: 1, 2, 3 and 4 respectively;
   wherein
      the amino acid at position 226 of the Envelope (E) protein of the dengue antigen of serotype 2 is threonine,
      the amino acid at position 228 of the Envelope (E) protein of the dengue antigen of serotype 2 is glycine, and
      the amino acid at position 251 of the Envelope (E) protein of the dengue antigen of serotype 2 is valine,
   wherein said composition is administered as:
      (a) a primary vaccination, followed at least 1 year after the end of the primary vaccination course by
      (b) a booster vaccination,
   and wherein the human subject is initially dengue naïve.

9. The method according to claim 8, wherein the booster immunization is administered at least two years after the end of the primary vaccination course.

10. The method according to claim 8, wherein said primary vaccination course is administered in one, two or three doses.

11. The method according to claim 8, wherein said subject is at least around 9 years of age.

12. The method according to claim 8, wherein said booster vaccination results in at least a 2-fold increase in the neutralizing antibody titre against each of serotypes 1 to 4, when compared with the neutralizing antibody titres induced after the primary vaccination.

13. The method according to claim 12, wherein said 2-fold increase in the neutralizing antibody titre against each of serotypes 1 to 4 is measured between 20 and 60 days after said booster vaccination.

14. The method according to claim 12, wherein said neutralizing antibody titre is measured using a dengue Plaque Reduction Neutralization Test (PRNT$_{50}$) test.

15. The method according to claim 1, wherein said human subject is protected against dengue disease.

16. The according to claim 1, wherein said subject is aged between 9 months and 60 years old.

17. The method according to claim 8, wherein said primary vaccination course consists in administration of 3 vaccine doses, wherein the second dose is administered about 6 months after the first dose and the third dose is administered about 6 months after the second dose.

18. The method according to claim 1, wherein the booster immunization is administered less than 20 years after the end of the primary vaccination course.

19. The method according to claim 1, wherein the human subject is resident in a dengue endemic area.

20. The method according to claim 1, wherein said live attenuated chimeric dengue virus comprises a genome from a first flavivirus in which the prM-E sequence has been replaced with a prM-E sequence of a dengue virus.

21. A method of booster vaccination for inducing in a human subject a neutralizing antibody response against dengue virus, said method comprising administering to said human subject a composition comprising a dengue antigen of each of serotypes 1 to 4 wherein each of said dengue antigens is independently selected from the list consisting of: (a) a live attenuated dengue virus and (b) a live attenuated chimeric dengue virus,
wherein said subject has previously received a primary vaccination course against each of serotypes 1 to 4 of dengue virus, and said subject was dengue naïve before said primary vaccination course,
wherein said booster vaccination is administered at least one year after the end of the primary vaccination course and results in at least a 2-fold increase in the neutralizing antibody titre against each of serotypes 1 to 4;
wherein said dengue antigens of serotypes 1, 3 and 4 comprise nucleic acid sequences having at least 90% identity to SEQ ID NOs: 1, 3 and 4 respectively,
wherein said dengue antigen of serotype 2 comprises a nucleic acid sequence having at least 95% identity to SEQ ID No: 2; and
wherein Envelope (E) protein encoded by the nucleic acid sequence of the dengue antigen of serotype 2 comprises a threonine residue at the position within the protein which correspondence to position 226 of SEQ ID NO: 2, a glycine residue at the position within the protein which corresponds to position 228 of SEQ ID NO: 2 and a valine residue at the position within the protein which corresponds to position 251 of SEQ ID NO: 2.

22. A method of inducing in a human subject a neutralizing antibody response against dengue virus, said method comprising administering to said human subject a composition comprising a dengue antigen of each of serotypes 1 to 4, wherein said dengue antigens of serotypes 1 to 4 are each independently selected from the group consisting of a live attenuated dengue virus and a live attenuated chimeric dengue virus, wherein said dengue antigens of serotypes 1, 3 and 4 comprise nucleic acid sequences having at least 90% identity to SEQ ID NOs: 1, 3 and 4 respectively,
wherein said dengue antigen of serotype 2 comprises a nucleic acid sequence having at least 95% identity to SEQ ID No: 2; and
wherein Envelope (E) protein encoded by the nucleic acid sequence of the dengue antigen of serotype 2 comprises a threonine residue at the position within the protein which correspondence to position 226 of SEQ ID NO: 2, a glycine residue at the position within the protein which corresponds to position 228 of SEQ ID NO: 2 and a valine residue at the position within the protein which corresponds to position 251 of SEQ ID NO: 2,
wherein said composition is administered as:
(a) a primary vaccination, followed at least 1 year after the end of the primary vaccination course by
(b) a booster vaccination,
and wherein the human subject is initially dengue naïve.

* * * * *